US008105779B2

(12) United States Patent
Cunningham et al.

(10) Patent No.: US 8,105,779 B2
(45) Date of Patent: Jan. 31, 2012

(54) **COMPOSITIONS AND METHODS FOR DETECTING THE PRESENCE OF *CRYPTOSPORIDIUM PARVUM* IN A TEST SAMPLE**

(76) Inventors: Melissa M. Cunningham, Philomath, OR (US); Paul D. Stull, Wilmington, DE (US); William G. Weisburg, San Diego, CA (US)

( * ) Notice: Subject to any disclaimer, the term of this patent is extended or adjusted under 35 U.S.C. 154(b) by 0 days.

(21) Appl. No.: 13/183,312

(22) Filed: Jul. 14, 2011

(65) Prior Publication Data
US 2011/0269133 A1    Nov. 3, 2011

Related U.S. Application Data

(60) Continuation of application No. 12/555,679, filed on Sep. 8, 2009, now Pat. No. 8,008,017, which is a division of application No. 11/459,885, filed on Jul. 25, 2006, now Pat. No. 7,585,631, which is a continuation of application No. 09/954,586, filed on Sep. 11, 2001, now Pat. No. 7,081,527.

(60) Provisional application No. 60/232,028, filed on Sep. 12, 2000.

(51) Int. Cl.
*C12Q 1/68* (2006.01)
*C07H 21/02* (2006.01)
*C07H 21/04* (2006.01)

(52) U.S. Cl. .................. 435/6.1; 536/23.1; 536/24.3

(58) Field of Classification Search .................. 435/6.1; 536/23.1, 24.3
See application file for complete search history.

(56) References Cited

U.S. PATENT DOCUMENTS

| | | | |
|---|---|---|---|
| 4,851,330 A | 7/1989 | Kohne | |
| 5,030,557 A | 7/1991 | Hogan et al. | |
| 5,399,491 A | 3/1995 | Kacian et al. | |
| 5,474,796 A | 12/1995 | Brennan | |
| 5,539,082 A | 7/1996 | Nielsen et al. | |
| 5,556,774 A | 9/1996 | Wiedenmann et al. | |
| 5,591,434 A | 1/1997 | Jenkins et al. | |
| 5,595,874 A | 1/1997 | Hogan et al. | |
| 5,690,825 A | 11/1997 | Parton | |
| 5,693,472 A | 12/1997 | Steele et al. | |
| 5,770,368 A | 6/1998 | De Leon et al. | |
| 5,789,190 A | 8/1998 | Crabb et al. | |
| 5,820,767 A | 10/1998 | Kane et al. | |
| 5,840,488 A | 11/1998 | Hogan | |
| 5,925,517 A | 7/1999 | Tyagi et al. | |
| 6,054,279 A | 4/2000 | Nadeau et al. | |
| 6,063,604 A | 5/2000 | Wick et al. | |
| 6,110,665 A | 8/2000 | Fenger et al. | |
| 6,130,038 A | 10/2000 | Becker et al. | |
| 6,146,838 A | 11/2000 | Williams et al. | |
| 6,146,855 A | 11/2000 | Williams et al. | |
| 6,361,945 B1 | 3/2002 | Becker et al. | |
| 7,081,527 B2 | 7/2006 | Cunningham et al. | |
| 7,585,631 B2 | 9/2009 | Cunningham et al. | |
| 8,008,017 B2 * | 8/2011 | Cunningham et al. | ....... 435/6.11 |
| 2001/0053519 A1 | 12/2001 | Fodor et al. | |
| 2002/0055116 A1 | 5/2002 | Cunningham et al. | |
| 2002/0143111 A1 | 10/2002 | Halverson et al. | |
| 2002/0193962 A1 | 12/2002 | Yakhini et al. | |
| 2004/0072239 A1 | 4/2004 | Renaud et al. | |
| 2010/0003693 A1 | 1/2010 | Cunningham et al. | |

FOREIGN PATENT DOCUMENTS

| | | |
|---|---|---|
| EP | 0652974 B1 | 5/1995 |
| WO | WO 9402635 A1 | 2/1994 |
| WO | WO 9404681 A1 | 3/1994 |
| WO | WO 9634978 A1 | 11/1996 |
| WO | WO 9640926 A2 | 12/1996 |
| WO | WO 9702281 A1 | 1/1997 |
| WO | WO 9703362 A1 | 1/1997 |
| WO | WO 9708204 A1 | 3/1997 |
| WO | 97/35026 A1 | 9/1997 |
| WO | WO 9742349 A1 | 11/1997 |
| WO | WO 9804675 A2 | 2/1998 |
| WO | WO 9806430 A1 | 2/1998 |

OTHER PUBLICATIONS

Cai et al., "*C. parvum* ribosomal RNA gene for 18S rRNA (pCPA911)", Database NCBI 'Online!, Jun. 1993, Accession No. X64340.

Cai et al., "PCR cloning and nucleotide sequence determination of the 18S rRNA genes and internal transcribed spacer 1 of the protozoan parasites *Cryptosporidium parvum* and *Cryptosporidium muris*", Biochim Biophys Acta., Jul. 1992, 1131(3):317-20.

Deere et al., "Evaluation of fluorochromes for flow cytometric detection of *Cryptosporidium parvum* oocysts labelled by fluorescent in situ hybridization", Lett Appl Microbiol., Dec. 1998, 27(6):352-6.

Deng et al., "Immunomagnetic Capture PCR to Detect Viable *Cryptosporidium parvum* Oocysts from Environmental Samples", Appl Environ Microbiol., Aug. 1997, 63(8):3134-8.

Hallier-Soulier et al., "An immunomagnetic separation polymerase chain reaction assay for rapid and ultra-sensitive detection of *Cryptosporidium parvum* in drinking water", FEMS Microbiol Lett., Jul. 1999, 176(2):285-9.

Laberge et al., "Detection of *Cryptosporidium parvum* in Raw Milk by Pcr and Oligonucleotide Probe Hybridization", Appl Environ Microbiol., Sep. 1996, 62(9):3259-64.

Lindquist, "Probes for the Specific Detection of *Cryptosporidium parvum*", Wat Res., 1997, 31 (10):2668-71.

Nelson, Genbank Accession No. AA167899, Aug. 23, 2000.

Pieniazek et al., "*Cryptosporidium parvum* 18S ribosomal RNA gene, complete", Database NCBI 'Online!, Mar. 1996, Accession No. L16996.

(Continued)

*Primary Examiner* — Ethan C Whisenant
(74) *Attorney, Agent, or Firm* — Charles B. Cappellari

(57) ABSTRACT

The present invention describes novel oligonucleotides targeted to nucleic acid sequences derived from *Cryptosporidium* organisms, and *Cryptosporidium parvum* organisms in particular, which are useful for determining the presence of *Cryptosporidium* organisms in a test sample. The oligonucleotides of the present invention include hybridization assay probes, helper probes and amplification primers. The present invention further describes a novel method for obtaining purified ribonucleic acid from viable oocysts.

19 Claims, 2 Drawing Sheets

OTHER PUBLICATIONS

Rochelle et al., "Comparison of primers and optimization of PCR conditions for detection of *Cryptosporidium parvum* and *Giardi lamblia* in water", Appl Environ Microbiol., Jan. 1997, 63(1):106-114, American Society for Microbiology, US.

Wang et al., "Electrochemical biosensor for detecting DNA sequences from the pathogenic protozoan *Cryptosporidium parvum*", Talanta, 1997, 44:2003-2010.

USPTO Office Action, U.S. Appl. No. 09/954,695, Feb. 22, 2005.

USPTO Office Action, U.S. Appl. No. 09/954,695, Mar. 5, 2004.

Awad-El-Kariem et al., "Detection and species identification of *Cryptosporidium* oocysts using a system based on PCR and endonuclease restriction", Parasitology, Jul. 1994, p. 19-22, vol. 109, Cambridge University Press, UK.

Balatbat et al., "Detection of *Cryptosporidium parvum* DNA in Human Feces by Nested PCR", J. Clin. Microbiol., Jul. 1996, p. 1769-1772, vol. 34, No. 7, American Society of Microbiology, US.

Carraway et al., "Genetic Markers Differentiate *C. parvum* Isolates", J. Eukaryot. Microbiol., Sep.-Oct. 1994, p. 26S, vol. 41, No. 5, Allen Press Inc., US.

Chrisp et al., "Similarities and differences between DNA of *Cryptosporidium parvum* and *C. wrairi* detected by the polymerase chain reaction", Folia Parasitol., 1994, p. 97-100, vol. 41, No. 2, Czech Academy of Sciences, CZ.

Deere et al., "Rapid method for fluorescent in situ ribosomal rna labeling of *Cryptosporidium parvum*", J. Appl. Microbiol., Nov. 1998, p. 807-818, vol. 85, No. 5, Blackwell Science Limited, UK.

Garcia et al., "Detection of Microsporidial Spores in Fecal Specimens from Patients Diagnosed with Cryptosporidiosis", J. Clin. Microbiol., Jul. 1994, p. 1739-1741, vol. 32, No. 7, American Society of Microbiology, US.

Kilani et al., "Geographical Variation in 18S rRNA Gene Sequence of *Cryptosporidium parvum*", Int. J. Parasitol., Apr. 1994, p. 303-306, vol. 24, No. 2, Elsevier Science Limited, UK.

Laxer et al., "DNA Sequences for the Specific Detection of *Cryptosporidium parvum* by the Polymerase Chain Reaction" Am. J. Trop. Med. Hyg., Dec. 1991, p. 688-694, vol. 45, No. 6, Allen Press Incorporated, US.

Lindquist et al., "Criteria for evaluation of proposed protozoan detection methods", J. Microbiol. Methods, Jul. 1999, p. 33-43, vol. 37, No. 1, Elsevier Science Publishers BV, NE.

Long et al., "The Diagnosis of Old and New Gastrointestinal Parasites", Clin. Lab. Med., Jun. 1995, p. 307-331, vol. 15, No. 2, W B Saunders Company, US.

Marsh et al., "Sequence Analysis and Comparison of Ribosomal DNA From Bovine Neospora to Similar Coccidial Parasites", J. Parasitol., Aug. 1995, p. 530-535, vol. 81, No. 4, American Society of Parasitologists, US.

Morgan et al., "Differentiation Between Human and Animal Isolates of *Cryptosporidium parvum* Using rDNA Sequencing and Direct PCR Analysis", J. Parasitol., Oct. 1997, p. 825-830, vol. 83, No. 5, American Society of Parasitologists, US.

Morgan et al, "Phylogenetic Analysis of *Cryptosporidium* Isolates from Captive Reptiles Using 18S rDNA Sequence Data and Random Amplified Polymorphic DNA Analysis", J. Parasitol., Jun. 1999, p. 525-530, vol. 85, No. 3, American Society of Parasitologists, US.

Rochelle et al., "Development of a Rapid Detection Procedure for *Cryptosporidium*, Using in Vitro Cell Culture Combined with PCR", J. Eukaryot. Microbiol., Sep.-Oct. 1996, p. 72S, vol. 43, No. 5, Allen Press, Inc., US.

Shepherd et al., "An Evaluation of Methods for the Simultaneous Detection of *Cryptosporidium* Oocysts and *Giardia* Cysts from Water", Appl. Environ. Microbiol., Apr. 1996, p. 1317-1322, vol. 62, No. 4, American Society for Microbiology, US.

Singh, "Molecular Methods for Diagnosis and Epidemiological Studies of Parasitic Infections", Int. J. Parasitol., Oct. 1997, p. 1135-1145, vol. 27, No. 10, Elsevier Science Limited, UK.

Slifko et al., "An in Vitro Method for Detecting Infectious *Cryptosporidium* Oocysts with Cell Culture", Appl. Environ. Microbiol., Sep. 1997, p. 3669-3675, vol. 63, No. 9, American Society for Microbiology, US.

Vesey et al., "The use of a ribosomal RNA targeted oligonucleotide probe for fluorescent labelling of viable *Cryptosporidium parvum* oocysts", J. Appl. Microbiol., Sep. 1998, p. 429-440, vol. 85, No. 3, Blackwell Science Limited, UK.

Webster et al., "Detection of *Cryptosporidium parvum* using a specific polymerase chain reaction" Vet. Parsitol., Oct. 1993, p. 35-44, vol. 50, No. 1-2, Elsevier Science Publishers BV, NE.

Webster et al., "Detection of *Cryptosporidium parvum* oocysts in faeces: comparison of conventional coproscopical methods and the polymerase chain reaction", Vet. Parasitol., Jan. 1996, p. 5-13, vol. 61, No. 1-2, Elsevier Science Publishers BV, NE.

Xiao et al., "Phylogenetic Analysis of *Cryptosporidium* Parasites Based on the Small-Subunit rRNA Gene Locus", Appl. Environ. Microbiol., Apr. 1999, p. 1578-1583, vol. 65, No. 4, American Society for Microbiology, US.

Xiao et al., "Genetic Diversity within *Cryptosporidium parvum* and Related *Cryptosporidium* Species," Appl. Environ. Microbiol., Aug. 1999, 65(8):3386-3391, American Society for Microbiology, US.

Zhu et al., "Direct Isolation of DNA from Patient Stools for Polymerase Chain Reaction Detection of *Cryptosporidium parvum*", J. Infect. Dis., May 1998, p. 1443-1446, vol. 177, No. 5, University of Chicago Press, US.

USPTO Office Action, U.S. Appl. No. 09/954,695, Jul. 1, 2003.
USPTO Office Action, U.S. Appl. No. 09/954,586, Jul. 1, 2003.
USPTO Office Action, U.S. Appl. No. 09/954,586, Mar. 5, 2004.
USPTO Office Action, U.S. Appl. No. 09/954,586, Mar. 9, 2005.
EPO Office Action, European Patent Application No. 01979893.3, Jan. 17, 2007.
EPO Office Action, European Patent Application No. 01979893.3, Jan. 23, 2008.
EPO Office Action, European Patent Application No. 01979893.3, May 10, 2010.
PCT Search Report, International Application No. PCT/US01/42192, May 20, 2003.
PCT International Preliminary Examination Report, International Application No. PCT/US01/42192, Dec. 29, 2004.
JPO Office Action, Japanese Patent Application No. 2002-527330, May 2, 2011.

* cited by examiner

COMPOSITIONS AND METHODS FOR DETECTING THE PRESENCE OF *CRYPTOSPORIDIUM PARVUM* IN A TEST SAMPLE

This application is a continuation of U.S. application Ser. No. 12/555,679, filed Sep. 8, 2009, which is a division of U.S. application Ser. No. 11/459,885, filed Jul. 25, 2006, now U.S. Pat. No. 7,585,631, which is a continuation of U.S. application Ser. No. 09/954,586, filed Sep. 11, 2001, now U.S. Pat. No. 7,081,527, which claims the benefit of U.S. Provisional Application No. 60/232,028, filed Sep. 12, 2000, the contents of each of which applications is hereby incorporated by reference herein in its entirety.

FIELD OF THE INVENTION

The present invention relates to hybridization assay probes, helper probes, amplification primers, nucleic acid compositions, probe mixes, methods and kits useful for determining the presence of *Cryptosporidium* organisms in general, and *Cryptosporidium parvum* organisms in particular, in a test sample of water, feces, food or other sample media.

The present invention further relates to a method for obtaining purified ribonucleic acid from a viable oocyst (e.g., a *Cryptosporidium* organism). The purified ribonucleic acid may then be made available for amplification and/or detection using one or more amplification oligonucleotides and/or a hybridization assay probe.

INCORPORATION BY REFERENCE

All references referred to herein are hereby incorporated by reference in their entirety. The incorporation of these references, standing alone, should not be construed as an assertion or admission by the inventors that any portion of the contents of all of these references, or any particular reference, is considered to be essential material for satisfying any national or regional statutory disclosure requirement for patent applications. Notwithstanding, the inventors reserve the right to rely upon any of such references, where appropriate, for providing material deemed essential to the claimed invention by an examining authority or court. No reference referred to herein is admitted to be prior art to the claimed invention.

BACKGROUND OF THE INVENTION

*Cryptosporidium* is an apicomplexan parasite capable of infecting a variety of animals, including humans. One particular species, *Cryptosporidium parvum*, is a coccidian parasite that poses particular threat to humans by causing gasteroenteritis in immuno-competent adults and infants, and occasionally life-threatening diarrhea in immuno-deficient individuals, such as infants, the elderly and AIDS patients. The mortality rate in AIDS patients infected with *Cryptosporidium parvum* is as high as fifty percent. Transmission of *Cryptosporidium parvum* is direct, by the fecal-oral route or by contamination of water supplies, swimming pools, and untreated surface water. Able to infect with as few as 30 microscopic oocysts, *Cryptosporidium parvum* is considered a leading cause of persistent diarrhea in developing countries and is a major threat to the U.S. water supply.

*Cryptosporidium parvum* exists in nature as a thick walled oocyst that is extremely resistant to environmental factors, exhibiting the ability to survive for months in the environment if maintained in a cool and moist setting. The oocysts are highly resistant to conventional chlorination of drinking water and their size presents a problem for water filtration systems typically employed by municipal water authorities. In fact, *Cryptosporidium parvum* oocysts are so robust that they are able to maintain their integrity and viability after a 24 hour exposure to full strength bleach. Their resistance to destruction by environmental and chemical means is particularly alarming since nearly ninety percent of all raw water supplies are infected with *Cryptosporidium parvum* oocysts.

In the United States, the method currently approved by the Environmental Protection Agency for detecting *Cryptosporidium parvum* is an antibody staining method referred to as "Method 1622". This method has several drawbacks, including the subjectivity of the assay, high antibody background resulting in an unacceptable number of false positives, and its labor intensive aspects, requiring hours of microscopic analysis. Other methods currently available for detecting *Cryptosporidium parvum*, including detection of genomic DNA by the polymerase chain reaction (PCR) and immunological assays such as the enzyme-linked immunosorbent assay (ELISA), have significant sensitivity and specificity problems. Thus, a need exists for a sensitive and specific assay which can be used to determine the presence of *Cryptosporidium* organisms, and *Cryptosporidium parvum* in particular, in a test sample, as well as a method for releasing the contents of the thick walled oocysts.

SUMMARY OF THE INVENTION

The present invention features oligonucleotides which are useful for determining whether organisms belonging to the genus *Cryptosporidium* or the species *Cryptosporidium parvum* are present in a test sample such as water, feces, food or other sample media. The featured oligonucleotides may be contained in amplification primers, hybridization assay probes and/or helper probes which are useful for amplifying and/or determining whether organisms belonging to the genus *Cryptosporidium* or the species *Cryptosporidium parvum* are present in a test sample.

For instance, the hybridization assay probes can preferentially hybridize to a target region present in nucleic acid derived from *Cryptosporidium* organisms to form a detectable probe:target hybrid indicating the presence of organisms belonging to the *Cryptosporidium* genus, which may include such species as *Cryptosporidium agni, Cryptosporidium baileyi, Cryptosporidium bovis, Cryptosporidium crotali, Cryptosporidium meleagridis, Cryptosporidium muris, Cryptosporidium nasorum, Cryptosporidium parvum, Cryptosporidium serpentis* and/or *Cryptosporidium wrairi*, as well as other organisms belonging to the *Cryptosporidium* genus. In one embodiment, the invention provides hybridization assay probes for determining whether *Cryptosporidium* organisms are present in a test sample, which probes preferably contain an at least 10 contiguous base region which is at least 80% complementary (preferably at least 90% complementary, and more preferably 100% complementary) to an at least 10 contiguous base region present in a target nucleic acid sequence present in a target nucleic acid derived from *Cryptosporidium* organisms, which target nucleic acid sequence is selected from the group consisting of (reading 5' to 3'):

```
SEQ ID NO: 1:
ctatcagctttagacggtaggg,

SEQ ID NO: 2:
cuaucagcuuuagacgguaggg,

SEQ ID NO: 3:
ccctaccgtctaaagctgatag,
and

SEQ ID NO: 4:
cccuaccgucuaaagcugauag.
```

These probes will preferentially hybridize to the target nucleic acid and not to nucleic acid derived from non-*Cryptosporidium* organisms under stringent hybridization assay conditions.

In another embodiment, the invention provides hybridization assay probes for determining whether organisms of the species *Cryptosporidium parvum* are present in a test sample, which probes preferably contain an at least 10 contiguous base region which is at least 80% complementary (preferably at least 90% complementary, and more preferably 100% complementary) to an at least 10 contiguous base region present in a target nucleic acid sequence present in a target nucleic acid derived from *Cryptosporidium parvum* organisms, which target nucleic acid sequence is selected from the group consisting of (reading 5' to 3'):

```
SEQ ID NO: 5:
gcgaaaaaactcgacttttatggaaggg,

SEQ ID NO: 6:
aactcgactttatggaaggg,

SEQ ID NO: 7:
aaaactcgactttatggaagggttg,

SEQ ID NO: 8:
gttaaagacaaactaatgcgaaagc,

SEQ ID NO: 9:
gcgaaaaaacucgacuuuauggaaggg,

SEQ ID NO: 10:
aacucgacuuuauggaaggg,

SEQ ID NO: 11:
aaaacucgacuuuauggaaggguug,

SEQ ID NO: 12:
guuaaagacaaacuaaugcgaaagc,

SEQ ID NO: 13:
cccttccataaagtcgagttttttcgc,

SEQ ID NO: 14:
cccttccataaagtcgagtt,

SEQ ID NO: 15:
caacccttccataaagtcgagtttt,

SEQ ID NO: 16:
gctttcgcattagtttgtctttaac,

SEQ ID NO: 17:
cccuuccauaaagucgaguuuuuucgc,

SEQ ID NO: 18:
cccuuccauaaagucgaguu,

SEQ ID NO: 19:
caacccuuccauaaagucgaguuuu,
and

SEQ ID NO: 20:
gcuuucgcauuaguuugucuuuaac.
```

These probes will preferentially hybridize to the target nucleic acid and not to nucleic acid derived from non-*Cryptosporidium parvum* organisms (especially *Cryptosporidium muris*, *Cryptosporidium baileyi* and *Cryptosporidium wrairi*) present in the test sample under stringent hybridization assay conditions.

Preferably, the *Cryptosporidium* and *Cryptosporidium parvum* probes of the present invention comprise an oligonucleotide up to 100 bases in length (preferably from 12 to 50 bases, and more preferably from 18 to 35 bases in length) and substantially complementary to the target nucleic acid sequence (preferably perfectly complementary to the first target nucleic acid sequence). The oligonucleotide may consist of deoxyribonucleic acid (DNA), ribonucleic acid (RNA), a combination DNA and RNA, or it may be a nucleic acid analog (e.g., a peptide nucleic acid) or contain one or more modified nucleosides (e.g., a ribonucleoside having a 2'-O-methyl substitution to the ribofuranosyl moiety).

The probes preferably include a detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester.

In another embodiment, the invention contemplates probe mixes that are useful for determining whether *Cryptosporidium* organisms, or *Cryptosporidium parvum* organisms in particular, are present in a test sample. For instance, to determine the presence of organisms from the genus *Cryptosporidium*, the probe mix may comprise one of the above-described *Cryptosporidium* probes and a helper probe. Preferably, the helper probe is an oligonucleotide up to 100 bases in length, more preferably from 12 to 50 bases in length, and even more preferably from 18 to 35 bases in length. Preferably, the helper probe contains an at least 10 contiguous base region which is at least 80% complementary (preferably at least 90% complementary, and more preferably 100% complementary) to an at least 10 contiguous base region present in a target nucleic acid sequence present in a target nucleic acid derived from *Cryptosporidium* organisms, which target sequence is selected from the group consisting of (reading 5' to 3'):

```
SEQ ID NO: 21:
gacatatcattcaagtttctgac,

SEQ ID NO: 22:
ttggcctaccgtggcaatgacggg,

SEQ ID NO: 23:
gacauaucauucaaguuucugac,

SEQ ID NO: 24:
uuggccuaccguggcaaugacggg,

SEQ ID NO: 25:
gtcagaaacttgaatgatatgtc,

SEQ ID NO: 26:
cccgtcattgccacggtaggccaa,

SEQ ID NO: 27:
gucagaaacuugaaugauauguc,

SEQ ID NO: 28:
cccgucauugccacgguaggccaa,
``` and mixtures thereof. The helper probes may be, but need not be, perfectly complementary to the target sequence.

To determine the presence of *Cryptosporidium parvum* organisms in a test sample, the probe mix may comprise one of the above-described *Cryptosporidium parvum* probes and a helper probe. Preferably, the helper probe is an oligonucleotide up to 100 bases in length, more preferably from 12 to 50 bases, and even more preferably from 18 to 35 bases in length. Preferably, the helper probe contains an at least 10 contiguous base region which is at least 80% complementary (preferably at least 90% complementary, and more preferably 100% complementary) to an at least 10 contiguous base region present in a target nucleic acid sequence present in a target nucleic acid derived from *Cryptosporidium parvum* organisms, which target sequence is selected from the group consisting of (reading 5' to 3'):

```
SEQ ID NO: 29:
ggataaccgtggtaattctagagctaatacat,

SEQ ID NO: 30:
ccgtggtaattctagagctaatacat,

SEQ ID NO: 31:
ttgtatttattagataaagaacc,

SEQ ID NO: 32:
ttgtatttattagataaagaaccaatata,

SEQ ID NO: 33:
ggauaaccgugguaauucuagagcuaauacau,

SEQ ID NO: 34:
ccgugguaauucuagagcuaauacau,

SEQ ID NO: 35:
uuguauuauuagauaaagaacc,

SEQ ID NO: 36:
uuguauuauuagauaaagaaccaauaua,

SEQ ID NO: 37:
atgtattagctctagaattaccacggttatcc,

SEQ ID NO: 38:
atgtattagctctagaattaccacgg,

SEQ ID NO: 39:
ggttctttatctaataaatacaa,

SEQ ID NO: 40:
tatattggttctttatctaataaatacaa,

SEQ ID NO: 41:
auguauuagcucuagaauuaccacgguuaucc,

SEQ ID NO: 42:
auguauuagcucuagaauuaccacgg,

SEQ ID NO: 43:
gguucuuuaucuaauaaauacaa,

SEQ ID NO: 44:
uauauugguucuuuaucuaauaaauacaa,
``` and mixtures thereof. The helper probes may be, but need not be, perfectly complementary to the target sequence.

In a preferred embodiment for the *Cryptosporidium parvum* probe mix, the hybridization assay probe comprises an oligonucleotide having an at least 10 contiguous base region which is at least 80% homologous to an at least 10 contiguous base region present in a sequence selected from the group consisting of: SEQ ID NO:5, SEQ ID NO:6, SEQ ID NO:9, SEQ ID NO:10, SEQ ID NO:13, SEQ ID NO:14, SEQ ID NO:17 and SEQ ID NO:18; and the helper probe comprises an oligonucleotide having an at least 10 contiguous base region which is at least 80% homologous to an at least 10 contiguous base region present in a sequence selected from the group consisting of: SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43 and SEQ ID NO:44.

In another preferred embodiment for the *Cryptosporidium parvum* probe mix, the hybridization assay probe comprises an oligonucleotide having an at least 10 contiguous base region which is at least 80% homologous to an at least 10 contiguous base region present in a sequence selected from the group consisting of: SEQ ID NO:5, SEQ ID NO:6, SEQ ID NO:9, SEQ ID NO:10, SEQ ID NO:13, SEQ ID NO:14, SEQ ID NO:17 and SEQ ID NO:18; and the probe mix comprises first and second helper probes, where the first helper probe comprises an oligonucleotide having an at least 10 contiguous base region which is at least 80% homologous to an at least 10 contiguous base region present in a sequence selected from the group consisting of: SEQ ID NO:29, SEQ ID NO:30, SEQ ID NO:33, SEQ ID NO:34, SEQ ID NO:37, SEQ ID NO:38, SEQ ID NO:41 and SEQ ID NO:42, and where the second helper probe comprises an oligonucleotide having an at least 10 contiguous base region which is at least 80% homologous to an at least 10 contiguous base region present in a sequence selected from the group consisting of: SEQ ID NO:31, SEQ ID NO:32, SEQ ID NO:35, SEQ ID NO:36, SEQ ID NO:39, SEQ ID NO:40, SEQ ID NO:43 and SEQ ID NO:44.

In another preferred embodiment for the *Cryptosporidium parvum* probe mix, the hybridization assay probe comprises an oligonucleotide having an at least 10 contiguous base region which is at least 80% homologous to an at least 10 contiguous base region present in a sequence selected from the group consisting of: SEQ ID NO:7, SEQ ID NO:11, SEQ ID NO:15 and SEQ ID NO:19; and the helper probe comprises an oligonucleotide having an at least 10 contiguous base region which is at least 80% homologous to an at least 10 contiguous base region present in a sequence selected from the group consisting of: SEQ ID NO:29, SEQ ID NO:30, SEQ ID NO:33, SEQ ID NO:34, SEQ ID NO:37, SEQ ID NO:38, SEQ ID NO:41 and SEQ ID NO:42.

The invention also contemplates compositions comprising stable nucleic acid duplexes formed between the above-described hybridization assay probes and/or helper probes and the target nucleic acids for the probes under stringent hybridization assay conditions.

The invention also features amplification primers useful for detecting the presence of *Cryptosporidium* organisms in an amplification assay. In one preferred embodiment, the invention provides at least one amplification primer for amplifying nucleic acid derived from *Cryptosporidium* organisms present in a test sample, which amplification primer preferably contains an at least 10 contiguous base region which is at least 80% complementary (preferably at least 90% complementary, and more preferably 100% complementary) to an at least 10 contiguous base region present in a target nucleic acid sequence present in a target nucleic acid derived from *Cryptosporidium* organisms, which target nucleic acid sequence is selected from the group consisting of (reading 5' to 3'):

```
SEQ ID NO: 45:
gccatgcatgtctaagtataaac,

SEQ ID NO: 46:
ggataaccgtggtaattctagag,

SEQ ID NO: 47:
ggtgactcataataactttacgg,

SEQ ID NO: 48:
ctaccacatctaaggaaggcag,

SEQ ID NO: 49:
gtatttaacagtcagaggtg,

SEQ ID NO: 50:
gccaaggatgttttcattaatc,
```

-continued

SEQ ID NO: 51:
gccaugcaugucuaaguauaaac,

SEQ ID NO: 52:
ggauaaccgugguaauucuagag,

SEQ ID NO: 53:
ggugacucauaauaacuuuacgg,

SEQ ID NO: 54:
cuaccacaucuaaggaaggcag,

SEQ ID NO: 55:
guauuuaacagucagaggug,

SEQ ID NO: 56:
gccaaggauguuuucauuaauc,

SEQ ID NO: 57:
gtttatacttagacatgcatggc,

SEQ ID NO: 58:
ctctagaattaccacggttatcc,

SEQ ID NO: 59:
ccgtaaagttattatgagtcacc,

SEQ ID NO: 60:
ctgccttccttagatgtggtag,

SEQ ID NO: 61:
cacctctgactgttaaatac,

SEQ ID NO: 62:
gattaatgaaaacatccttggc,

SEQ ID NO: 63:
guuuauacuuagacaugcauggc,

SEQ ID NO: 64:
cucuagaauuaccacgguuaucc,

SEQ ID NO: 65:
ccguaaaguuauuaugagucacc,

SEQ ID NO: 66:
cugccuuccuuagauguggguag,

SEQ ID NO: 67:
caccucugacuguuaaauac,
and

SEQ ID NO: 68:
gauuaaugaaaacauccuuggc.

The amplification primers optionally include a 5' sequence which is recognized by a RNA polymerase or which enhances initiation or elongation by RNA polymerase. When included, a T7 promoter, such as SEQ ID NO:69 aatttaatacgactcactatagggaga, is preferred.

The invention further contemplates amplification primers which, when contacted with a nucleic acid polymerase under amplification conditions, will bind to or cause extension through a nucleic acid region having a base sequence selected from the group consisting of: SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67 and SEQ ID NO:68. The amplification primers of this embodiment also optionally include a 5' sequence which is recognized by a RNA polymerase or which enhances initiation or elongation by RNA polymerase. The T7 promoter of SEQ ID NO:69 is preferred.

Amplification primers of the present invention are preferably employed in sets of at least two amplification primers. Preferred sets include a first amplification primer which contains an at least 10 contiguous base region which is at least 80% complementary to an at least 10 contiguous base region present in a sequence selected from the group consisting of: SEQ ID NO:45, SEQ ID NO:46, SEQ ID NO:49, SEQ ID NO:51, SEQ ID NO:52, SEQ ID NO:55, SEQ ID NO:57, SEQ ID NO:58; SEQ ID NO:61, SEQ ID NO:63, SEQ ID NO:64 and SEQ ID NO:67. The second amplification primer of these preferred sets contains an at least 10 contiguous base region which is at least 80% complementary to an at least 10 contiguous base region present in a sequence selected from the group consisting of: SEQ ID NO:47, SEQ ID NO:48, SEQ ID NO:50, SEQ ID NO:53, SEQ ID NO:54, SEQ ID NO:56, SEQ ID NO:59, SEQ ID NO:60; SEQ ID NO:62, SEQ ID NO:65, SEQ ID NO:66 and SEQ ID NO:68.

The invention additionally contemplates compositions comprising stable nucleic acid duplexes formed between the above-described amplification primers and the target nucleic acids for the primers under amplification conditions.

The invention further features methods for determining whether *Cryptosporidium* or *Cryptosporidium parvum* organisms are present in a test sample. In one embodiment, the invention provides a method for determining whether *Cryptosporidium* organisms are present in a test sample, where the method comprises the steps of: (a) contacting the test sample with one of the above-described hybridization assay probes for detecting *Cryptosporidium* organisms under conditions permitting the probe to preferentially hybridize to a target nucleic acid derived from a *Cryptosporidium* organism, thereby forming a probe:target hybrid stable for detection; and (b) determining whether the hybrid is present in the test sample as an indication of the presence or absence of *Cryptosporidium* organisms in the test sample. This method may further include the step of quantifying the amount of hybrid present in the test sample as a means for estimating the amount of *Cryptosporidium* organisms present in the test sample.

In another embodiment, the invention provides a method for determining whether *Cryptosporidium parvum* organisms are present in a test sample, where the method comprises the steps of: (a) contacting the test sample with one of the above-described hybridization assay probes for detecting *Cryptosporidium parvum* organisms under conditions permitting the probe to preferentially hybridize to a target nucleic acid derived from a *Cryptosporidium parvum* organism, thereby forming a probe:target hybrid stable for detection; and (b) determining whether the hybrid is present in the test sample as an indication of the presence or absence of *Cryptosporidium parvum* organisms in the test sample. This method may further include the step of quantifying the amount of hybrid present in the test sample as a means for estimating the amount of *Cryptosporidium parvum* organisms present in the test sample.

The methods for determining whether *Cryptosporidium* or *Cryptosporidium parvum* organisms are present in a test sample, or the amount of these organisms present in a test sample, may further include the step of contacting the test sample with at least one of the above-described helper probes, appropriate for *Cryptosporidium* or *Cryptosporidium parvum*, as desired. (Preferred hybridization assay probe and helper probe combinations are set forth above as probe mixes.) In addition to the helper probes, or in the alternative, the methods may further include the step of contacting the test sample with at least one of the above-described amplification primers, appropriate for amplifying a target nucleic acid sequence present in nucleic acid derived from *Cryptosporidium* or *Cryptosporidium parvum* organisms, as desired.

The invention also contemplates methods for amplifying a target nucleic acid sequence present in nucleic acid derived from a *Cryptosporidium* organism present in a test sample, where the method comprises the steps of: (a) contacting the test sample with at least one of the above-described amplification primers under amplification conditions; and (b) amplifying the target nucleic acid sequence. The target nucleic acid sequence amplified may be present in nucleic acid derived from *Cryptosporidium* organisms or, in particular, from *Cryptosporidium parvum* organisms. Preferred amplification methods will include a set of at least two of the above-described amplification primers.

In one embodiment, the method for amplifying a target nucleic acid sequence present in nucleic acid derived from a *Cryptosporidium* organism will further include the steps of: (a) contacting the test sample with a hybridization assay probe which preferentially hybridizes to the target nucleic acid sequence, or a complement thereof, under stringent hybridization conditions, thereby forming a probe:target hybrid stable for detection; and (b) determining whether the hybrid is present in the test sample as an indication of the presence or absence of *Cryptosporidium* or *Cryptosporidium parvum* organisms in the test sample. The above-described hybridization assay probes are especially preferred for this method.

The invention also contemplates kits for determining whether *Cryptosporidium* organisms are present in a test sample. These kits comprise at least one of the above-described hybridization assay probes specific for *Cryptosporidium*-derived nucleic acid and optionally include written instructions for determining the presence or amount of *Cryptosporidium* organisms in a test sample. In another embodiment, the kits further comprise at least one of the above-described helper probes appropriate for nucleic acid derived from *Cryptosporidium*. In a further embodiment, the kits also comprise at least one of the above-described amplification primers appropriate for amplifying a target nucleic acid sequence present in nucleic acid derived from *Cryptosporidium* organisms. In yet another embodiment, the kits further comprise at least one of the above-described helper probes and at least one of the above-described amplification primers.

Similarly, the invention contemplates kits for determining whether *Cryptosporidium parvum* organisms are present in a test sample. These kits comprise at least one of the above-described hybridization assay probes specific for *Cryptosporidium parvum*-derived nucleic acid and optionally include written instructions for determining the presence or amount of *Cryptosporidium parvum* organisms in a test sample. In another embodiment, the kits further comprise at least one of the above-described helper probes appropriate for nucleic acid derived from *Cryptosporidium parvum* organisms. In a further embodiment, the kits also comprise at least one of the above-described amplification primers appropriate for amplifying a target nucleic acid sequence present in nucleic acid derived from *Cryptosporidium parvum* organisms. In another embodiment, the kits comprise at least one of the above-described helper probes and at least one of the above-described amplification primers.

The invention also contemplates kits for amplifying a target nucleic acid sequence to present in nucleic acid derived from *Cryptosporidium* or *Cryptosporidium parvum* organisms, comprising at least one of the above-described amplification primers and optionally include written instructions for amplifying nucleic acid derived from *Cryptosporidium* or *Cryptosporidium parvum* organisms, as appropriate.

Those skilled in the art will appreciate that the hybridization assay probes of the present invention may be used as amplification primers or capture probes, the amplification primers of the present invention may be used as hybridization assay probes or capture probes, and the helper probes of the present invention may be used as amplification primers or capture probes, depending upon the degree of specificity required.

The present invention further features a method for obtaining purified RNA from a viable oocyst, such as a *Cryptosporidium* organism. Ribonucleic acid isolated from an oocyst may then be made available for amplification and/or detection using at least one of the above-described amplification primers and/or hybridization assay probes.

In a preferred embodiment, the method for obtaining purified RNA from a viable oocyst includes the steps of: (i) centrifuging a fluid sample suspected of containing oocysts at a speed and for a period of time sufficient to concentrate the oocysts within a vessel containing the fluid sample; (ii) removing a supernatant from the vessel which formed during the centrifuging step; (iii) resuspending the concentrated oocysts, if present, in a buffered solution; (iv) oscillating, or otherwise agitating (e.g., vortexing), the buffered solution in the presence of a plurality of particles at a rate and for a period of time sufficient to lyse the oocysts and release RNA therefrom; (v) immobilizing the released RNA on an RNA-binding filter (e.g., a silica-based matrix); (vi) purifying the released RNA by washing the filter one or more times with a buffered solution to remove oocyst components (e.g., proteins, DNA and other contaminants) other than the released RNA; and (vii) removing the purified RNA from the filter. The buffered solution used in step (iii) of this method preferably includes a chaotropic agent, such as guanidinium thiocyanate, which inactivates endogenous ribonucleases released from the oocysts. The particles used to lyse the oocysts may be, for example, glass, zirconia-glass, zirconia, stainless steel, chrome-steel or tungsten carbide, although zirconia-glass particles having a density of about 3.7 g/cc are preferred. The particles preferably have a generally spherical shape and preferably have an average diameter in the range of about 0.1 to about 2.5 mm, more preferably in the range of about 0.5 to about 1.0 mm, and most preferably have an average diameter of about 1.0 mm.

Other features and advantages of the invention will be apparent from the following description of the preferred embodiments thereof and from the claims.

DESCRIPTION OF THE PREFERRED EMBODIMENTS

Figure 1:
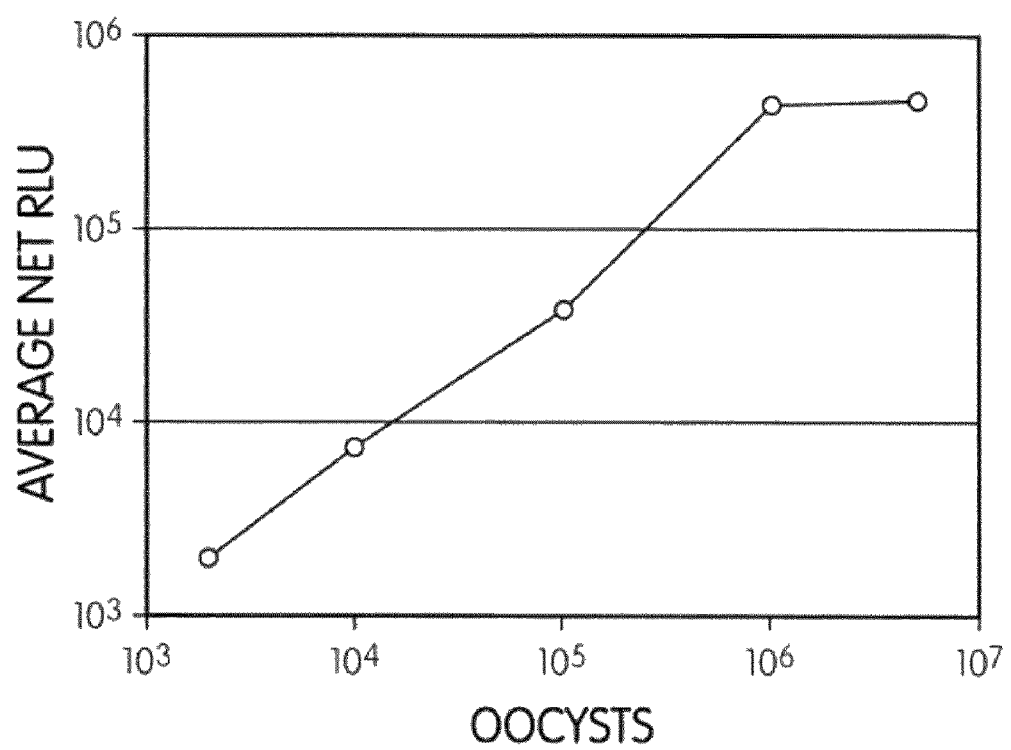
FIG. 1 is an oocyst titration graph plotting "Average Net RLU" versus "Oocysts" determined by hemocytometer counting. This figure indicates the oocyst load necessary to directly detect the presence of *Cryptosporidium parvum* in a test sample.

The present invention describes oligonucleotides targeted to nucleic acids derived from *Cryptosporidium* organisms which are particularly useful for determining the presence or absence of *Cryptosporidium* organisms generally, and

*Cryptosporidium parvum* organisms in particular, in a test sample. The oligonucleotides can aid in detecting *Cryptosporidium* organisms in different ways, such as by functioning as hybridization assay probes, helper probes and/or amplification primers. Hybridization assay probes of the present invention can preferentially hybridize to a target nucleic acid sequence present in a target nucleic acid derived from *Cryptosporidium* organisms under stringent hybridization assay conditions to form detectable duplexes which indicate the presence of *Cryptosporidium* organisms, or more specifically *Cryptosporidium parvum* organisms, in a test sample. Some of the probes are believed to be capable of distinguishing between *Cryptosporidium* and its known closest phylogenetic neighbors. Other of the probes are believed to be capable of distinguishing between *Cryptosporidium parvum* and its known closest phylogenetic neighbors. Helper probes of the present invention can hybridize to a target nucleic acid sequence present in nucleic acid derived from *Cryptosporidium* organisms under stringent hybridization assay conditions and can be used to enhance the formation of hybridization assay probe:target nucleic acid duplexes. Amplification primers of the present invention can hybridize to a target nucleic acid sequence present in nucleic acid derived from *Cryptosporidium* organisms under amplification conditions and can be used as primers in amplification reactions to generate *Cryptosporidium*, or more specifically *Cryptosporidium parvum*, derived nucleic acid. The probes and amplification primers may be used in assays for the detection and/or quantitation of *Cryptosporidium* or *Cryptosporidium parvum* organisms in a test sample.

The present invention further describes a method for obtaining purified RNA from a viable oocyst, such as a *Cryptosporidium* organism. The purified RNA may be made available for amplification with one or more amplification primers and/or detection with a hybridization assay probe.

A. Definitions

The following terms have the indicated meanings in the specification unless expressly indicated to have a different meaning.

By "target nucleic acid" or "target" is meant a nucleic acid containing a target nucleic acid sequence.

By "target nucleic acid sequence," "target nucleotide sequence," "target sequence" or "target region" is meant a specific deoxyribonucleotide or ribonucleotide sequence comprising all or part of the nucleotide sequence of a single-stranded nucleic acid molecule.

By "oligonucleotide" or "oligomer" is meant a polymer made up of two or more nucleoside subunits or nucleobase subunits coupled together. The oligonucleotide may be DNA and/or RNA and analogs thereof. The sugar groups of the nucleoside subunits may be ribose, deoxyribose and analogs thereof, including, for example, ribonucleosides having a 2'-O-methyl substitution to the ribofuranosyl moiety. (Oligonucleotides including nucleoside subunits having T substitutions and which are useful as hybridization assay probes, helper probes and/or amplification primers are disclosed by Becker et al., "Method for Amplifying Target Nucleic Acids Using Modified Primers," U.S. Pat. No. 6,130,038.) The nucleoside subunits may by joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. (DNA analogs having a pseudo peptide backbone are commonly referred to as "peptide nucleic acids" or "PNA" and are disclosed by Nielsen et al., "Peptide Nucleic Acids," U.S. Pat. No. 5,539,082.) Other non-limiting examples of oligonucleotides or oligomers contemplated by the present invention include nucleic acid analogs containing bicyclic and tricyclic nucleoside and nucleotide analogs referred to as "Locked Nucleic Acids," "Locked Nucleoside Analogues" or "LNA." (Locked Nucleic Acids are disclosed by Wang, "Conformationally Locked Nucleosides and Oligonucleotide," U.S. Pat. No. 6,083,482; Imanishi et al., "Novel Bicyclonucleoside and Oligonucleotide Analogues," International Publication No. WO 98/39352; and Wengel et al., "Oligonucleotide Analogues," International Publication No. WO 99/14226.) Any nucleic acid analog is contemplated by the present invention provided the modified oligonucleotide can hybridize to a target nucleic acid under stringent hybridization assay conditions or amplification conditions. In the case of hybridization assay probes, the modified oligonucleotides must also be capable of preferentially hybridizing to the target nucleic acid under stringent hybridization assay conditions.

Oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As intended by this disclosure, an oligonucleotide does not consist of wild-type chromosomal DNA or the in vivo transcription products thereof. One use of an oligonucleotide is as a hybridization assay probe. Oligonucleotides may also be used as in vivo or in vitro therapeutic amplification primers or as antisense agents to block or inhibit gene transcription or translation in diseased, infected, or pathogenic cells.

By "hybridization assay probe" or "probe" is meant an oligonucleotide having a base sequence sufficiently complementary to its target nucleic acid sequence to form a probe:target hybrid stable for detection under stringent hybridization assay conditions. As would be understood by someone having ordinary skill in the art, a probe is an isolated nucleic acid molecule, or an analog thereof, in a form not found in nature without human intervention (e.g., recombined with foreign nucleic acid, isolated, or purified to some extent). The probes of this invention may have additional nucleosides or nucleobases outside of the targeted region so long as such nucleosides or nucleobases do not prevent hybridization under stringent hybridization conditions and, in the case of hybridization assay probes, do not prevent preferential hybridization to the target nucleic acid. A non-complementary sequence may also be included, such as a target capture sequence (generally a homopolymer tract, such as a poly-A, poly-T or poly-U tail), promoter sequence, a binding site for RNA transcription, a restriction endonuclease recognition site, or sequences which will confer a desired secondary or tertiary structure, such as a catalytic active site or a hairpin structure, which can be used to facilitate detection and/or amplification. Probes of a defined sequence may be produced by techniques known to those of ordinary skill in the art, such as by chemical synthesis, and by in vitro or in vivo expression from recombinant nucleic acid molecules.

By "stable" or "stable for detection" is meant that the temperature of a reaction mixture is at least 2° C. below the melting temperature of a nucleic acid duplex. The temperature of the reaction mixture is more preferably at least 5° C. below the melting temperature of the nucleic acid duplex, and even more preferably at least 10° C. below the melting temperature of the reaction mixture.

By "substantially homologous," "substantially corresponding" or "substantially corresponds" is meant that the subject oligonucleotide has a base sequence containing an at least 10 contiguous base region that is at least 80% homologous, preferably at least 90% homologous, and most preferably 100% homologous to an at least 10 contiguous base region present in a reference base sequence (excluding RNA and DNA equivalents). (Those skilled in the art will readily appreciate modifications that could be made to the hybridization assay conditions at various percentages of homology to permit hybridization of the oligonucleotide to the target sequence while preventing unacceptable levels of non-specific hybridization.) The degree of similarity is determined by comparing the order of nucleobases making up the two sequences and does not take into consideration other structural differences which may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0 to 2 base differences.

By "substantially complementary" is meant that the subject oligonucleotide has a base sequence containing an at least 10 contiguous base region that is at least 80% complementary, preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0 to 2 base mismatches.

By "RNA and DNA equivalents" is meant RNA and DNA molecules having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "hybridization" is meant the ability of two completely or partially complementary nucleic acid strands to come together under specified hybridization assay conditions in a parallel or preferably antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., ROGER L. P. ADAMS ET AL., THE BIOCHEMISTRY OF THE NUCLEIC ACIDS (11$^{th}$ ed. 1992).)

By "preferentially hybridize" is meant that under stringent hybridization assay conditions, hybridization assay probes can hybridize to their target nucleic acids to form stable probe:target hybrids indicating the presence of at least one organism of interest, and there is not formed a sufficient number of stable probe:non-target hybrids to indicate the presence of non-targeted organisms, especially phylogenetically closely related organisms. Thus, the probe hybridizes to target nucleic acid to a sufficiently greater extent than to non-target nucleic acid to enable one having ordinary skill in the art to accurately detect the presence (or absence) of nucleic acid derived from *Cryptosporidium* or *Cryptosporidium parvum*, as appropriate, and distinguish its presence from that of a phylogenetically closely related organism in a test sample. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. Preferably, there is at least a 10-fold difference between target and non-target hybridization signals in a test sample, more preferably at least a 100-fold difference, and most preferably at least a 1.000-fold difference. Preferably, non-target hybridization signals in a test sample are no more than the background signal level.

By "stringent hybridization assay conditions," "hybridization assay conditions," "stringent hybridization conditions," or "stringent conditions" is meant conditions permitting a hybridization assay probe to preferentially hybridize to a target nucleic acid (preferably rRNA or rDNA derived from *Cryptosporidium* or *Cryptosporidium parvum* organisms) and not to nucleic acid derived from a closely related non-target microorganism. Stringent hybridization assay conditions may vary depending upon factors including the GC content and length of the probe, the degree of similarity between the probe sequence and sequences of non-target sequences which may be present in the test sample, and the target sequence. Hybridization conditions include the temperature and the composition of the hybridization reagents or solutions. While the Examples section infra provides preferred hybridization assay conditions for detecting target nucleic acids derived from *Cryptosporidium* or *Cryptosporidium parvum* organisms using the probes of the present invention, other acceptable stringent conditions could be easily ascertained by someone having ordinary skill in the art.

By "consists essentially of" or "consisting essentially of," when used with reference to an oligonucleotide herein, is meant that the oligonucleotide has a base sequence substantially homologous to a specified base sequence and may have up to four additional bases and/or two bases deleted therefrom. Thus, these phrases contain both a sequence length limitation and a sequence variation limitation. Any additions or deletions are non-material variations of the specified base sequence which do not prevent the oligonucleotide from having its claimed property, such as being able to preferentially hybridize under stringent hybridization assay conditions to its target nucleic acid over non-target nucleic acids. The oligonucleotide may contain a base sequence substantially similar to a specified nucleic acid sequence without any additions or deletions. However, a probe or primer containing an oligonucleotide consisting essentially of (or which consists essentially of) a specified base sequence may include other nucleic acid molecules which do not participate in hybridization of the probe to the target nucleic acid and which do not affect such hybridization.

By "nucleic acid duplex," "duplex," "nucleic acid hybrid" or "hybrid" is meant a stable nucleic acid structure comprising a double-stranded, hydrogen-bonded region. Such hybrids include RNA:RNA, RNA:DNA and DNA:DNA duplex molecules and analogs thereof. The structure is sufficiently stable to be detectable by any known means, including means which do not require a probe associated label. For instance, the detection method may include a probe coated substrate which is optically active and sensitive to changes in mass at its surface. Mass changes result in different reflective and transmissive properties of the optically active substrate in response to light and serve to indicate the presence or amount of immobilized target nucleic acid. (This exemplary form of optical detection is disclosed by Nygren et al., "Devices and Methods for Optical Detection of Nucleic Acid Hybridization," U.S. Pat. No. 6,060,237.)

By "amplification primer" or "primer" is meant an oligonucleotide capable of hybridizing to a target nucleic acid and acting as a primer and/or a promoter template (e.g., for synthesis of a complementary strand, thereby forming a functional promoter sequence) for the initiation of nucleic acid synthesis. If the amplification primer is designed to initiate RNA synthesis, the primer may contain a base sequence which is non-complementary to the target sequence but which is recognized by an RNA polymerase such as a T7, T3 or SP6 RNA polymerase. An amplification primer may contain a 3' terminus which is modified to prevent or lessen the rate or amount of primer extension. (McDonough et al., "Methods of Amplifying Nucleic Acids Using Promoter-Containing Primer Sequence," U.S. Pat. No. 5,766,849, disclose primers and promoter-primers having modified or blocked 3'-ends.) While the amplification primers of the present invention may be chemically synthesized or derived from a vector, they are not naturally-occurring nucleic acid molecules.

By "nucleic acid amplification" or "target amplification" is meant increasing the number of nucleic acid molecules having at least one target nucleic acid sequence. Target amplification according to the present invention may be either linear or exponential, although exponential amplification is preferred.

By "amplification conditions" is meant conditions permitting nucleic acid amplification. While the Examples section infra provides preferred amplification conditions for amplifying target nucleic acid sequences derived from *Cryptosporidium* or *Cryptosporidium parvum* organisms using primers of the present invention in a transcription-based method of amplification, other acceptable amplification conditions could be easily ascertained by someone having ordinary skill in the art depending on the particular method of amplification employed.

By "antisense," "opposite sense" or "negative sense" is meant a nucleic acid molecule perfectly complementary to a reference, or sense, nucleic acid molecule.

By "sense," "same-sense" or "positive sense" is meant a nucleic acid molecule perfectly homologous to a reference nucleic acid molecule.

By "amplicon" is meant a nucleic acid molecule generated in a nucleic acid amplification reaction and which is derived from a target nucleic acid. An amplicon contains a target nucleic acid sequence which may be of the same or opposite sense as the target nucleic acid.

By "derived" is meant that the referred to nucleic acid is obtained directly from an organism or is the product of a nucleic acid amplification. Thus, a nucleic acid which is "derived" from an organism may be, for example, an antisense RNA molecule which does not naturally exist in the organism.

By "capture probe" is meant one or more oligonucleotides linked together which are capable of hybridizing to a target nucleic acid—in a region other than that targeted by a hybridization assay probe—and to an immobilized probe, thereby providing means for immobilizing and isolating the target nucleic acid in a test sample. The capture probe includes both a target binding region, which hybridizes to the target nucleic acid, and an immobilized probe binding region, which hybridizes to the immobilized probe. While the capture probe hybridizes to both the target nucleic acid and the immobilized probe under stringent conditions, the target binding and the immobilized probe binding regions of the capture probe may be designed to bind to their target sequences under different hybridization conditions. In this way, the capture probe may be designed so that it first hybridizes to the target nucleic acid under more favorable in solution kinetics before adjusting the conditions to permit hybridization of the immobilized probe binding region to the immobilized probe. The target binding and immobilized probe binding regions may be contained within the same oligonucleotide, directly adjoining each other or separated by one or more optionally modified nucleotides, or these regions may be joined to each other by means of a non-nucleotide linker.

By "immobilized probe" is meant an oligonucleotide for joining a capture probe to an immobilized support. The immobilized probe is joined either directly or indirectly to the solid support by a linkage or interaction which remains stable under the conditions employed to hybridize the capture probe to the target nucleic acid and to the immobilized probe, whether those conditions are the same or different. The immobilized probe facilitates separation of the bound target nucleic acid from unbound materials in a sample.

By "separating," "purifying" or "purified" is meant that one or more components of a sample contained in a sample-holding vessel are or have been physically removed from, or diluted in the presence of, one or more other sample components present in the vessel. Sample components which may be removed or diluted during a separating or purifying step include proteins, carbohydrates, lipids, inhibitors, non-target nucleic acids and unbound probe. With target capture procedures, target nucleic acids bound to immobilized capture probes are preferably retained in the sample during the separating or purifying step.

By "helper probe" or "helper oligonucleotide" is meant an oligonucleotide designed to hybridize to a target nucleic acid at a different locus than that of a hybridization assay probe, thereby either increasing the rate of hybridization of the probe to the target nucleic acid, increasing the melting temperature ($T_m$) of the probe:target hybrid, or both.

By "phylogenetically closely related" is meant that the organisms are closely related to each other in an evolutionary sense and therefore would have a higher total nucleic acid sequence homology than organisms that are more distantly related. Organisms occupying adjacent and next to adjacent positions on the phylogenetic tree are closely related. Organisms occupying positions farther away than adjacent or next to adjacent positions on the phylogenetic tree will still be closely related if they have significant total nucleic acid sequence homology.

By "genus-specific" is meant that the referred to probe is capable of preferentially hybridizing under stringent hybridization assay conditions to a target nucleic acid sequence present in nucleic acid derived from organisms belonging to at least two species of the genus *Cryptosporidium*.

By "species-specific" is meant that the referred to probe is capable of preferentially hybridizing under stringent hybridization assay conditions to a target nucleic acid sequence present in nucleic acid derived from organisms belonging to the species *Cryptosporidium parvum*.

B. Hybridization Conditions and Probe/Primer Design

Hybridization reaction conditions, most importantly the temperature of hybridization and the concentration of salt in the hybridization solution, can be selected to allow the hybridization assay probes or amplification primers of the present invention to preferentially hybridize to nucleic acids having a *Cryptosporidium* target nucleic sequence, and not to other non-target nucleic acids suspected of being present in a test sample. At decreased salt concentrations and/or increased temperatures (conditions of increased stringency) the extent of nucleic acid hybridization decreases as hydrogen bonding between paired nucleotide bases in the double-stranded hybrid molecule is disrupted. This process is known as "melting."

Generally speaking, the most stable hybrids are those having the largest number of contiguous, perfectly matched (i.e., hydrogen-bonded) nucleotide base pairs. Such hybrids would usually be expected to be the last to melt as the stringency of the hybridization conditions increases. However, a double-stranded nucleic acid region containing one or more mismatched, "non-canonical," or imperfect base pairs (resulting in weaker or non-existent base pairing at that position in the nucleotide sequence of a nucleic acid) may still be sufficiently stable under conditions of relatively high stringency to allow the nucleic acid hybrid to be formed and detected in a hybridization assay without cross-reacting with other, non-selected nucleic acids which may be present in a test sample.

Hence, depending on the degree of similarity between the nucleotide sequences of the target nucleic acid and those of non-target nucleic acids belonging to phylogenetically distinct, but closely-related organisms on one hand, and the degree of complementarity between the nucleotide sequences of a particular hybridization assay probe or amplification primer and those of the target and non-target nucleic acids on the other, one or more mismatches will not necessarily defeat the ability of an oligonucleotide contained in the probe or primer to hybridize to the target nucleic acid and not to non-target nucleic acids.

The hybridization assay probes of the present invention were chosen, selected, and/or designed to maximize the difference between the melting temperatures of the probe:target hybrid ($T_m$, defined as the temperature at which half of the potentially double-stranded molecules in a given reaction mixture are in a single-stranded, denatured state) and the $T_m$ of a mismatched hybrid formed between the probe and rRNA or rDNA of the phylogenetically most closely-related organisms expected to be present in the test sample, but not sought to be detected. While the unlabeled amplification primers and helper probes need not have such an extremely high degree of specificity as the hybridization assay probe to be useful in the present invention, they are designed in a similar manner to preferentially hybridize to one or more target nucleic acids over other nucleic acids under specified amplification or hybridization assay conditions.

To facilitate the identification of nucleic acid sequences to be used in the design of probes, nucleotide sequences from different organisms were first aligned to maximize homology. The nucleotide sequences used for this comparison were obtained from the GenBank database and had the following associated accession numbers: *Cryptosporidium parvum* (Accession Nos. L16996, L16997, L25642, AF040725 and AF015772), *Cryptosporidium muris* (Accession No. L19069), *Cryptosporidium baileyi* (Accession No. L19068), *Cryptosporidium wrairi* (Accession No. U11440), *Escherichia coli* (Accession No. Z83204), *Cyclospora cayetanensis* (Accession No. AF111183), *Sarcocystis hominis* (Accession No. AF006470), *Entamoeba histolytica* (Accession No. X64142) and *Eimeria praecox* (Accession No. U67120).

Within the rRNA molecule there is a close relationship between secondary structure (caused in part by intra-molecular hydrogen bonding) and function. This fact imposes restrictions on evolutionary changes in the primary nucleotide sequence causing the secondary structure to be maintained. For example, if a base is changed in one "strand" of a double helix (due to intra-molecular hydrogen bonding, both "strands" are part of the same rRNA molecule), a compensating substitution usually occurs in the primary sequence of the other "strand" in order to preserve complementarity (this is referred to as co-variance), and thus the necessary secondary structure. This allows two very different rRNA sequences to be aligned based both on the conserved primary sequence and also on the conserved secondary structure elements. Potential target sequences for the hybridization assay probes described herein were identified by noting variations in the homology of the aligned sequences.

The sequence evolution at each of the variable regions is mostly divergent. Because of the divergence, corresponding rRNA variable regions of more distant phylogenetic relatives of *Cryptosporidium* show greater differences from *Cryptosporidium* rRNA than do the rRNAs of phylogenetically closer relatives. Similarly, corresponding rRNA variable regions of more distant phylogenetic relatives of *Cryptosporidium parvum* show greater differences from *Cryptosporidium parvum* rRNA than do the rRNAs of phylogenetically closer relatives. Sufficient variation between *Cryptosporidium* (i.e., *Cryptosporidium parvum*, *Cryptosporidium muris*, *Cryptosporidium baileyi* and *Cryptosporidium wrairi*) and *Escherichia coli*, *Cyclospora cayetanensis*, *Sarcocystis hominis*, *Entamoeba histolytica* and *Eimeria praecox* was observed to identify preferred target sites and design hybridization assay probes useful for distinguishing *Cryptosporidium* organisms over non-*Cryptosporidium* organisms. Likewise, sufficient variation between *Cryptosporidium parvum* and *Cryptosporidium muris*, *Cryptosporidium baileyi* and *Cryptosporidium wrairi* was observed to identify preferred target sites and design hybridization assay probes useful for distinguishing *Cryptosporidium parvum* organisms over non-*Cryptosporidium parvum* organisms, especially the noted *Cryptosporidium* species.

We have identified sequences which vary between *Cryptosporidium parvum* and other *Cryptosporidium* species, and between members of the genus *Cryptosporidium* and other organisms, by comparative analysis of rRNA sequences published in the GenBank sequence database and, in the case of *Cryptosporidium parvum*, further determined and confirmed in the laboratory. Computers and computer programs which may be used or adapted for the purposes herein disclosed are commercially available. We observed sufficient similarity between *Cryptosporidium parvum*, *Cryptosporidium muris*, *Cryptosporidium baileyi* and Cryptosporidium wrairi to design the present Cryptosporidium probes. We also observed sufficient variation between these same organisms to design the present Cryptosporidium parvum probes.

Merely identifying putatively unique potential target nucleotide sequences does not guarantee that a functionally genus-specific or species-specific hybridization assay probe may be made to hybridize to Cryptosporidium or Cryptosporidium parvum rRNA or rDNA comprising that sequence. Various other factors will determine the suitability of a nucleic acid locus as a target site for genus-specific or species-specific probes. Because the extent and specificity of hybridization reactions such as those described herein are affected by a number of factors, manipulation of one or more of those factors will determine the exact sensitivity and specificity of a particular oligonucleotide, whether perfectly complementary to its target or not. The importance and effect of various assay conditions are known to those skilled in the art and are disclosed by Hogan, "Nucleic Acid Probes for Detection and/or Quantitation of Non-Viral Organisms," U.S. Pat. No. 5,840,488; Hogan et al., "Nucleic Acid Probes to Mycobacterium gordonae," U U.S. Pat. No. 5,216,143; and Kohne, "Method for Detection, Identification and Quantitation of Non-Viral Organisms," U.S. Pat. No. 4,851,330.

The desired temperature of hybridization and the hybridization solution composition (such as salt concentration, detergents and other solutes) can also greatly affect the stability of double-stranded hybrids. Conditions such as ionic strength and the temperature at which a probe will be allowed to hybridize to a target must be taken into account in constructing a genus-specific or species-specific probe. The thermal stability of hybrid nucleic acids generally increases with the ionic strength of the reaction mixture. On the other hand, chemical reagents which disrupt hydrogen bonds, such as formamide, urea, dimethyl sulfoxide and alcohols, can greatly reduce the thermal stability of the hybrids.

To maximize the specificity of a probe for its target, the subject probes of the present invention were designed to hybridize to their targets under conditions of high stringency. Under such conditions only single nucleic acid strands having a high degree of complementarity will hybridize to each other. Single nucleic acid strands without such a high degree of complementarity will not form hybrids. Accordingly, the stringency of the assay conditions determines the amount of complementarity which should exist between two nucleic acid strands in order to form a hybrid. Stringency is chosen to maximize the difference in stability between the hybrid formed between the probe and the target nucleic acid and potential hybrids between the probe and any non-target nucleic acids present in a test sample.

Proper specificity may be achieved by minimizing the length of the hybridization assay probe having perfect complementarity to sequences of non-target organisms, by avoiding G and C rich regions of complementarity to non-target nucleic acids, and by constructing the probe to contain as many destabilizing mismatches to non-target sequences as possible. Whether a probe is appropriate for detecting only a specific type of organism depends largely on the thermal stability difference between probe:target hybrids versus probe:non-target hybrids. In designing probes, the differences in these $T_m$ values should be as large as possible (preferably 2-5° C. or more). Manipulation of the $T_m$ can be accomplished by changes to probe length and probe composition (e.g., GC content versus AT content).

In general, the optimal hybridization temperature for oligonucleotide probes is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the $T_m$. Increasing the percentage of G and C also increases the $T_m$ because G-C base pairs exhibit additional hydrogen bonding and therefore greater thermal stability than A-T base pairs. Such considerations are known in the art. (See, e.g., J. SAMBROOK ET AL., MOLECULAR CLONING: A LABORATORY MANUAL, ch. 11 (2d ed. 1989).)

A preferred method to determine $T_m$ measures hybridization using the well known Hybridization Protection Assay (HPA) disclosed by Arnold et al., "Homogenous Protection Assay," U.S. Pat. No. 5,283,174. The $T_m$ can be measured using HPA in the following manner. Probe molecules are labeled with an acridinium ester and permitted to form probe:target hybrids in a lithium succinate buffer (0.1 M lithium succinate buffer, pH 4.7, 20 mM EDTA, 15 mM aldrithiol-2, 1.2 M LiCl, 3% (v/v) ethanol absolute, 2% (w/v) lithium lauryl sulfate) using an excess amount of target. Aliquots of the solution containing the probe:target hybrids are then diluted in the lithium succinate buffered solution and incubated for five minutes at various temperatures starting below that of the anticipated $T_m$ (typically 55° C.) and increasing in 2-5° C. increments. This solution is then diluted with a mild alkaline borate buffer (600 mM boric acid, 240 mM NaOH, 1% (v/v) TRITON® X-100, pH 8.5) and incubated at an equal or lower temperature (for example 50° C.) for ten minutes.

Under these conditions the acridinium ester attached to the single-stranded probe is hydrolyzed, while the acridinium ester attached to hybridized probe is relatively protected from hydrolysis. Thus, the amount of acridinium ester remaining after hydrolysis treatment is proportional to the number of hybrid molecules. The remaining acridinium ester can be measured by monitoring the chemiluminescence produced from the remaining acridinium ester by adding hydrogen peroxide and alkali to the solution. Chemiluminescence can be measured in a luminometer, such as a LEADER® 450i luminometer (Gen-Probe Incorporated, San Diego, Calif.; Cat. No. 3200i). The resulting data is plotted as percent of maximum signal (usually from the lowest temperature) versus temperature. The $T_m$ is defined as the temperature at which 50% of the maximum signal remains. In addition to the method above, $T_m$ may be determined by isotopic methods known to those skilled in the art (see, e.g., U.S. Pat. No. 5,840,488).

It should be noted that the $T_m$ for a given hybrid varies depending on the nature of the hybridization solution used. Factors such as the salt concentration, detergents, and other solutes can affect hybrid stability during thermal denaturation (see, e.g., SAMBROOK ET AL., supra, ch. 11). Conditions such as ionic strength and the temperature at which a probe will be allowed to hybridize to target should be taken into account in probe construction. (The thermal stability of a hybrid nucleic acid increases with the ionic strength of the reaction mixture.) On the other hand, chemical reagents that disrupt hydrogen bonds, such as formamide, urea, dimethyl sulfoxide and alcohols, can greatly reduce hybrid thermal stability.

To ensure specificity of a hybridization assay probe for its target, it is preferable to design probes which hybridize only to target nucleic acid under conditions of high stringency. Only highly complementary sequences will form hybrids under conditions of high stringency. Accordingly, the stringency of the assay conditions determines the amount of complementarity needed between two sequences in order for a stable hybrid to form. Stringency should be chosen to maximize the difference in stability between the probe:target hybrid and potential probe:non-target hybrids.

Examples of specific stringent hybridization conditions are provided in the Examples section infra. Of course, alternative stringent hybridization conditions could be determined by those of ordinary skill in the art based on the present disclosure. (See, e.g., SAMBROOK ET AL., supra, ch. 11.)

The length of the target nucleic acid sequence region and, accordingly, the length of the probe sequence can also be important. In some cases, there may be several sequences from a particular region, varying in location and length, which may be used to design probes with the desired hybridization characteristics. In other cases, one probe may be significantly better with regard to specificity than another which differs from it merely by a single base. While it is possible for nucleic acids that are not perfectly complementary to hybridize, the longest stretch of perfectly complementary bases, as well as the base compositions, will generally determine hybrid stability.

Regions of rRNA known to form strong internal structures inhibitory to hybridization are less preferred target regions, especially in assays where helper probes described infra are not used. Likewise, probes with extensive self-complementarity are generally to be avoided, with specific exceptions being discussed below. If a strand is wholly or partially involved in an intramolecular or intermolecular hybrid, it will be less able to participate in the formation of a new intermolecular probe:target hybrid without a change in the reaction conditions. Ribosomal RNA molecules are known to form very stable intramolecular helices and secondary structures by hydrogen bonding. By designing a probe to a region of the target nucleic acid which remains substantially single-stranded under hybridization conditions, the rate and extent of hybridization between probe and target may be increased.

A genomic ribosomal nucleic acid (rDNA) target occurs naturally in a double-stranded form, as does the product of the polymerase chain reaction (PCR). These double-stranded targets are naturally inhibitory to hybridization with a probe and require denaturation prior to hybridization. Appropriate denaturation and hybridization conditions are known in the art (see, e.g., Southern, E. M., *J. Mol. Biol.*, 98:503 (1975)).

A number of formulae are available which will provide an estimate of the melting temperature for perfectly matched oligonucleotides to their target nucleic acids. One such formula is the following:

$$T_m = 81.5 \pm 16.6(\log_{10}[Na^+]) + 0.41(\text{fraction } G+C) - (600/N)$$

(where N=the length of the oligonucleotide in number of nucleotides) provides a good estimate of the $T_m$ for oligonucleotides between 14 and 60 to 70 nucleotides in length. From such calculations, subsequent empirical verification or "fine tuning" of the $T_m$ may be made using screening techniques well known in the art. For further information on hybridization and oligonucleotide probes reference may be made to SAMBROOK ET AL., supra, ch. 11. This reference, among others well known in the art, also provides estimates of the effect of mismatches on the $T_m$ of a hybrid. Thus, from the known nucleotide sequence of a given region of the ribosomal RNA (or rDNA) of two or more organisms, oligonucleotides may be designed which will distinguish these organisms from one another.

C. Nucleic Acid Amplification

Preferably, the amplification primers of the present invention are oligodeoxynucleotides and are sufficiently long to be used as a substrate for the synthesis of extension products by a nucleic acid polymerase. Optimal primer length should take into account several factors, including the temperature of reaction, the structure and base composition of the primer, and how the primer is to be used. For example, for optimal specificity the oligonucleotide primer generally should be at least 12 bases in length, depending on the complexity of the target nucleic acid sequence. If such specificity is not essential, shorter primers may be used. In such a case, it may be desirable to carry out the reaction at cooler temperatures in order to form stable hybrid complexes with the template nucleic acid.

Useful guidelines for designing amplification primers and hybridization assay probes with desired characteristics are described infra in the section entitled "Preparation of Oligonucleotides." Optimal sites for amplifying and probing contain at least two, and preferably three, conserved regions of *Cryptosporidium* or *Cryptosporidium parvum* nucleic acid. These regions are about 15 to 350 bases in length, and preferably between about 15 and 150 bases in length.

The degree of amplification observed with a set of amplification primers (primers and/or promoter-primers) depends on several factors, including the ability of the primers to hybridize to their specific target sequences and their ability to be extended or copied enzymatically. While amplification primers of different lengths and base compositions may be used, amplification primers preferred in this invention have target binding regions of 18 to 40 bases with a predicted $T_m$ to target of about 42° C.

Parameters affecting probe hybridization, such as $T_m$, complementarity and secondary structure of the target sequence, also affect amplification primer hybridization and therefore performance of the amplification primers. The degree of non-specific extension (primer-dimer or non-target copying) can also affect amplification efficiency. Thus, amplification primers are selected to have low self-complementarity or cross-complementarity, particularly at the 3' ends of their sequences. Notwithstanding, we note that the "signal primers" described infra could be modified to include regions of self-complementarity, thereby transforming them into "Molecular Torch" or "Molecular Beacon" signal primers, such as these terms are defined below. Lengthy homopolymer runs and high GC content are avoided to reduce spurious primer extension. Computer programs are available to aid in this aspect of the design, including Oligo Tech® analysis software which is available from Oligo Therapeutics, Inc. and can be accessed on the World Wide Web at www.oligosetc.com/OligoTech.html using a hypertext transfer protocol (http) in the URL.

A nucleic acid polymerase used in conjunction with the amplification primers of the present invention refers to a chemical, physical or biological agent which incorporates either ribonucleotides or deoxyribonucleotides, or both, into a nucleic acid polymer, or strand, in a template-dependent manner. Examples of nucleic acid polymerases include DNA-directed DNA polymerases, RNA-directed DNA polymerases, and RNA-directed RNA polymerases. DNA polymerases bring about nucleic acid synthesis in a template-dependent manner and in a 5' to 3' direction. Because of the typical anti-parallel orientation of the two strands in a double-stranded nucleic acid, this direction is from a 3' region on the template to a 5' region on the template. Examples of DNA-directed DNA polymerases include *E. coli* DNA polymerase I, the thermostable DNA polymerase from *Thermus aquaticus* (Taq), and the large fragment of DNA polymerase I from *Bacillus stearothermophilus* (Bst). Examples of RNA directed DNA polymerases include various retroviral reverse transcriptases, such as Moloney murine leukemia virus (MMLV) reverse transcriptase or avian myeloblastosis virus (AMV) reverse transcriptase.

During most nucleic acid amplification reactions, a nucleic acid polymerase adds nucleotide residues to the 3' end of the primer using the target nucleic acid as a template, thus synthesizing a second nucleic acid strand having a nucleotide sequence partially or completely complementary to a region of the target nucleic acid. In many nucleic acid amplification reactions, the two strands comprising the resulting double-stranded structure must be separated by chemical or physical means in order to allow the amplification reaction to proceed. Alternatively, the newly-synthesized template strand may be made available for hybridization with a second primer or promoter-primer by other means, such as through strand displacement or the use of a nucleolytic enzyme which digests part or all of the original target strand. In this way the process may be repeated through a number of cycles, resulting in a large increase in the number of nucleic acid molecules having the target nucleotide sequence.

Either the first or second amplification primer, or both, may be a promoter-primer. (In some applications, the amplification primers may only consist of promoter-primers which are complementary to the sense strand, as disclosed by Kacian et al., "Nucleic Acid Sequence Amplification Method, Composition and Kit," U.S. Pat. No. 5,554,516.) A promoter-primer usually contains an oligonucleotide that is not complementary to a nucleotide sequence present in the target nucleic acid molecule or primer extension product(s) (see Kacian et al., "Nucleic Acid Sequence Amplification Methods," U.S. Pat. No. 5,399,491, for a description of such oligonucleotides). These non-complementary sequences may be located 5' to the complementary sequences on the amplification primer and may provide a locus for initiation of RNA synthesis when made double-stranded through the action of a nucleic acid polymerase. The promoter thus provided may allow for the in vitro transcription of multiple RNA copies of the target nucleic acid sequence. It will be appreciated that when reference is made to a primer in this specification, such reference is intended to include the primer aspect of a promoter-primer as well, unless the context of the reference clearly indicates otherwise.

In some amplification systems (see, e.g., the amplification methods disclosed by Dattagupta et al, "Isothermal Strand Displacement Nucleic Acid Amplification," U.S. Pat. No. 6,087,133), the amplification primers may contain 5' non-complementary nucleotides which assist in strand displacement. Furthermore, when used in conjunction with a nucleic acid polymerase having 5' exonuclease activity, the amplification primers may have modifications at their 5' end to prevent enzymatic digestion. Alternatively, the nucleic acid polymerase may be modified to remove the 5' exonuclease activity, such as by treatment with a protease that generates an active polymerase fragment with no such nuclease activity. In such a case the primers need not be modified at their 5' ends.

1. Preparation of Oligonucleotides

The oligonucleotide primers and probes of the present invention can be readily prepared by methods known in the art. Preferably, the oligonucleotides are synthesized using solid phase methods. For example, Caruthers describes using standard phosphoramidite solid-phase chemistry to join nucleotides by phosphodiester linkages. (See Caruthers, M. H., et al., *Methods Enzymol.*, 154:287 (1987).) Automated solid-phase chemical synthesis using cyanoethyl phosphoramidite precursors has been described by Barone. (See Barone, A. D., et al., *Nucleic Acids Res.*, 12(10):4051 (1984).) Likewise, Batt, "Method and Reagent for Sulfurization of Organophosphorous Compounds," U.S. Pat. No. 5,449,769, discloses a procedure for synthesizing oligonucleotides containing phosphorothioate linkages. In addition, Riley et al., "Process for the Purification of Oligomers," U.S. Pat. No. 5,811,538, disclose the synthesis of oligonucleotides having different linkages including methylphosphonate linkages. Moreover, methods for the organic synthesis of oligonucleotides are known to those of skill in the art and are described in, for example, SAMBROOK ET AL., supra, ch. 10.

Following synthesis and purification of a particular oligonucleotide, several different procedures may be utilized to purify and control the quality of the oligonucleotide. Suitable procedures include polyacrylamide gel electrophoresis or high pressure liquid chromatography. Both of these procedures are well known to those skilled in the art.

All of the oligonucleotides of the present invention, whether hybridization assay probes, amplification primers or helper probes, may be modified with chemical groups to enhance their performance or to facilitate the characterization of amplification products.

For example, backbone-modified oligonucleotides such as those having phosphorothioate, methylphosphonate, 2'-O-alkyl or peptide groups which render the oligonucleotides resistant to the nucleolytic activity of certain polymerases or to nuclease enzymes may allow the use of such enzymes in an amplification or other reaction. Another example of a modification involves using non-nucleotide linkers (see Arnold et al., "Non-Nucleotide Linking Reagents for Nucleotide Probes," U.S. Pat. No. 6,031,091.) incorporated between nucleotides in the nucleic acid chain of a probe or primer, and which do not prevent hybridization of a probe or hybridization and elongation of a primer. The oligonucleotides of the present invention may also contain mixtures of the desired modified and natural nucleotides.

The 3' end of an amplification primer may be modified or blocked to prevent or inhibit initiation of DNA synthesis, as disclosed by Kacian et al. in U.S. Pat. No. 5,554,516. The 3' end of the primer can be modified in a variety of ways well known in the art. By way of example, appropriate modifications to a primer can include the addition of ribonucleotides, 3' deoxynucleotide residues (e.g., cordycepin), 2',3'-dideoxynucleotide residues, modified nucleotides such as phosphorothioates, and non-nucleotide linkages such as those disclosed by Arnold et al. in U.S. Pat. No. 6,031,091 or alkanediol modifications (see Wilk et al., *Nucleic Acids Res.*, 18:2065 (1990)), or the modification may simply consist of a region 3' to the priming sequence that is non-complementary to the target nucleic acid sequence. Additionally, a mixture of different 3' blocked primers or of 3' blocked and unblocked primers may increase the efficiency of nucleic acid amplification, as described therein.

As disclosed above, the 5' end of primers may be modified to be resistant to the 5'-exonuclease activity present in some nucleic acid polymerases. Such modifications can be carried out by adding a non-nucleotide group to the terminal 5' nucleotide of the primer using techniques such as those disclosed by Arnold et al. in U.S. Pat. No. 6,031,091.

Once synthesized, a selected oligonucleotide may be labeled by any of several well known methods (see, e.g., SAMBROOK, supra, ch. 10). Useful labels include radioisotopes as well as non-radioactive reporting groups. Isotopic labels include $^3$H, $^{35}$S, $^{32}$P, $^{125}$I, $^{57}$Co and $^{14}$C. Isotopic labels can be introduced into the oligonucleotide by techniques known in the art such as nick translation, end labeling, second strand synthesis, the use of reverse transcription, and by chemical methods. When using radiolabeled probes, hybridization can be detected by autoradiography, scintillation counting or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as disclosed by Arnold et al. in U.S. Pat. No. 6,031,091. Non-isotopic labels include fluorescent molecules (individual labels or combinations of labels such as the fluorescence resonance energy transfer (FRET) pairs disclosed by Tyagi et al., "Detectably Labeled Dual Conformation Oligonucleotide Probes, Assays and Kits," U.S. Pat. No. 5,925,517), chemiluminescent molecules, enzymes, cofactors, enzyme substrates, haptens or other ligands.

With the hybridization assay probes of the present invention, the probes are preferably labeled by means of a non-nucleotide linker with an acridinium ester. Acridinium ester labeling may be performed as disclosed by Arnold et al., "Acridinium Ester Labelling and Purification of Nucleotide Probes," U.S. Pat. No. 5,185,439.

2. Amplification of *Cryptosporidium* Ribosomal Nucleic Acid

The amplification primers of the present invention are directed to regions of 18S ribosomal nucleic acid derived from *Cryptosporidium* or *Cryptosporidium parvum* organisms. These amplification primers may flank, overlap or be contained within at least one of the target nucleic acid sequences of a hybridization assay probe (or its complement) used to detect the presence of *Cryptosporidium* or *Cryptosporidium parvum* organisms in a nucleic acid amplification assay. As indicated above, the amplification primers may also include non-complementary bases at their 5' ends comprising a promoter sequence able to bind an RNA polymerase and direct RNA transcription using the target nucleic acid as a template. A T7 promoter sequence, such as SEQ ID NO:69, may be used.

Amplification primers of the present invention are capable of amplifying a target nucleic acid sequence present in nucleic acid derived from *Cryptosporidium* organisms under amplification conditions. These amplification primers comprise an oligonucleotide having or substantially corresponding to the base sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67 or SEQ ID NO:68.

Alternatively, amplification primers of the present invention comprise an oligonucleotide which, when contacted with a nucleic acid polymerase under amplification conditions, will bind to or cause extension through a nucleic acid region having a base sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67 or SEQ ID NO:68.

In one preferred embodiment, a set of at least two amplification primers for amplifying *Cryptosporidium* nucleic acid is provided which includes: (i) a first amplification primer comprising an oligonucleotide having or substantially corresponding to the base sequence of SEQ ID NO:45, SEQ ID NO:51, SEQ ID NO:57 or SEQ ID NO:63; and (ii) a second amplification primer comprising an oligonucleotide having or substantially corresponding to the base sequence of SEQ ID NO:47, SEQ ID NO:53, SEQ ID NO:59 or SEQ ID NO:65. Preferably, the first amplification primer comprises an oligonucleotide having or substantially corresponding to the base sequence of SEQ ID NO:45, and the second amplification primer comprises an oligonucleotide having or substantially corresponding to the base sequence of SEQ ID NO:59.

In another preferred embodiment, a set of at least two amplification primers for amplifying *Cryptosporidium* nucleic acid is provided which includes: (i) a first amplification primer comprising an oligonucleotide having or substantially corresponding to the base sequence of SEQ ID NO:45, SEQ ID NO:51, SEQ ID NO:57 or SEQ ID NO:63; and (ii) a second amplification primer comprising an oligonucleotide having or substantially corresponding to the base sequence of SEQ ID NO:48, SEQ ID NO:54, SEQ ID NO:60 or SEQ ID NO:66. Preferably, the first amplification primer comprises an oligonucleotide having or substantially corresponding to the base sequence of SEQ ID NO:45, and the second amplification primer comprises an oligonucleotide having or substantially corresponding to the base sequence of SEQ ID NO:60.

In yet another preferred embodiment, a set of at least two amplification primers for amplifying *Cryptosporidium* nucleic acid is provided which includes: (i) a first amplification primer comprising an oligonucleotide having or substantially corresponding to the base sequence of SEQ ID NO:46, SEQ ID NO:52, SEQ ID NO:58 or SEQ ID NO:64; and (ii) a second amplification primer comprising an oligonucleotide having or substantially corresponding to the base sequence of SEQ ID NO:48, SEQ ID NO:54, SEQ ID NO:60 or SEQ ID NO:66. Preferably, the first amplification primer comprises an oligonucleotide having or substantially corresponding to the base sequence of SEQ ID NO:46, and the second amplification primer comprises an oligonucleotide having or substantially corresponding to the base sequence of SEQ ID NO:60.

In still another preferred embodiment, a set of at least two amplification primers for amplifying *Cryptosporidium* nucleic acid is provided which includes: (i) a first amplification primer comprising an oligonucleotide having or substantially corresponding to the base sequence of SEQ ID NO:46, SEQ ID NO:52, SEQ ID NO:58 or SEQ ID NO:64; and (ii) a second amplification primer comprising an oligonucleotide having or substantially corresponding to the base sequence of SEQ ID NO:47, SEQ ID NO:53, SEQ ID NO:59 or SEQ ID NO:65. Preferably, the first amplification primer comprises an oligonucleotide having or substantially corresponding to the base sequence of SEQ ID NO:46, and the second amplification primer comprises an oligonucleotide having or substantially corresponding to the base sequence of SEQ ID NO:59.

In a further preferred embodiment, a set of at least two amplification primers for amplifying *Cryptosporidium* nucleic acid is provided which includes: (i) a first amplification primer comprising an oligonucleotide having or substantially corresponding to the base sequence of SEQ ID NO:49, SEQ ID NO:55, SEQ ID NO:61 or SEQ ID NO:67; and (ii) a second amplification primer comprising an oligonucleotide having or substantially corresponding to the base sequence of SEQ ID NO:50, SEQ ID NO:56, SEQ ID NO:62 or SEQ ID NO:68. Preferably, the first amplification primer comprises an oligonucleotide having or substantially corresponding to the base sequence of SEQ ID NO:49, and the second amplification primer comprises an oligonucleotide having or substantially corresponding to the base sequence of SEQ ID NO:62.

Amplification primers of the present invention may have modifications, such as blocked 3' and/or 5' termini (as discussed above) or sequence additions including, but not limited to, a specific nucleotide sequence recognized by an RNA polymerase (e.g., the promoter sequence for T7, T3 or SP6 RNA polymerase), a sequence which enhances initiation or elongation of RNA transcription by an RNA polymerase, or a sequence which may provide for intra-molecular base pairing and encourage the formation of secondary or tertiary nucleic acid structures.

Amplification primers are used in a nucleic acid amplification procedure, such as the polymerase chain reaction (PCR), transcription-mediated amplification (TMA), nucleic acid sequence-based amplification (NASBA), self-sustained sequence replication (3SR), ligase chain reaction (LCR), strand displacement amplification (SDA), and Loop-Mediated Isothermal Amplification (LAMP), each of which is well known in the art. See, e.g., Mullis, "Process for Amplifying Nucleic Acid Sequences," U.S. Pat. No. 4,683,202; Erlich et al., "Kits for Amplifying and Detecting Nucleic Acid Sequences," U.S. Pat. No. 6,197,563; Walker et al., *Nucleic Acids Res.*, 20:1691-1696 (1992); Fahy et al., "Self-sustained Sequence Replication (3SR): An Isothermal Transcription-Based Amplification System Alternative to PCR," *PCR Methods and Applications*, 1:25-33 (1991); Kacian et al., U.S. Pat. No. 5,399,491; Kacian et al., "Nucleic Acid Sequence Amplification Methods," U.S. Pat. No. 5,480,784; Davey et al., "Nucleic Acid Amplification Process," U.S. Pat. No. 5,554,517; Birkenmeyer et al., "Amplification of Target Nucleic Acids Using Gap Filling Ligase Chain Reaction," U.S. Pat. No. 5,427,930; Marshall et al., "Amplification of RNA Sequences Using the Ligase Chain Reaction," U.S. Pat. No. 5,686,272; Walker, "Strand Displacement Amplification," U.S. Pat. No. 5,712,124; Notomi et al., "Process for Synthesizing Nucleic Acid," European Patent Application No. 1 020 534 A1; Dattagupta et al., "Isothermal Strand Displacement Amplification," U.S. Pat. No. 6,214,587; and HELEN H. LEE ET AL., NUCLEIC ACID AMPLIFICATION TECHNOLOGIES: APPLICATION TO DISEASE DIAGNOSIS (1997). Any other amplification procedure which meets the definition of "nucleic acid amplification" supra is also contemplated by the inventors.

Amplification primers of the present invention are preferably unlabeled but may include one or more reporter groups to facilitate detection of a target nucleic acid in combination with or exclusive of a hybridization assay probe. A wide variety of methods are available to detect an amplified target sequence. For example, the nucleotide substrates or the primers can include a detectable label which is incorporated into newly synthesized DNA. The resulting labeled amplification product is then generally separated from the unused labeled nucleotides or primers and the label is detected in the separated product fraction. (See, e.g., Wu, "Detection of Amplified Nucleic Acid Using Secondary Capture Oligonucleotides and Test Kit," U.S. Pat. No. 5,387,510.)

A separation step is not required, however, if the primer is modified by, for example, linking it to two dyes which form a donor/acceptor dye pair. The modified primer can be designed so that the fluorescence of one dye pair member remains quenched by the other dye pair member, so long as the primer does not hybridize to target nucleic acid, thereby physically separating the two dyes. Moreover, the primer can be further modified to include a restriction endonuclease recognition site positioned between the two dyes so that when a hybrid is formed between the modified primer and target nucleic acid, the restriction endonuclease recognition site is rendered double-stranded and available for cleavage or nicking by an appropriate restriction endonuclease. Cleavage or nicking of the hybrid then separates the two dyes, resulting in a change in fluorescence due to decreased quenching which can be detected as an indication of the presence of the target organism or organisms in the test sample. This type of modified primer, referred to as a "signal primer," is disclosed by Nadeau et al., "Detection of Nucleic Acids by Fluorescence Quenching," U.S. Pat. No. 6,054,279.

Substances which can serve as useful detectable labels are well known in the art and include radioactive isotopes, fluorescent molecules, chemiluminescent molecules, chromophores, as well as ligands such as biotin and haptens which, while not directly detectable, can be readily detected by a reaction with labeled forms of their specific binding partners, e.g., avidin and antibodies, respectively.

Another approach is to detect the amplification product by hybridization with a detectably labeled oligonucleotide probe and measuring the resulting hybrids in any conventional manner. In particular, the product can be assayed by hybridizing a chemiluminescent acridinium ester-labeled oligonucleotide probe to the target sequence, selectively hydrolyzing the acridinium ester present on unhybridized probe, and measuring the chemiluminescence produced from the remaining acridinium ester in a luminometer. (See, e.g., U.S. Pat. No. 5,283,174 and NORMAN C. NELSON ET AL., NONISOTOPIC PROBING, BLOTTING, AND SEQUENCING, ch. 17 (Larry J. Kricka ed., 2d ed. 1995).)

D. Hybridization Assay Probes to *Cryptosporidium* Ribosomal Nucleic Acid

This embodiment of the invention relates to novel hybridization assay probes. Hybridization is the association of two single strands of complementary nucleic acid to form a hydrogen bonded double strand. A nucleic acid sequence able to hybridize to a nucleic acid sequence sought to be detected ("target sequence") can serve as a probe for the target sequence. Hybridization may occur between complementary nucleic acid strands, including DNA/DNA, DNA/RNA, and RNA/RNA. Two single strands of deoxyribo-(DNA) or ribo-(RNA) nucleic acid, formed from nucleotides (including the bases adenine (A), cytosine (C), thymidine (T), guanine (G), uracil (U), inosine (I), and analogs thereof), may hybridize to form a double-stranded structure in which the two strands are held together by hydrogen bonds between pairs of complementary bases. Generally, A is hydrogen-bonded to T or U, while G is hydrogen-bonded to C. At any point along the hybridized strands, therefore, the classical base pairs AT or AU, TA or UA, GC, or CG may be found. Thus, when a first single strand of nucleic acid contains sufficient contiguous complementary bases to a second, and those two strands are brought together under conditions that will promote their hybridization, double-stranded nucleic acid will result. Under appropriate conditions, DNA/DNA, RNA/DNA, or RNA/RNA hybrids may be formed.

The rate and extent of hybridization is influenced by a number of factors. For instance, it is implicit that if one of the two strands is wholly or partially involved in a hybrid, it will be less able to participate in the formation of a new hybrid. By designing a probe so that a substantial portion of the sequence of interest is single-stranded, the rate and extent of hybridization may be greatly increased. Also, if the target is an integrated genomic sequence it will naturally occur in a double-stranded form, as is the case with a product of PCR. These double-stranded targets are naturally inhibitory to hybridization with a probe and require denaturation prior to the hybridization step. In addition, there can be intra-molecular and inter-molecular hybrids formed within a probe if there is sufficient self-complementarity. Regions of the nucleic acid which are known to form strong internal structures inhibitory to hybridization are less preferred. Examples of such structures include hairpin loops. Likewise, probes with extensive self-complementarity generally should be avoided. All these undesirable structures can be avoided through careful probe design, and commercial computer programs are available to search for these types of interactions, such as the Oligo Tech® analysis software available from Oligo Therapeutics, Inc.

In some applications, probes exhibiting at least some degree of self-complementarity are desirable to facilitate detection of probe:target duplexes in a test sample without first requiring the removal of unhybridized probe prior to detection. By way of example, structures referred to as "Molecular Torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions (which may be fully or partially complementary) of the Molecular Torch melt, leaving the target binding domain available for hybridization to a target sequence when the predetermined hybridization assay conditions are restored. Molecular Torches are designed so that the target binding domain favors hybridization to the target sequence over the target closing domain. The target binding domain and the target closing domain of a Molecular Torch include interacting labels (e.g., luminescent/quencher) positioned so that a different signal is produced when the Molecular Torch is self-hybridized than when the Molecular Torch is hybridized to a target nucleic acid, thereby permitting detection of probe:target duplexes in a test sample in the presence of unhybridized probe having a viable label associated therewith. (Molecular Torches are disclosed by Becker et al., "Molecular Torches," U.S. application Ser. No. 09/346,551 and International Publication No. WO 00/01850, both of which enjoy common ownership herewith.)

Another example of a hybridization assay probe having self-complementarity is a structure commonly referred to as a "Molecular Beacon." Molecular Beacons include nucleic acid molecules having a target complement sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complement sequence separates the members of the affinity pair, thereby shifting the probe to an open confirmation. The shift to the open confirmation is detectable due to reduced interaction of the label pair, which may be, for example, a fluorophore and a quencher (e.g., DABCYL and EDANS). (Molecular Beacons are disclosed by Tyagi et al. in U.S. Pat. No. 5,925,517.)

The rate at which a probe hybridizes to its target is one measure of the thermal stability of the target secondary structure in the probe region. The standard measurement of hybridization rate is the $C_o t_{1/2}$, which is measured as moles of nucleotide per liter times seconds. Thus, it is the concentration of probe times the time at which 50% of maximal hybridization occurs at that concentration. This value is determined by hybridizing various amounts of probe to a constant amount of target for a fixed time. The $C_o t_{1/2}$ is found graphically by standard procedure. The probe:target hybrid melting temperature may be determined by isotopic methods well-known to those skilled in the art. The melting temperature ($T_m$) for a given hybrid will vary depending on the hybridization solution being used.

Thus, in a first aspect, the invention features hybridization assay probes able to distinguish *Cryptosporidium* nucleic acid from non-*Cryptosporidium* nucleic acid, by virtue of the ability of the probe to preferentially hybridize to *Cryptosporidium* nucleic acid under stringent hybridization assay conditions. Specifically, the *Cryptosporidium* probes contain an oligonucleotide having a base sequence that is substantially complementary to a target sequence present in nucleic acid derived from *Cryptosporidium* organisms. A *Cryptosporidium* probe of the present invention may detect less than all members of the genus *Cryptosporidium* which may be present in a test sample and still be characterized as a *Cryptosporidium* probe, provided the *Cryptosporidium* probe is capable of detecting the presence of at least two species belonging to the *Cryptosporidium* genus under stringent hybridization assay conditions.

In a related aspect, the invention describes hybridization assay probes able to distinguish *Cryptosporidium parvum* nucleic acid from non-*Cryptosporidium parvum* nucleic acid, by virtue of the ability of the probe to preferentially hybridize to *Cryptosporidium parvum* nucleic acid under stringent hybridization assay conditions. Specifically, the *Cryptosporidium parvum* probes contain an oligonucleotide having a base sequence that is substantially complementary to a target sequence present in nucleic acid derived from *Cryptosporidium parvum* organisms. A *Cryptosporidium parvum* probe of the present invention may detect less than all members of the species *Cryptosporidium parvum* which may be present in a test sample and still be characterized as a *Cryptosporidium parvum* probe, provided the *Cryptosporidium parvum* probe is capable of detecting the presence of at least one strain belonging to the *Cryptosporidium parvum* species under stringent hybridization assay conditions.

In the case of a hybridization assay, the length of the target nucleic acid sequence and, accordingly, the length of the probe sequence can be important. In some cases, there may be several sequences from a particular region, varying in location and length, which will yield probes with the desired hybridization characteristics. In other cases, one sequence may have better hybridization characteristics than another that differs merely by a single base. While it is possible for nucleic acids that are not perfectly complementary to hybridize, the longest stretch of perfectly homologous base sequence will normally primarily determine hybrid stability. While probes of different lengths and base composition may be used, the probes preferred in this invention have oligonucleotides that are up to 100 bases in length, more preferably from 12 to 50 bases in length, and even more preferably from 18 to 35 bases in length.

The hybridization assay probes include a base sequence that is substantially complementary to an 18S ribosomal RNA (rRNA), or the encoding DNA (rDNA), target sequence of *Cryptosporidium* or *Cryptosporidium parvum*. Thus, the probes are able to stably hybridize to a target sequence derived from a *Cryptosporidium* or *Cryptosporidium parvum* organism or organisms under stringent hybridization assay conditions. The hybridization assay probes may also have additional bases outside of the targeted nucleic acid region which may or may not be complementary to *Cryptosporidium*-derived or *Cryptosporidium parvum*-derived nucleic acid but which are not complementary to nucleic acid derived from a non-target organism which may be present in the test sample.

Probes (and primers) of the present invention may also be designed to include a capture tail comprised of a base sequence (distinct from the base sequence intended to hybridize to the target sequence) which can hybridize under predetermined hybridization conditions to a substantially complementary base sequence present in an immobilized oligonucleotide which is joined to a solid support. The immobilized oligonucleotide is preferably joined to a magnetically charged particle which can be isolated in a reaction vessel during a purification step after a sufficient period of time has passed for probe to hybridize to target nucleic acid. (An example of an instrument which can be used to perform such a purification step is disclosed by Acosta et al., "Assay Work Station," U.S. Pat. No. 6,254,826.) The probe is preferably designed so that the melting temperature of the probe:target hybrid is greater than the melting temperature of the probe:immobilized oligonucleotide hybrid. In this way, different sets of hybridization assay conditions can be employed to facilitate hybridization of the probe to the target nucleic acid prior to hybridization of the probe to the immobilized oligonucleotide, thereby maximizing the concentration of free probe and providing favorable liquid phase hybridization kinetics. This "two-step" target capture method is disclosed by Weisburg et al., "Two Step Hybridization and Capture of a Polynucleotide," U.S. Pat. No. 6,110,678. Other target capture schemes which could be readily adapted to the present invention are well known in the art and include, for example, those disclosed by Ranki et al., "Detection of Microbial Nucleic Acids by a One-Step Sandwich Hybridization Test," U.S. Pat. No. 4,486,539, and Stabinsky, "Methods and Kits for Performing Nucleic Acid Hybridization Assays," U.S. Pat. No. 4,751,177.

For *Cryptosporidium* probes, the terms "target nucleic acid sequence," "target nucleotide sequence," "target sequence" and "target region" all refer to a nucleic acid sequence present in *Cryptosporidium* rRNA or rDNA, or a sequence complementary thereto, which is not present in the nucleic acid of a closely related non-Cryptosporidium species. For *Cryptosporidium parvum* probes, the terms "target nucleic acid sequence," "target nucleotide sequence," "target sequence" and "target region" all refer to a nucleic acid sequence present in *Cryptosporidium parvum* rRNA or rDNA, or a sequence complementary thereto, which is not present in the nucleic of a closely related non-*Cryptosporidium parvum* species. Nucleic acids having nucleotide sequences complementary to a target sequence may be generated by target amplification techniques such as the polymerase chain reaction (PCR) or transcription-mediated amplification (TMA). (TMA is disclosed by, for example, Kacian et al. in U.S. Pat. No. 5,399,491, and Kacian et al, "Nucleic Acid Sequence Amplification Methods," U.S. Pat. No. 5,480,784.)

Organisms that might be expected to be present in a *Cryptosporidium*-containing test sample include, for example, *Escherichia coli, Cyclospora cayetanensis, Sarcocystis hominis, Entamoeba histolytica* and *Eimeria praecox*. This list of organisms is by no means intended to be fully representative of the organisms that the *Cryptosporidium* probes of the present invention can be used to distinguish over. In general, the *Cryptosporidium* probes of this invention can be used to distinguish *Cryptosporidium* nucleic acid from any non-*Cryptosporidium* nucleic acid that does not stably hybridize with the probe(s) under stringent hybridization conditions.

Organisms closely related to *Cryptosporidium parvum* include *Cryptosporidium muris, Cryptosporidium baileyi* and *Cryptosporidium wrairi*, although this list is by no means intended to be fully representative of the organisms that the *Cryptosporidium parvum* probes of the present invention can be used to distinguish over. In general, the *Cryptosporidium parvum* probes of this invention can be used to distinguish *Cryptosporidium parvum* nucleic acid from any non-*Cryptosporidium parvum* nucleic acid that does not stably hybridize with the probe(s) under stringent hybridization conditions.

A *Cryptosporidium* probe of the present invention preferably comprises an oligonucleotide having or substantially corresponding to the base sequence of SEQ ID NO:1, SEQ ID NO:2, SEQ ID NO:3 or SEQ ID NO:4. A *Cryptosporidium* probe comprising an oligonucleotide having or substantially corresponding to the base sequence of SEQ ID NO: 1 or SEQ ID NO:2 preferably includes an acridinium ester label joined to the probe by means of a non-nucleotide linker positioned between nucleotides 11 and 12 (reading 5' to 3') of SEQ ID NO:1 or SEQ ID NO:2. And a *Cryptosporidium* probe comprising an oligonucleotide having or substantially corresponding to the base sequence of SEQ ID NO:3 or SEQ ID NO:4 preferably includes an acridinium ester label joined to the probe by means of a non-nucleotide linker positioned between nucleotides 11 and 12 (reading 5' to 3') of SEQ ID NO:3 or SEQ ID NO:4. Joining the acridinium ester label to the probe may be carried out in accordance with the teachings of Arnold et al. in U.S. Pat. Nos. 5,185,439 and 6,031,091.

A *Cryptosporidium parvum* probe of the present invention preferably comprises an oligonucleotide having or substantially corresponding to the base sequence of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 or SEQ ID NO:20. One group of preferred *Cryptosporidium parvum* probes comprises an oligonucleotide having or substantially corresponding to the base sequence of SEQ ID NO:5, SEQ ID NO:9, SEQ ID NO:13 or SEQ ID NO:17, and preferably include an acridinium ester label joined to the probe by means of a non-nucleotide linker positioned between nucleotides 18 and 19 (reading 5' to 3') of SEQ ID NO:5 or SEQ ID NO:9 and between nucleotides 9 and 10 (reading 5' to 3') of SEQ ID NO:13 or SEQ ID NO:17. Another group of preferred *Cryptosporidium parvum* probes comprises an oligonucleotide having or substantially corresponding to the base sequence of SEQ ID NO:6, SEQ ID NO:10, SEQ ID NO:14 or SEQ ID NO:18, and preferably include an acridinium ester label joined to the probe by means of a non-nucleotide linker positioned between nucleotides 11 and 12 (reading 5' to 3') of SEQ ID NO:6 or SEQ ID NO:10 and between nucleotides 9 and 10 (reading 5' to 3') of SEQ ID NO:14 or SEQ ID NO:18. A further group of preferred *Cryptosporidium parvum* probes comprises an oligonucleotide having or substantially corresponding to the base sequence of SEQ ID NO:7, SEQ ID NO:11, SEQ ID NO:15 or SEQ ID NO:19, and preferably include an acridinium ester label joined to the probe by means of a non-nucleotide linker positioned between nucleotides 13 and 14 (reading 5' to 3') of SEQ ID NO:7 or SEQ ID NO:11 and between nucleotides 12 and 13 (reading 5' to 3') of SEQ ID NO:15 or SEQ ID NO:19. A final group of preferred *Cryptosporidium parvum* probes comprises an oligonucleotide having or substantially corresponding to the base sequence of SEQ ID NO:8, SEQ ID NO:12, SEQ ID NO:16 or SEQ ID NO:20, and preferably include an acridinium ester label joined to the probe by means of a non-nucleotide linker positioned between nucleotides 16 and 17 (reading 5' to 3') of SEQ ID NO:8 or SEQ ID NO:12 and between nucleotides 9 and 10 (reading 5' to 3') of SEQ ID NO:16 or SEQ ID NO:20. Joining the acridinium ester label to the probe may be carried out in accordance with the teachings of Arnold et al. in U.S. Pat. Nos. 5,185,439 and 6,031,091.

Thus, in one aspect of the present invention a *Cryptosporidium* hybridization assay probe is provided which is useful for determining whether *Cryptosporidium* organisms are present in a test sample. The probe comprises an oligonucleotide up to 100 bases in length which contains an at least 10 contiguous base region which is at least 80% complementary to an at least 10 contiguous base region present in a target nucleic acid sequence present in a target nucleic acid derived from *Cryptosporidium* organisms. The target sequence preferably has the base sequence of SEQ ID NO:1, SEQ ID NO:2, SEQ ID NO:3 or SEQ ID NO:4, and the probe preferentially hybridizes under stringent conditions to the target nucleic acid over nucleic acid derived from non-Cryptosporidium organisms present in the test sample.

Alternatively, the *Cryptosporidium* probe comprises an oligonucleotide up to 100 bases in length which contains an at least 10 contiguous base region which is at least 80% homologous to an at least 10 contiguous base region present in the base sequence of SEQ ID NO:1, SEQ ID NO:2, SEQ ID NO:3 or SEQ ID NO:4. The probe preferentially hybridizes under stringent conditions to the target nucleic acid over nucleic acid derived from non-*Cryptosporidium* organisms present in the test sample.

In another aspect of the present invention a *Cryptosporidium parvum* hybridization assay probe is provided which is useful for determining whether *Cryptosporidium parvum* organisms are present in a test sample. The probe comprises an oligonucleotide up to 100 bases in length which contains an at least 10 contiguous base region which is at least 80% complementary to an at least 10 contiguous base region present in a target nucleic acid sequence present in a target nucleic acid derived from *Cryptosporidium parvum* organisms. The target sequence preferably has the base sequence of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 or SEQ ID NO:20, and the probe preferentially hybridizes under stringent conditions to the target nucleic acid over nucleic acid derived from non-*Cryptosporidium parvum* organisms in the test sample.

Alternatively, the *Cryptosporidium parvum* probe comprises an oligonucleotide up to 100 bases in length which contains an at least 10 contiguous base region which is at least 80% homologous to an at least 10 contiguous base region present in the base sequence of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 or SEQ ID NO:20. The probe preferentially hybridizes under stringent conditions to the target nucleic acid over nucleic acid derived from non-*Cryptosporidium parvum* organisms present in the test sample.

Once synthesized, the probes may be labeled with a detectable label or reporter group by any well-known method. (See, e.g., SAMBROOK ET AL., supra, ch. 10.) The probe may be labeled with a detectable moiety such as a radioisotope, antigen or chemiluminescent moiety to facilitate detection of the target sequence. Useful labels include radioisotopes as well as non-radioactive reporting groups. Isotopic labels include $^3$H, $^{35}$S, $^{32}$P, $^{125}$I, $^{57}$Co and $^{14}$C. Isotopic labels can be introduced into an oligonucleotide by techniques known in the art such as nick translation, end labeling, second strand synthesis, reverse transcription and by chemical methods. When using radiolabeled probes, hybridization can be detected by techniques such as autoradiography, scintillation counting or gamma counting. The chosen detection method depends on the particular radioisotope used for labeling.

Non-isotopic materials can also be used for labeling and may be introduced internally between nucleotides or at an end of the oligonucleotide. Modified nucleotides may be incorporated enzymatically or chemically. Chemical modifications of the oligonucleotide may be performed during or after synthesis of the oligonucleotide using techniques known in the art. For example, through use of non-nucleotide linker groups disclosed by Arnold et al. in U.S. Pat. No. 6,031,091. Non-isotopic labels include fluorescent molecules, chemiluminescent molecules, fluorescent chemiluminescent molecules, phosphorescent molecules, electrochemiluminescent molecules, chromophores, enzymes, enzyme cofactors, enzyme substrates, dyes and haptens or other ligands. Another useful labeling technique is a base sequence that is unable to stably hybridize to the target nucleic acid under stringent conditions. Probes of the present invention are preferably labeled with an acridinium ester. (Acridinium ester labeling is disclosed by Arnold et al. in U.S. Pat. No. 5,185,439.)

The selected hybridization assay probe can then be brought into contact with a test sample suspected of containing *Cryptosporidium* or *Cryptosporidium parvum* organisms. Generally, the test sample is from a source which also contains unknown organisms. After bringing the probe into contact with the test sample, the test sample can be incubated under conditions permitting preferential hybridization of the probe to a target nucleic acid derived from *Cryptosporidium* or *Cryptosporidium parvum* organisms which may be present in the test sample in the presence of nucleic acid derived from other organisms in the test sample.

The probe may also be combined with one or more unlabeled helper probes to facilitate binding to target nucleic acid derived from *Cryptosporidium* or *Cryptosporidium parvum* organisms. After the probe has hybridized to target nucleic acid present in the test sample, the resulting hybrid may be separated and detected by various techniques well known in the art, such as hydroxyapatite adsorption and radioactive monitoring. Other techniques include those which involve selectively degrading label associated with unhybridized probe and then measuring the amount of remaining label associated with hybridized probe, as disclosed in U.S. Pat. No. 5,283,174. The inventors particularly prefer this latter technique.

E. Helper Probes Used in the Detection of *Cryptosporidium*

Another embodiment of this invention relates to novel helper probes. As mentioned above, helper probes can be used to facilitate hybridization of hybridization assay probes to their intended target nucleic acids, so that the hybridization assay probes more readily form probe:target nucleic acid duplexes than they would in the absence of helper probes. (Helper probes are disclosed by Hogan et al., "Means and Method for Enhancing Nucleic Acid Hybridization," U.S. Pat. No. 5,030,557.) Each helper probe contains an oligonucleotide that is sufficiently complementary to a target nucleic acid sequence to form a helper probe:target nucleic acid duplex under stringent hybridization assay conditions. The stringent hybridization assay conditions employed with a given helper probe are determined by the conditions used for preferentially hybridizing the associated hybridization assay probe to the target nucleic acid.

Regions of single stranded RNA and DNA can be involved in secondary and tertiary structures even under stringent hybridization assay conditions. Such structures can sterically inhibit or block hybridization of a hybridization assay probe to a target nucleic acid. Hybridization of the helper probe to the target nucleic acid alters the secondary and tertiary structure of the target nucleic acid, thereby rendering the target region more accessible by the hybridization assay probe. As a result helper probes enhance the kinetics and/or the melting temperature of the hybridization assay probe:target nucleic acid duplex. Helper probes are generally selected to hybridize to nucleic acid sequences located near the target region of the hybridization assay probe.

Helper probes which can be used with the *Cryptosporidium* hybridization assay probes of the present invention are targeted to nucleic acid sequences within *Cryptosporidium*-derived nucleic acid. Likewise, helper probes which can be used with the *Cryptosporidium parvum* hybridization assay probes of the present invention are targeted to nucleic acid sequences within *Cryptosporidium parvum*-derived nucleic acid. Each helper probe comprises an oligonucleotide which targets a base region present in a target nucleic acid. Preferably, the helper probe contains an at least 10 contiguous base region which his at least 80% complementary to an at least 10 contiguous base region present in a target nucleic acid sequence present in target nucleic acid derived from *Cryptosporidium* or *Cryptosporidium parvum* organisms, as appropriate. Helper probes and their associated hybridization assay probes have different target nucleic acid sequences contained within the same target nucleic acid. The helper probes of the present invention are preferably oligonucleotides up to 100 bases in length, more preferably from 12 to 50 bases in length, and even more preferably from 18 to 35 bases in length. Alternatively, the helper probes may be at least 90% complementary, or even perfectly complementary, to their target regions.

Examples of *Cryptosporidium* helper probes which may be useful in the present invention are those comprising an oligonucleotide having or substantially corresponding to the base sequence of SEQ ID NO:21, SEQ ID NO:22, SEQ ID NO:23, SEQ ID NO:24, SEQ ID NO:25, SEQ ID NO:26, SEQ ID NO:27 or SEQ ID NO:28.

Examples of *Cryptosporidium parvum* helper probes which may be useful in the present invention are those comprising an oligonucleotide having or substantially corresponding to the base sequence of SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43 or SEQ ID NO:44. While the inventors found that helper probes consisting of the nucleotide base sequences of SEQ ID NO:38 (20 pmol) and SEQ ID NO:39 (20 pmol), when provided to a 200 µl sample solution containing 100 pmol probe and target nucleic acid ranging in amounts from 0.1 fmol to 100 fmol, did not appear to facilitate hybridization of the probe to the target, it is still believed that optimization of the concentration of these helper probes may result in improved hybridization of a hybridization assay probe consisting of the nucleotide base sequence of SEQ ID NO:13 or SEQ ID NO:17 to a complementary sequence contained in a *Cryptosporidium parvum* 18S rRNA target nucleic acid.

When the helper probes are used in combination with *Cryptosporidium* hybridization assay probes, the preferred hybridization assay probe comprises an oligonucleotide having or substantially corresponding to the base sequence of SEQ ID NO:1, SEQ ID NO:2, SEQ ID NO:3 or SEQ ID NO:4, and the preferred helper probe comprises an oligonucleotide having or substantially corresponding to the base sequence of SEQ ID NO:21, SEQ ID NO:22, SEQ ID NO:23, SEQ ID NO:24, SEQ ID NO:25, SEQ ID NO:26, SEQ ID NO:27 or SEQ ID NO:28.

In one preferred embodiment of this combination, the *Cryptosporidium* hybridization assay probe comprises an oligonucleotide having or substantially corresponding to the base sequence of SEQ ID NO:1, SEQ ID NO:2, SEQ ID NO:3 or SEQ ID NO:4, and the helper probe comprises an oligonucleotide having or substantially corresponding to the base sequence of SEQ ID NO:21, SEQ ID NO:23, SEQ ID NO:25 or SEQ ID NO:27.

In a further preferred embodiment of this combination, the *Cryptosporidium* hybridization assay probe comprises an oligonucleotide having or substantially corresponding to the base sequence of SEQ ID NO:1, SEQ ID NO:2, SEQ ID NO:3 or SEQ ID NO:4, and the helper probe comprises an oligonucleotide having or substantially corresponding to the base sequence of SEQ ID NO:22, SEQ ID NO:24, SEQ ID NO:26 or SEQ ID NO:28.

Another preferred combination includes at least two helper probes when the *Cryptosporidium* hybridization assay probe comprises an oligonucleotide having or substantially corresponding to the base sequence of SEQ ID NO:1, SEQ ID NO:2, SEQ ID NO:3 or SEQ ID NO:4. In this combination, the first helper probe preferably comprises an oligonucleotide having or substantially corresponding to the base sequence of SEQ ID NO:21, SEQ ID NO:23, SEQ ID NO:25 or SEQ ID NO:27, and the second helper probe preferably comprises an oligonucleotide having or substantially corresponding to the base sequence of SEQ ID NO:22, SEQ ID NO:24, SEQ ID NO:26 or SEQ ID NO:28.

When helper probes are used in combination with *Cryptosporidium parvum* hybridization assay probes, the following combinations are preferred. When the hybridization assay probe comprises an oligonucleotide having or substantially corresponding to the base sequence of SEQ ID NO:5, SEQ ID NO:6, SEQ ID NO:9, SEQ ID NO:10, SEQ ID NO:13, SEQ ID NO:14, SEQ ID NO:17 or SEQ ID NO:18, the helper probe preferably comprises an oligonucleotide having or substantially corresponding to the base sequence of SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43 or SEQ ID NO:44.

In one embodiment of this combination, the *Cryptosporidium parvum* hybridization assay probe comprises an oligonucleotide having or substantially corresponding to the base sequence of SEQ ID NO:5, SEQ ID NO:6, SEQ ID NO:9, SEQ ID NO:10, SEQ ID NO:13, SEQ ID NO:14, SEQ ID NO:17 or SEQ ID NO:18, and the helper probe comprises an oligonucleotide having or substantially corresponding to the base sequence of SEQ ID NO:29, SEQ ID NO:33, SEQ ID NO:37 or SEQ ID NO:41.

In a further embodiment of this combination, the *Cryptosporidium parvum* hybridization assay probe comprises an oligonucleotide having or substantially corresponding to the base sequence of SEQ ID NO:5, SEQ ID NO:6, SEQ ID NO:9, SEQ ID NO:10, SEQ ID NO:13, SEQ ID NO:14, SEQ ID NO:17 or SEQ ID NO:18, and the helper probe comprises an oligonucleotide having or substantially corresponding to the base sequence of SEQ ID NO:30, SEQ ID NO:34, SEQ ID NO:38 or SEQ ID NO:42.

In another embodiment of this combination, the *Cryptosporidium parvum* hybridization assay probe comprises an oligonucleotide having or substantially corresponding to the base sequence of SEQ ID NO:5, SEQ ID NO:6, SEQ ID NO:9, SEQ ID NO:10, SEQ ID NO:13, SEQ ID NO:14, SEQ ID NO:17 or SEQ ID NO:18, and the helper probe comprises an oligonucleotide having or substantially corresponding to the base sequence of SEQ ID NO:31, SEQ ID NO:35, SEQ ID NO:39 or SEQ ID NO:43.

In yet a further embodiment of this combination, the *Cryptosporidium parvum* hybridization assay probe comprises an oligonucleotide having or substantially corresponding to the base sequence of SEQ ID NO:5, SEQ ID NO:6, SEQ ID NO:9, SEQ ID NO:10, SEQ ID NO:13, SEQ ID NO:14, SEQ ID NO:17 or SEQ ID NO:18, and the helper probe comprises an oligonucleotide having or substantially corresponding to the base sequence of SEQ ID NO:32, SEQ ID NO:36, SEQ ID NO:40 or SEQ ID NO:44.

Another preferred combination includes at least two helper probes when the *Cryptosporidium parvum* hybridization assay probe comprises an oligonucleotide having or substantially corresponding to the base sequence of SEQ ID NO:5, SEQ ID NO:6, SEQ ID NO:9, SEQ ID NO:10, SEQ ID NO:13, SEQ ID NO:14, SEQ ID NO:17 or SEQ ID NO:18. In this combination, the first helper probe preferably comprises an oligonucleotide having or substantially corresponding to the base sequence of SEQ ID NO:29, SEQ ID NO:30, SEQ ID NO:33, SEQ ID NO:34, SEQ ID NO:37, SEQ ID NO:38, SEQ ID NO:41 or SEQ ID NO:42, and the second helper probe preferably comprises an oligonucleotide having or substantially corresponding to the base sequence of SEQ ID NO:31, SEQ ID NO:32, SEQ ID NO:35, SEQ ID NO:36, SEQ ID NO:39, SEQ ID NO:40, SEQ ID NO:43 or SEQ ID NO:44.

In one embodiment of this combination, the *Cryptosporidium parvum* hybridization assay probe comprises an oligonucleotide having or substantially corresponding to the base sequence of SEQ ID NO:5, SEQ ID NO:6, SEQ ID NO:9, SEQ ID NO:10, SEQ ID NO:13, SEQ ID NO:14, SEQ ID NO:17 or SEQ ID NO:18. The first helper probe comprises an oligonucleotide having or substantially corresponding to the base sequence of SEQ ID NO:29, SEQ ID NO:33, SEQ ID NO:37 or SEQ ID NO:41, and the second helper probe comprises an oligonucleotide having or substantially corresponding to the base sequence of SEQ ID NO:31, SEQ ID NO:35, SEQ ID NO:39 or SEQ ID NO:43.

In a further embodiment of this combination, the *Cryptosporidium parvum* hybridization assay probe comprises an oligonucleotide having or substantially corresponding to the base sequence of SEQ ID NO:5, SEQ ID NO:6, SEQ ID NO:9, SEQ ID NO:10, SEQ ID NO:13, SEQ ID NO:14, SEQ ID NO:17 or SEQ ID NO:18. The first helper probe comprises an oligonucleotide having or substantially corresponding to the base sequence of SEQ ID NO:29, SEQ ID NO:33, SEQ ID NO:37 or SEQ ID NO:41, and the second helper probe comprises an oligonucleotide having or substantially corresponding to the base sequence of SEQ ID NO:32, SEQ ID NO:36, SEQ ID NO:40 or SEQ ID NO:44.

In another embodiment of this combination, the *Cryptosporidium parvum* hybridization assay probe comprises an oligonucleotide having or substantially corresponding to the base sequence of SEQ ID NO:5, SEQ ID NO:6, SEQ ID NO:9, SEQ ID NO:10, SEQ ID NO:13, SEQ ID NO:14, SEQ ID NO:17 or SEQ ID NO:18. The first helper probe comprises an oligonucleotide having or substantially corresponding to the base sequence of SEQ ID NO:30, SEQ ID NO:34, SEQ ID NO:38 or SEQ ID NO:42, and the second helper probe comprises an oligonucleotide having or substantially corresponding to the base sequence of SEQ ID NO:31, SEQ ID NO:35, SEQ ID NO:39 or SEQ ID NO:43.

In yet a further embodiment of this combination, the *Cryptosporidium parvum* hybridization assay probe comprises an oligonucleotide having or substantially corresponding to the base sequence of SEQ ID NO:5, SEQ ID NO:6, SEQ ID NO:9, SEQ ID NO:10, SEQ ID NO:13, SEQ ID NO:14, SEQ ID NO:17 or SEQ ID NO:18. The first helper probe comprises an oligonucleotide having or substantially corresponding to the base sequence of SEQ ID NO:30, SEQ ID NO:34, SEQ ID NO:38 or SEQ ID NO:42, and the second helper probe comprises an oligonucleotide having or substantially corresponding to the base sequence of SEQ ID NO:32, SEQ ID NO:36, SEQ ID NO:40 or SEQ ID NO:44.

In yet another preferred combination, the *Cryptosporidium parvum* hybridization assay probe comprises an oligonucleotide having or substantially corresponding to the base sequence of SEQ ID NO:7, SEQ ID NO:11, SEQ ID NO:15 or SEQ ID NO:19, and the helper probe comprises an oligonucleotide having or substantially corresponding to the base sequence of SEQ ID NO:29, SEQ ID NO:30, SEQ ID NO:33, SEQ ID NO:34, SEQ ID NO:37, SEQ ID NO:38, SEQ ID NO:41 or SEQ ID NO:42.

In one embodiment of this combination, the *Cryptosporidium parvum* hybridization assay probe comprises an oligonucleotide having or substantially corresponding to the base sequence of SEQ ID NO:7, SEQ ID NO:11, SEQ ID NO:15 or SEQ ID NO:19, and the helper probe comprises an oligonucleotide having or substantially corresponding to the base sequence of SEQ ID NO:29, SEQ ID NO:33, SEQ ID NO:37 or SEQ ID NO:41.

In further embodiment of this combination, the *Cryptosporidium parvum* hybridization assay probe comprises an oligonucleotide having or substantially corresponding to the base sequence of SEQ ID NO:7, SEQ ID NO:11, SEQ ID NO:15 or SEQ ID NO:19, and the helper probe comprises an oligonucleotide having or substantially corresponding to the base sequence of SEQ ID NO:30, SEQ ID NO:34, SEQ ID NO:38 or SEQ ID NO:42.

F. Nucleic Acid Compositions

In another related aspect, the present invention features compositions comprising a nucleic acid hybrid formed between a hybridization assay probe and a target nucleic acid ("probe:target") under stringent hybridization assay conditions. One use of the hybrid formed between a probe and a target nucleic acid is to provide an indication of the presence or amount of a target organism or group of organisms in a test sample. For example, acridinium ester (AE) present in nucleic acid hybrids is resistant to hydrolysis in an alkali solution, whereas AE present in single-stranded nucleic acid is susceptible to hydrolysis in an alkali solution (see U.S. Pat. No. 5,238,174). Thus, the presence of target nucleic acids can be detected, after the hydrolysis of the unbound AE-labeled probe, by measuring chemiluminescence of acridinium ester remaining associated with the nucleic acid hybrid.

The present invention also contemplates compositions comprising nucleic acid hybrids formed between a helper probe and a target nucleic acid ("helper probe:target") under stringent hybridization assay conditions. One use of the hybrid formed between a helper probe and a target nucleic acid is to make available a particular nucleic acid sequence for hybridization. For example, a hybrid formed between a helper probe and a target nucleic acid may render a nucleic acid sequence available for hybridization with a hybridization assay probe. A full description of the use of helper probes is provided by Hogan et al. in U.S. Pat. No. 5,030,557.

The present invention also features compositions comprising a nucleic acid formed between an amplification primer and a target nucleic acid ("primer:target") under amplification conditions. One use of the hybrid formed between a primer and a target nucleic acid is to provide an initiation site for a nucleic acid polymerase at the 3' end of the amplification primer. For example, a hybrid may form an initiation site for reverse transcriptase, DNA polymerases such as Taq polymerase or T4 DNA polymerase, and RNA polymerases such as T7 polymerase, SP6 polymerase, T3 polymerase and the like.

Compositions of the present invention include compositions for determining the presence or amount of *Cryptosporidium* or *Cryptosporidium parvum* organisms in a test sample comprising a nucleic acid hybrid formed between a target nucleic acid derived from a *Cryptosporidium* organism and an oligonucleotide having or substantially corresponding to the base sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67 or SEQ ID NO:68.

The present invention also contemplates compositions for determining the presence or amount of *Cryptosporidium* organisms in a test sample comprising a nucleic acid hybrid formed between a target nucleic acid derived from a *Cryptosporidium* organism and a hybridization assay probe comprising an oligonucleotide having or substantially corresponding to the base sequence of SEQ ID NO:1, SEQ ID NO:2, SEQ ID NO:3 or SEQ ID NO:4. In another embodiment, these probe:target compositions may further comprise a helper probe hybridized to the *Cryptosporidium*-derived target nucleic acid, where the helper probe comprises an oligonucleotide having or substantially corresponding to the base sequence of SEQ ID NO:21, SEQ ID NO:22, SEQ ID NO:23, SEQ ID NO:24, SEQ ID NO:25, SEQ ID NO:26, SEQ ID NO:27 or SEQ ID NO:28. Preferred hybridization assay probe and helper probe combinations for forming this latter group of nucleic acid hybrid compositions are those of the probe mix combinations described above under the heading "Helper Probes Used in the Detection of *Cryptosporidium*."

The present invention further contemplates compositions for determining the presence or amount of *Cryptosporidium parvum* organisms in a test sample comprising a nucleic acid hybrid formed between a target nucleic acid derived from a *Cryptosporidium parvum* organism and a hybridization assay probe comprising an oligonucleotide having or substantially corresponding to the base sequence of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 or SEQ ID NO:20. In another embodiment, these probe:target compositions may further comprise a helper probe hybridized to the *Cryptosporidium parvum*-derived target nucleic acid, where the helper probe comprises an oligonucleotide having or substantially corresponding to the base sequence of SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43 or SEQ ID NO:44. Preferred hybridization assay probe and helper probe combinations for forming this latter group of nucleic acid hybrid compositions are those of the probe mix combinations described above under the heading "Helper Probes Used in the Detection of *Cryptosporidium*."

The present invention also contemplates compositions for amplifying a target sequence present in a target nucleic acid derived from a *Cryptosporidium* organism, where the compositions comprise a nucleic acid hybrid formed between the target nucleic acid and an amplification primer comprising an oligonucleotide having or substantially corresponding to the base sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67 or SEQ ID NO:68. Preferred amplification primer combinations for forming these nucleic acid hybrid compositions are those described above under the heading "Amplification of *Cryptosporidium* Ribosomal Nucleic Acid."

G. Assay Methods

The present invention contemplates various methods for assaying for the presence or amount of nucleic acid derived from *Cryptosporidium* or *Cryptosporidium parvum* organisms in a test sample. One skilled in the art will understand that the exact assay conditions, probes and/or primers used will vary depending on the particular assay format used and the source of the sample.

One aspect of the present invention relates to a method for determining the presence or amount of *Cryptosporidium* organisms in a test sample by contacting the test sample under stringent hybridization assay conditions with a hybridization assay probe capable of preferentially hybridizing under stringent hybridization assay conditions to a *Cryptosporidium*-derived target nucleic acid over nucleic acids from non-Cryptosporidium organisms present in the test sample. In this method, the target nucleic acid contains a base sequence having or substantially corresponding to the base sequence of SEQ ID NO:1, SEQ ID NO:2, SEQ ID NO:3 or SEQ ID NO:4. (Depending on the source, the test sample may contain unknown organisms that the probes of this method can distinguish over.) Preferred to probes for use in this method comprise an oligonucleotide having or substantially corresponding to the base sequence of SEQ ID NO:1, SEQ ID NO:2, SEQ ID NO:3 or SEQ ID NO:4.

In a preferred embodiment, the method for determining the presence or amount of *Cryptosporidium* organisms in a test sample may also include the step of contacting the test sample with one or more helper probes for facilitating hybridization of the probe to the target nucleic acid. While the helper probes may be added to the sample before or after the addition of the hybridization assay probe, the helper probes and hybridization assay probe are preferably provided to the test sample at the same time. Preferred helper probes for use in this method comprise an oligonucleotide having or substantially corresponding to the base sequence SEQ ID NO:21, SEQ ID NO:22, SEQ ID NO:23, SEQ ID NO:24, SEQ ID NO:25, SEQ ID NO:26, SEQ ID NO:27 or SEQ ID NO:28. Particular combinations of hybridization assay probes and helper probes which can be used in this method are set forth above under the heading "Helper Probes Used in the Detection of *Cryptosporidium*."

Another aspect of the present invention relates to a method for determining the presence or amount of *Cryptosporidium parvum* organisms in a test sample by contacting the test sample under stringent hybridization assay conditions with a hybridization assay probe capable of preferentially hybridizing under stringent hybridization assay conditions to a *Cryptosporidium parvum*-derived target nucleic acid over nucleic acids from non-*Cryptosporidium parvum* organisms present in the test sample. In this method, the target nucleic acid contains a base sequence having or substantially corresponding to the base sequence of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 or SEQ ID NO:20. (Depending on the source, the test sample may contain unknown organisms that the probes of this method can distinguish over.) Preferred probes for use in this method comprise an oligonucleotide having or substantially corresponding to the base sequence of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 or SEQ ID NO:20.

In a preferred embodiment, the method for determining the presence or amount of *Cryptosporidium parvum* organisms in a test sample may also include the step of contacting the test sample with one or more helper probes for facilitating hybridization of the probe to the target nucleic acid. While the helper probes may be added to the sample before or after the addition of the hybridization assay probe, the helper probes and hybridization assay probe are preferably provided to the test sample at the same time. Preferred helper probes for use in this method comprise an oligonucleotide having or substantially corresponding to the base sequence SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43 or SEQ ID NO:44. Particular combinations of hybridization assay probes and helper probes which can be used in this method are set forth above under the heading "Helper Probes Used in the Detection of *Cryptosporidium*."

Yet another aspect of the present invention relates to a method for amplifying *Cryptosporidium*-derived nucleic acid in a test sample by contacting the test sample under amplification conditions with one or more amplification primers which, when contacted with a nucleic acid polymerase, will bind to or cause elongation through a nucleic acid region having the base sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67 or SEQ ID NO:68. Preferred amplification primers for use in this method comprise an oligonucleotide having or substantially corresponding to the base sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67 or SEQ ID NO:68, where the amplification primer optionally includes a nucleic acid sequence recognized by an RNA polymerase or which enhances initiation or elongation by an RNA polymerase. Particular combinations of amplification primers which can be used in this method are set forth above under the heading "Amplification of *Cryptosporidium* Ribosomal Nucleic Acid."

In a preferred embodiment, the method for amplifying *Cryptosporidium*-derived nucleic acid in a test sample further includes the step of contacting the test sample under stringent hybridization assay conditions with a hybridization assay probe capable of preferentially hybridizing under stringent hybridization assay conditions to an amplified *Cryptosporidium* target nucleic acid over nucleic acids from non-*Cryptosporidium* organisms present in the test sample. While the test sample is generally contacted with the hybridization assay probe after a sufficient period for amplification has passed, the amplification primers and hybridization assay probe may be added to the sample in any order, especially where the hybridization assay probe is a self-hybridizing probe, such as a Molecular Torch or a Molecular Beacon discussed supra. This step of contacting the test sample with a hybridization assay probe is performed so that the presence or amount of *Cryptosporidium* organisms in the test sample can be determined. Preferred probes for use in this method comprise an oligonucleotide having or substantially corresponding to the base sequence of SEQ ID NO:1, SEQ ID NO:2, SEQ ID NO:3 or SEQ ID NO:4. The probes may further include a label to facilitate detection in the test sample.

In one preferred embodiment, this method is carried out with a set of at least two amplification primers for amplifying *Cryptosporidium*-derived nucleic acid which includes a first amplification primer comprising an oligonucleotide having or substantially corresponding to the base sequence of SEQ ID NO:45, SEQ ID NO:51, SEQ ID NO:57 or SEQ ID NO:63, and a second amplification primer comprising an oligonucleotide having or substantially corresponding to the base sequence of SEQ ID NO:48, SEQ ID NO:54, SEQ ID NO:60 or SEQ ID NO:66. The hybridization assay probe used to specifically detect amplified *Cryptosporidium* nucleic acid in the test sample comprises an oligonucleotide having or substantially corresponding to the base sequence of SEQ ID NO:1, SEQ ID NO:2, SEQ ID NO:3 or SEQ ID NO:4.

In another preferred embodiment, this method is carried out with a set of at least two amplification primers for amplifying *Cryptosporidium*-derived nucleic acid which includes a first amplification primer comprising an oligonucleotide having or substantially corresponding to the base sequence of SEQ ID NO:46, SEQ ID NO:52, SEQ ID NO:58 or SEQ ID NO:64, and a second amplification primer comprising an oligonucleotide having or substantially corresponding to the base sequence of SEQ ID NO:48, SEQ ID NO:54, SEQ ID NO:60 or SEQ ID NO:66. The hybridization assay probe used to specifically detect amplified *Cryptosporidium* nucleic acid in the test sample comprises an oligonucleotide having or substantially corresponding to the base sequence of SEQ ID NO:1, SEQ ID NO:2, SEQ ID NO:3 or SEQ ID NO:4.

In a preferred embodiment, the method for amplifying *Cryptosporidium*-derived nucleic acid in a test sample further includes the step of contacting the test sample under stringent hybridization assay conditions with a hybridization assay probe capable of preferentially hybridizing under stringent hybridization assay conditions to an amplified *Cryptosporidium parvum* target nucleic acid over nucleic acids from non-*Cryptosporidium parvum* organisms present in the test sample. While the test sample is generally contacted with the hybridization assay probe after a sufficient period for amplification has passed, the amplification primers and hybridization assay probe may be added to the sample in any order, especially where the hybridization assay probe is a self-hybridizing probe, such as a Molecular Torch or a Molecular Beacon discussed supra. This step of contacting the test sample with a hybridization assay probe is performed so that the presence or amount of *Cryptosporidium parvum* organisms in the test sample can be determined Preferred probes for use in this method comprise an oligonucleotide having or substantially corresponding to the base sequence of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 or SEQ ID NO:20. The probes may further include a label to facilitate detection in the test sample.

In one preferred embodiment, this method is carried out with a set of at least two amplification primers for amplifying *Cryptosporidium*-derived nucleic acid which includes a first amplification primer comprising an oligonucleotide having or substantially corresponding to the base sequence of SEQ ID NO:45, SEQ ID NO:51, SEQ ID NO:57 or SEQ ID NO:63, and a second amplification primer comprising an oligonucleotide having or substantially corresponding to the base sequence of SEQ ID NO:47, SEQ ID NO:53, SEQ ID NO:59 or SEQ ID NO:65. The hybridization assay probe used to specifically detect amplified *Cryptosporidium parvum* nucleic acid in the test sample comprises an oligonucleotide having or substantially corresponding to the base sequence of SEQ ID NO:5, SEQ ID NO:6, SEQ ID NO:7, SEQ ID NO:9, SEQ ID NO:10, SEQ ID NO:11, SEQ ID NO:13, SEQ ID NO:14, SEQ ID NO:15, SEQ ID NO:17, SEQ ID NO:18 or SEQ ID NO:19.

In another preferred embodiment, this method is carried out with a set of at least two amplification primers for amplifying *Cryptosporidium*-derived nucleic acid which includes a first amplification primer comprising an oligonucleotide having or substantially corresponding to the base sequence of SEQ ID NO:45, SEQ ID NO:51, SEQ ID NO:57 or SEQ ID NO:63, and a second amplification primer comprising an oligonucleotide having or substantially corresponding to the base sequence of SEQ ID NO:48, SEQ ID NO:54, SEQ ID NO:60 or SEQ ID NO:66. The hybridization assay probe used to specifically detect amplified *Cryptosporidium parvum* nucleic acid in the test sample comprises an oligonucleotide having or substantially corresponding to the base sequence of SEQ ID NO:5, SEQ ID NO:6, SEQ ID NO:7, SEQ ID NO:9, SEQ ID NO:10, SEQ ID NO:11, SEQ ID NO:13, SEQ ID NO:14, SEQ ID NO:15, SEQ ID NO:17, SEQ ID NO:18 or SEQ ID NO:19.

In yet another preferred embodiment, this method is carried out with a set of at least two amplification primers for amplifying *Cryptosporidium*-derived nucleic acid which includes a first amplification primer comprising an oligonucleotide having or substantially corresponding to the base sequence of SEQ ID NO:46, SEQ ID NO:52, SEQ ID NO:58 or SEQ ID NO:64, and a second amplification primer comprising an oligonucleotide having or substantially corresponding to the base sequence of SEQ ID NO:47, SEQ ID NO:53, SEQ ID NO:59 or SEQ ID NO:65. The hybridization assay probe used to specifically detect amplified *Cryptosporidium parvum* nucleic acid in the test sample comprises an oligonucleotide having or substantially corresponding to the base sequence of SEQ ID NO:5, SEQ ID NO:6, SEQ ID NO:7, SEQ ID NO:9, SEQ ID NO:10, SEQ ID NO:11, SEQ ID NO:13, SEQ ID NO:14, SEQ ID NO:15, SEQ ID NO:17, SEQ ID NO:18 or SEQ ID NO:19.

In still another preferred embodiment, this method is carried out with a set of at least two amplification primers for amplifying *Cryptosporidium*-derived nucleic acid which includes a first amplification primer comprising an oligonucleotide having or substantially corresponding to the base sequence of SEQ ID NO:46, SEQ ID NO:52, SEQ ID NO:58 or SEQ ID NO:64, and a second amplification primer comprising an oligonucleotide having or substantially corresponding to the base sequence of SEQ ID NO:48, SEQ ID NO:54, SEQ ID NO:60 or SEQ ID NO:66. The hybridization assay probe used to specifically detect amplified *Cryptosporidium parvum* nucleic acid in the test sample comprises an oligonucleotide having or substantially corresponding to the base sequence of SEQ ID NO:5, SEQ ID NO:6, SEQ ID NO:7, SEQ ID NO:9, SEQ ID NO:10, SEQ ID NO:11, SEQ ID NO:13, SEQ ID NO:14, SEQ ID NO:15, SEQ ID NO:17, SEQ ID NO:18 or SEQ ID NO:19.

In a further preferred embodiment, this method is carried out with a set of at least two amplification primers for amplifying *Cryptosporidium*-derived nucleic acid which includes a first amplification primer comprising an oligonucleotide having or substantially corresponding to the base sequence of SEQ ID NO:49, SEQ ID NO:55, SEQ ID NO:61 or SEQ ID NO:67, and a second amplification primer comprising an oligonucleotide having or substantially corresponding to the base sequence of SEQ ID NO:50, SEQ ID NO:56, SEQ ID NO:62 or SEQ ID NO:68. The hybridization assay probe used to specifically detect amplified *Cryptosporidium parvum* nucleic acid in the test sample comprises an oligonucleotide having or substantially corresponding to the base sequence of SEQ ID NO:8, SEQ ID NO:12, SEQ ID NO:16 or SEQ ID NO:20.

H. Diagnostic Systems

The present invention also contemplates diagnostic systems in kit form. A diagnostic system of the present invention may include a kit which contains, in an amount sufficient for at least one assay, any of the hybridization assay probes, helper probes and/or amplification primers of the present invention in a packaging material. Typically, the kits will also include instructions recorded in a tangible form (e.g., contained on paper or an electronic medium) for using the packaged probes and/or primers in an amplification and/or detection assay for determining the presence or amount of *Cryptosporidium* or *Cryptosporidium parvum* organisms in a test sample.

The various components of the diagnostic systems may be provided in a variety of forms. For example, the required enzymes, the nucleotide triphosphates, the probes and/or primers may be provided as a lyophilized reagent. These lyophilized reagents may be pre-mixed before lyophilization so that when reconstituted they form a complete mixture with the proper ratio of each of the components ready for use in the assay. In addition, the diagnostic systems of the present invention may contain a reconstitution reagent for reconstituting the lyophilized reagents of the kit. In preferred kits for amplifying target nucleic acid derived from *Cryptosporidium* organisms, the enzymes, nucleotide triphosphates and required cofactors for the enzymes are provided as a single lyophilized reagent that, when reconstituted, forms a proper reagent for use in the present amplification methods. In these kits, a lyophilized primer reagent may also be provided. In other preferred kits, lyophilized probe reagents are provided.

Typical packaging materials would include solid matrices such as glass, plastic, paper, foil, micro-particles and the like, capable of holding within fixed limits hybridization assay probes, helper probes and/or amplification primers of the present invention. Thus, for example, the packaging materials can include glass vials used to contain sub-milligram (e.g., picogram or nanogram) quantities of a contemplated probe or primer, or they can be microtiter plate wells to which probes or primers of the present invention have been operatively affixed, i.e., linked so as to be capable of participating in an amplification and/or detection method of the present invention.

The instructions will typically indicate the reagents and/or concentrations of reagents and at least one assay method parameter which might be, for example, the relative amounts of reagents to use per amount of sample. In addition, such specifics as maintenance, time periods, temperature and buffer conditions may also be included.

The diagnostic systems of the present invention contemplate kits having any of the hybridization assay probes, helper probes and/or amplification primers described herein, whether provided individually or in one of the preferred combinations described above, for use in amplifying and/or determining the presence or amount of *Cryptosporidium* or *Cryptosporidium parvum* organisms in a test sample.

I. EXAMPLES

Examples are provided below illustrating different aspects and embodiments of the invention. Skilled artisans will appreciate that these examples are not intended to limit the invention to the specific embodiments described therein.

A. Isolation and Purification of *Cryptosporidium* Nucleic Acid

To obtain *Cryptosporidium* ribosomal RNA, *Cryptosporidium* oocysts are first isolated from a sample by centrifuging the sample in an Eppendorf 1.5 ml micro test tube (Brinkmann Instruments, Inc., Westbury, N.Y.; Cat. No. 22 60 002 8) at 7,000 rpm for 5 minutes using an Eppendorf microcentrifuge (Brinkmann Instruments, Inc.; Cat. No. 22 62 120-3). The supernatant is then aspirated off and the remaining pellet is resuspended in 200 µl lysis/binding buffer provided with Ambion's RNAaqueous™ kit (Ambion, Inc, Austin, Tex.; Cat. No. AM-1912).

Approximately 1.0 mm zirconia/silica beads (BioSpec Products, Inc., Bartlesville, Okla.; Cat. No. 11079110Z) are added to a 2.0 ml microcentrifuge vial (BioSpec Products, Inc.; Cat. No. 10832), filling the vial about three quarters full (1.5 ml). Then, 500 µl of dimethylpyrocarbonate (DEPC)-treated water (Ambion, Inc.; Cat. No. 9922) is added to the vial and the vial is sealed and inverted by hand several times prior to aspirating the DEPC-treated water from the vial.

The resuspended pellet is removed from the micro test tube and added to the bead-containing vial. Additional lysis/binding buffer is added to completely fill the vial before the vial is again sealed and positioned in a BeadBeater™ (BioSpec Products, Inc.; Cat. No. 3110BX), which is run for 2 minutes at 5,000 rpm. The vial is removed from the BeadBeater™ and placed on ice for 4 minutes before being subjected to a second run in the BeadBeater™ for 2 minutes at 5,000 rpm. The vial is again placed on ice for 4 minutes.

The supernatant is pipetted from the vial, thereby separating it from the beads, and added to a new 2 ml microcentrifuge vial (BioSpec Products, Inc.; Cat. No. 10832). Also added to this vial is ethanol (64%) provided with the RNAqueous™ kit in equal volume with the supernatant before the vial is sealed and inverted by hand several times to ensure thorough mixing of the supernatant and ethanol. This mixture is then added in 600 µl aliquots to the filter cartridges of collection tubes provided with the RNAqueous™ kit. The collection tubes are then centrifuged for 30 seconds at 13,000 rpm in the Eppendorf microcentrifuge, the eluent is aspirated off, and 700 µl of Wash Solution I from the RNAqueous™ kit is added to each filter cartridge. The collection tubes are once more centrifuged at 13,000 rpm for 30 seconds, the eluent is removed, and 500 µl of Wash Solution ⅔ from the RNAqueous™ kit is added to the filter cartridges. This last centrifugation and treatment with Wash Solution ⅔ is repeated to ensure removal of the ethanol. The collection tubes are then centrifuged at 13,000 rpm for 30 seconds, and the eluent is removed prior to centrifuging the collection tubes at 13,000 rpm for 2 minutes.

The filter cartridges are then placed in another set of collection tubes provided with the RNAqueous™ kit, to which 50 µl of an elution solution provided with the RNAqueous™ kit (pre-heated to 95° C.) is added to these new collection tubes. The collection tubes are centrifuged for 1 minute at 13,000 rpm in the microcentrifuge before another 50 µl of the pre-heated elution solution is added to the collection tubes. A final 1 minute centrifugation at 13,000 rpm is performed, and the eluent from these last two centrifugations contains the purified RNA.

B. Hybridization Assay Probes

Hybridization assay probes specific for nucleic acid from *Cryptosporidium* or *Cryptosporidium parvum* were identified from the published sequences indicated supra and a determined 18S rRNA sequence for *Cryptosporidium parvum*. Probes specific for *Cryptosporidium* were identified by comparing 18S rRNA sequences of *Cryptosporidium parvum*, *Cryptosporidium muris*, *Cryptosporidium baileyi* and *Cryptosporidium wrairi* with 18S rRNA sequences of *Escherichia coli*, *Cyclospora cayetanensis*, *Sarcocystis hominis*, *Entamoeba histolytica* and *Eimeria praecox*. And to identify probes specific for *Cryptosporidium parvum*, an 18S rRNA sequence of *Cryptosporidium parvum* was compared with 18S rRNA sequences of *Cryptosporidium muris*, *Cryptosporidium baileyi* and *Cryptosporidium wrairi*. Regions of variability were identified which could be tested to verify specificity.

Hybridization assay probes having the base sequences of SEQ ID NO. 1, SEQ ID NO:3, SEQ ID NO:5, SEQ ID NO:7, SEQ ID NO:8, SEQ ID NO:10, SEQ ID NO:13, SEQ ID NO:15, SEQ ID NO:16 and SEQ ID NO:18 are featured in the examples described below. The probes were synthesized with a non-nucleotide linker, as disclosed by Arnold et al. in U.S. Pat. No. 6,031,091, and labeled with a chemiluminescent acridinium ester (AE), as disclosed by Arnold et al. in U.S. Pat. No. 5,185,439. The reactivity and specificity of the probes for *Cryptosporidium* and *Cryptosporidium parvum* nucleic acid are demonstrated using the Homogenous Protection Assay (HPA) disclosed by Arnold et al. in U.S. Pat. No. 5,283,174. Results are given in relative light units (RLU), which is a measure of the photons detected by a luminometer.

C. Reagents

Various reagents are identified in the examples below, which include a hybridization reagent, a selection reagent, an amplification reagent, a reconstitution buffer, an enzyme reagent, an enzyme dilution buffer and an oil reagent. The formulations and pH values (where relevant) of these reagents are as follows.

The "Hybridization Reagent" of the following examples is made up of 50 mM succinic acid, 1% (w/v) lithium lauryl sulfate (LLS), 7.5 mM aldrithiol-2, 0.6 M LiCl, 115 mM LiOH, 10 mM ethylenediaminetetraacetic acid (EDTA), 10 mM ethylene glycol N,N,N',N'-tetraacetic acid (EGTA) and 1.5% (v/v) ethyl alcohol (absolute), pH to 4.7.

The "Selection Reagent" of the following examples is made up of 600 mM boric acid, 240 mM NaOH and 1% (v/v) TRITON® X-100, pH to 8.5.

The "Amplification Reagent" of the following examples is made up of 4 mM each of ATP, GTP, UTP and CTP, 1 mM each of dATP, dGTP, dTTP and dCTP, 40 mM trizma base, pH 7.5, 25 mM $MgCl_2$, 17.5 mM KCl and 5% (w/v) polyvinylpyrrolidone. The Amplification Reagent is reconstituted with 1.5 ml distilled, deionized water.

The "Enzyme Reagent" of the following examples is made up of 125 mM N-acetyl-L-cysteine (NALC), 0.2% (v/v) TRITON® X-102, 20 mM N-2-hydroxyethylpiperazine-N'-2-ethanesulfonic acid (HEPES), pH 7.5, 0.1 mM EDTA, 0.1 mM zinc acetate, 0.2 M trehalose, 2000 units Moloney Murine Leukemia Virus ("MMLV") reverse transcriptase and 2000 units T7 RNA polymerase. (One "unit" of activity is defined as the synthesis and release of 5.75 fmol cDNA in 15 minutes at 37° C. for MMLV reverse transcriptase, and for T7 RNA polymerase, one "unit" of activity is defined as the production of 5.0 fmol RNA transcript in 20 minutes at 37° C.) The Enzyme Reagent is reconstituted with 1.5 mL Enzyme Diluent Buffer.

The "Enzyme Dilution Buffer" of the following examples is made up of 140 mM trizma base, pH 8.0, 1 mM EDTA, 10% (v/v) TRITON® X-102, 70 mM KCl and 20% (v/v) glycerol.

The "Detection Reagents" of the following examples comprise Detect Reagent I, which contains 0.1% (v/v) hydrogen peroxide and 1 mM nitric acid, and Detect Reagent II, which contains 1N sodium hydroxide and a surfactant component.

The "Oil Reagent" of the following examples is a mineral oil.

Example 1

Specific Detection of *Cryptosporidium* Nucleic Acid

This example illustrates the ability of a probe mixture containing an acridinium ester-labeled hybridization assay probe targeted to *Cryptosporidium* rRNA to selectively detect *Cryptosporidium* species in the presence of non-*Cryptosporidium* organisms. A hybridization assay probe having the base sequence of SEQ ID NO:3 is synthesized, as described above, to include a non-nucleotide linker positioned between nucleotides 11 and 12 (reading 5' to 3'). Additionally, unlabeled helper probes having the base sequences of SEQ ID NO:27 and SEQ ID NO:28 are included in the probe mixture to facilitate hybridization of the hybridization assay probe to *Cryptosporidium* nucleic acid. Except for the first nucleotide (reading 5' to 3'), which is substituted with the corresponding deoxynucleotide, each nucleotide of the helper probes is a ribonucleotide modified to include a 2'-O-methyl substitution to the ribofuranosyl moiety.

The specificity of the hybridization assay probe for *Cryptosporidium* nucleic acid is determined using a panel of duplicate sample sets, each set containing 100 ng of purified rRNA (50 ng per sample) from an isolate chosen from the group consisting of *Escherichia coli, Cyclospora cayetanensis, Sarcocystis hominis, Entamoeba histolytica, Eimeria praecox, Cryptosporidium parvum* and at least one of *Cryptosporidium muris, Cryptosporidium baileyi* and *Cryptosporidium wrairi. Cryptosporidium parvum* and *Cryptosporidium muris* isolates can be obtained from Waterborne Incorporated of New Orleans, La. (Part No. P102 for *Cryptosporidium parvum* and Part No. P104 for *Cryptosporidium muris*). A set of negative control samples is included to determine background levels.

Each sample is provided to a 12×75 mm polypropylene tube (Gen-Probe Incorporated; Cat. No. 2440). Additionally, each tube is provided with 0.1 pmol of the hybridization assay probe, 5.0 pmol of each helper probe, and 100 µl 1× Hybridization Reagent. To permit hybridization, the tubes are incubated at 60° C. in a circulating water bath (Precision Scientific, Winchester, Va.; Model 260; Cat. No. 51221035) for 30 minutes. Following hybridization, 300 µl Selection Reagent is added to each tube and the tubes are incubated at 60° C. in the circulating water bath for 10 minutes to hydrolyze acridinium ester labels associated with unhybridized probe. Samples are cooled on ice for 1 minute prior to being analyzed in a LEADER® 450i luminometer equipped with automatic injection of the Detection Regents. A net RLU value greater than 10,000 RLU is considered to be a positive result, and a net RLU value less than 10,000 RLU is considered to be a negative result. Net RLU values are based on the average RLU value of each sample set minus the average RLU value for the negative control set (i.e., background signal).

Example 2

Amplification and Detection of *Cryptosporidium* Nucleic Acid

This example illustrates the amplification of a target sequence of *Cryptosporidium* rRNA and detection of the amplified rRNA using a hybridization assay probe specific for *Cryptosporidium*-derived nucleic acid. In particular, a *Cryptosporidium* hybridization assay probe having the base sequence of SEQ ID NO:1 is synthesized, as described above, to include a non-nucleotide linker positioned between nucleotides 11 and 12 (reading 5' to 3'). This hybridization assay probe is of the same sense as the *Cryptosporidium* target rRNA and is used to detect product of a transcription-mediated amplification. Procedures for performing a transcription-mediated amplification are described supra and by Kacian et al. in U.S. Pat. Nos. 5,399,491 and 5,480,784. In addition, this hybridization assay probe is the opposite sense of the hybridization assay probe of Example 1, which is believed to be specific for nucleic acid from *Cryptosporidium* organisms. Accordingly, the hybridization assay probe of this example is expected to be specific for nucleic acid derived from *Cryptosporidium* organisms.

Ribosomal RNA from *Cryptosporidium parvum* and *Cryptosporidium muris* is separately amplified using one of the following promoter-primer/primer combinations: (i) a promoter-primer having a 5' end promoter base sequence of SEQ ID NO:69 and a 3' end sense template-specific base sequence of SEQ ID NO:60, and a primer having an antisense template-specific base sequence of SEQ ID NO:45; and (ii) a promoter-primer having a 5' end promoter base sequence of SEQ ID NO:69 and a 3' end sense template-specific base sequence of SEQ ID NO:60, and a primer having an antisense template-specific base sequence of SEQ ID NO:46. *Cryptosporidium parvum* and *Cryptosporidium muris* isolates can be obtained from Waterborne Incorporated of New Orleans, La. (Part No. P102 for *Cryptosporidium parvum* and Part No. P104 for *Cryptosporidium muris*).

Amplification is carried out in 12×75 mm polypropylene tubes (Gen-Probe Incorporated; Cat. No. 2440), each containing 0 amol, 0.2 amol or 2.0 amol of *Cryptosporidium parvum* or *Cryptosporidium muris* rRNA in duplicate sets, 15 pmol promoter-primer, 15 pmol primer, 25 μl Amplification Reagent, and distilled, deionized water to bring the total volume in each tube to 75 μl. Each sample receives 200 μl Oil Reagent and is incubated at 95° C. in a dry heat bath (Gen-Probe Incorporated; Cat. No. 4006) for 10 minutes. The samples are then transferred to a circulating water bath (Lauda Dr. R. Wobser GmbH & Co. KG, Lauda-Koenigshofen, Germany; Model No. M20-S) and incubated for 5 minutes at 42° C. before adding 25 μl of reconstituted Enzyme Reagent to each tube. Following a 60 minute incubation at 42° C. in the circulating water bath, 100 μl 1× Hybridization Reagent containing 100 fmol of the hybridization assay probe is added to each tube, the samples are incubated for 30 minutes at 60° C. in the circulating water bath, and signal from annealed hybridization assay probe is detected in the manner described in Example 1. Sample sets with an average RLU value greater than 10-fold the average RLU value for the negative control (0 amol target rRNA) indicate amplification of the target rRNA, and sample sets with an average RLU value less than 10-fold the average RLU for the negative control indicate no amplification of the target rRNA.

Example 3

Specific Detection of *Cryptosporidium parvum* Nucleic Acid

This example illustrates the ability of a probe mixture containing an acridinium ester-labeled hybridization assay probe targeted to *Cryptosporidium parvum* rRNA to selectively detect *Cryptosporidium parvum* organisms in the presence of non-*Cryptosporidium parvum* organisms. A hybridization assay probe having one of the following base sequences is synthesized, as described above: (i) SEQ ID NO:13 (non-nucleotide linker positioned between nucleotides 9 and 10, reading 5' to 3'); (ii) SEQ ID NO:15 (non-nucleotide linker positioned between nucleotides 12 and 13, reading 5' to 3'); (iii) SEQ ID NO:16 (non-nucleotide linker positioned between nucleotides 9 and 10, reading 5' to 3'); and (iv) SEQ ID NO:18 (non-nucleotide linker positioned between nucleotides 9 and 10, reading 5' to 3'). Except for the first nucleotide (reading 5' to 3'), which is substituted with the corresponding deoxynucleotide, each nucleotide of the hybridization assay probe having the base sequence of SEQ ID NO:18 is a ribonucleotide modified to include 2'-O-methyl substitution to the ribofuranosyl moiety.

Additionally, unlabeled helper probes having the following base sequences are included in the probe mixture to facilitate hybridization of the hybridization assay probe to *Cryptosporidium parvum* nucleic acid: (i) SEQ ID NO:41 or SEQ ID NO:42 for use with the hybridization assay probe having the base sequence of SEQ ID NO:15; and (ii) any one or a combination of SEQ ID NO:41, SEQ ID NO:42, SEQ ID NO:43 and SEQ ID NO:44 for use with the hybridization assay probe having the base sequence of SEQ ID NO:13 or SEQ ID NO:18 (modified as indicated). Except for the first nucleotide (reading 5' to 3'), which is substituted with the corresponding deoxynucleotide, each nucleotide of the helper probes is a ribonucleotide modified to include a 2'-O-methyl substitution to the ribofuranosyl moiety.

The specificity of the hybridization assay probe for *Cryptosporidium parvum* nucleic acid is determined using a panel of duplicate sample sets, each set containing 100 ng of purified rRNA (50 ng per sample) from an isolate chosen from the group consisting of *Escherichia coli, Cyclospora cayetanensis, Sarcocystis hominis, Eimeria praecox, Entamoeba histolytica, Cryptosporidium parvum* and at least one of *Cryptosporidium muris, Cryptosporidium baileyi, Cryptosporidium serpentis* and *Cryptosporidium wrairi*. *Cryptosporidium parvum* and *Cryptosporidium muris* isolates are available from Waterborne Incorporated (Part No. P102 for *Cryptosporidium parvum* and Part No. P104 for *Cryptosporidium muris*). A set of negative control samples is included to determine background levels.

Each sample is provided to a 12×75 mm polypropylene tube (Gen-Probe Incorporated; Cat. No. 2440). Additionally, each tube is provided with 0.1 pmol of the hybridization assay probe, 5.0 pmol of each helper probe, and 100 μl 1× Hybridization Reagent. To permit hybridization, the tubes are incubated at 60° C. in a circulating water bath (Precision Scientific; Model 260; Cat. No. 51221035) for 30 minutes. Following hybridization, 300 μl Selection Reagent is added to each tube, and the tubes are incubated at 60° C. in the circulating water bath for 10 minutes to hydrolyze acridinium ester labels associated with unhybridized probe. Samples are cooled on ice for 1 minute prior to being analyzed in a LEADER® 450i luminometer equipped with automatic injection of the Detection Reagents. A net RLU value greater than 10,000 RLU is considered to be a positive result, and a net RLU value less than 10,000 RLU is considered to be a negative result. Net RLU values are based on the average RLU value of each sample set minus the average RLU value for the negative control set (i.e., background signal).

Example 4

Sensitivity of *Cryptosporidium parvum* Hybridization Assay Probes

This example employed controls having target-containing rRNA transcripts and water samples containing varying amounts of *Cryptosporidium parvum* oocysts to demonstrate the sensitivity of an acridinium ester-labeled hybridization assay probe for detecting *Cryptosporidium parvum* nucleic acid in a sample. The hybridization assay probe was synthesized, as described above, to have the base sequence of SEQ ID NO:13 and to include a non-nucleotide linker positioned between nucleotides 9 and 10 (reading 5' to 3'). No helper probes were used in this example.

The sensitivity of this *Cryptosporidium parvum* hybridization assay probe was determined using a panel of duplicate controls and samples (with one exception), where the controls included the following: (i) a first set containing 95 μl lysis reagent and no transcript in each tube ("negative control"); (ii) a second set containing 85 μl lysis reagent and 10 μl transcript at a concentration of 0.01 fmol/μl in each tube ("first positive control"); (iii) a third set containing 85 μl lysis reagent and 10 μl transcript at a concentration of 0.1 fmol/μl in each tube ("second positive control"); (iv) a fourth set containing 85 µl lysis reagent and 10 µl transcript at a concentration of 1.0 fmol/µl in each tube ("third positive control"). The lysis reagent was made up of 1.925 ml lysis buffer (10 mM Tris, pH 8.0, 10 mM $CaCl_2$ and 1% (w/v) sodium dodecyl sulfate (SDS)) and 105 µl proteinase K at a concentration of 20 mg/ml.

Five duplicate samples were tested, with members of each set containing oocyst quantities of $2\times10^3$, $1\times10^4$, $1\times10^5$, $1\times10^6$ and $5\times10^6$, respectively, in 1 ml lysis reagent. Unlike the Isolation and Purification method detailed above, *Cryptosporidium parvum* rRNA in this example was isolated from the samples by first centrifuging each sample in a Eppendorf 1.5 ml micro test tube (Brinkmann Instruments, Inc.; Cat. No. 22 60 002 8) at 9,000 rpm for 5 minutes using an Eppendorf microcentrifuge (Brinkmann Instruments, Inc.; Cat. No. 22 62 120-3). All but 100 µl of the supernatant was removed from each tube, and the samples were again centrifuged at 9,000 rpm for 2 minutes in the microcentrifuge. Supernatants were removed so as not to disturb the pellets, which were resuspended in 100 µl lysis reagent.

The samples and controls were all provided with 100 µl Oil Reagent and incubated at 42° C. in a circulating water bath (Lauda Dr. R. Wobser GmbH & Co. KG; Model No. M20-S) for 60 minutes. The samples were then transferred to a dry heat bath (Gen-Probe Incorporated; Cat. No. 4006) and incubated at 95° C. for 90 minutes. Afterwards, each tube received 100 µl probe mix prepared by combining 2.2 ml 1× Hybridization Reagent and 22 µl of the hybridization assay probe at a concentration of 100 fmol/µl. The contents of the tubes were briefly vortexed and again incubated at 60° C. in the circulating water bath for 30 minutes to permit hybridization of probe to target rRNA.

Following hybridization, 300 µl Selection Reagent was added to each tube, and the tubes were briefly vortexed before another incubation at 60° C. in the circulating water bath for 8 minutes to hydrolyze acridinium ester labels associated with unhybridized probe. The contents of the tubes were then cooled at room temperature for 5 minutes prior to being analyzed in a LEADER® 450hc luminometer (Gen-Probe Incorporated) equipped with automatic injection of the Detection Reagents. The RLU and percent coefficient of variation (CV) values from this experiment are presented in Table 1 below, where "net RLU" is the average RLU of the negative control, positive control or sample minus the average RLU for the negative control.

TABLE 1

Hybridization of Probe to Varying Concentrations of Target Nucleic Acid Present in Positive Controls and Isolated from Varying Amounts of *Cryptosporidium parvum* Oocysts

| Sample | RLU | Average RLU | Average Net RLU | % CV |
|---|---|---|---|---|
| Negative Control (0 fmol Target) | 2,449 2,443 | 2,446 | 0 | 0% |
| First Positive Control (0.1 fmol Target) | 6,147 8,597 | 7,372 | 4,926 | 23% |
| Second Positive Control (1 fmol Target) | 43,075 | 43,075 | 40,629 | n/a |
| Third Positive Control (10 fmol Target) | 257,757 274,364 | 266,061 | 263,615 | 4% |
| First Sample ($2\times10^3$ Oocysts) | 4,263 4,448 | 4,356 | 1,190 | 3% |
| Second Sample ($1\times10^4$ Oocysts) | 9,623 9,781 | 9,702 | 7,256 | 1% |
| Third Sample ($1\times10^5$ Oocysts) | 39,267 39,668 | 39,468 | 37,022 | 1% |
| Fourth Sample ($1\times10^6$ Oocysts) | 503,780 385,842 | 444,811 | 442,365 | 19% |
| Fifth Sample ($5\times10^6$ Oocysts) | 461,603 452,482 | 457,043 | 454,597 | 1% |

The results of this experiment suggest an rRNA copy number of approximately 6,000 per oocyst, although this value might have been higher following the novel and more effective Isolation and Purification method described above. This copy number was calculated by linear interpolation using the algorithm y=mx+b, where "y" is the number of relative light units, "m" is the slope, "x" is the number of oocysts and "b" is the y intercept, with 1 fmol of positive control containing approximately $6.02\times10^8$ transcript copies. FIG. 1 is an oocyst titration graph plotting "Average Net RLU" versus "Oocysts" determined by hemocytometer counting, which provides an indication of the oocyst load necessary detect the presence of *Cryptosporidium parvum* in a test sample. These results indicate that the presence of *Cryptosporidium parvum* organisms in a water sample can be directly detected without having to perform a preliminary amplification step to generate sufficient target sequences.

Example 5

Amplification and Detection of *Cryptosporidium parvum* Nucleic Acid

This example illustrates the use of a *Cryptosporidium parvum* hybridization assay probe to detect product of a nucleic acid amplification. In particular, a *Cryptosporidium parvum* hybridization assay probe having the base sequence of SEQ ID NO:5, SEQ ID NO:7, SEQ ID NO:8 or SEQ ID NO:10 is synthesized, as described above, to include a non-nucleotide linker positioned as follows: (i) between nucleotides 18 and 19 for the base sequence of SEQ ID NO:5 (reading 5' to 3'); (ii) between nucleotides 13 and 14 for the base sequence of SEQ ID NO:7 (reading 5' to 3'); (iii) between nucleotides 16 and 17 for the base sequence of SEQ ID NO:8 (reading 5' to 3'); and (iv) between nucleotides 11 and 12 for the base sequence of SEQ ID NO:10 (reading 5' to 3'). Except for the first nucleotide (reading 5' to 3'), which is substituted with the corresponding deoxynucleotide, each nucleotide of the hybridization assay probe having the base sequence of SEQ ID NO:10 is a ribonucleotide modified to include 2'-O-methyl substitution to the ribofuranosyl moiety.

These hybridization assay probes are the same sense as the *Cryptosporidium* target rRNA and are used to detect product of a transcription-mediated amplification. Procedures for performing a transcription-mediated amplification are described supra and by Kacian et al. in U.S. Pat. Nos. 5,399,491 and 5,480,784. In addition, these hybridization assay probes are the opposite sense of the hybridization assay probes having the base sequences of SEQ ID NO:13, SEQ ID NO:15, SEQ ID NO:16 and SEQ ID NO:18, respectively, of Example 3, which are believed to be specific for nucleic acid from *Cryptosporidium parvum* organisms. Accordingly, the hybridization assay probes of this example are expected to be specific for nucleic acid derived from *Cryptosporidium parvum* organisms.

Ribosomal RNA from *Cryptosporidium parvum* is amplified using one of the following promoter-primer/primer combinations when the hybridization assay probe has the base sequence of SEQ ID NO:5, SEQ ID NO:7 or SEQ ID NO:10 (modified as indicated): (i) a promoter-primer having a 5' end promoter base sequence of SEQ ID NO:69 and a 3' end sense template-specific base sequence of SEQ ID NO:59, and a primer having an antisense template-specific base sequence of SEQ ID NO:45; (ii) a promoter-primer having a 5' end promoter base sequence of SEQ ID NO:69 and a 3' end sense template-specific base sequence of SEQ ID NO:59, and a primer having an antisense template-specific base sequence of SEQ ID NO:46; (iii) a promoter-primer having a 5' end promoter base sequence of SEQ ID NO:69 and a 3' end sense template-specific base sequence of SEQ ID NO:60, and a primer having an antisense template-specific base sequence of SEQ ID NO:45; and (iv) a promoter-primer having a 5' end promoter base sequence of SEQ ID NO:69 and a 3' end sense template-specific base sequence of SEQ ID NO:60, and a primer having an antisense template-specific base sequence of SEQ ID NO:46. And, when the hybridization assay probe has the base sequence of SEQ ID NO:8, rRNA from *Cryptosporidium parvum* is amplified using a promoter-primer having a 5' end promoter base sequence of SEQ ID NO:69 and a 3' end sense template-specific base sequence of SEQ ID NO:62, and a primer having an antisense template-specific base sequence of SEQ ID NO:49. A *Cryptosporidium parvum* isolate is available from Waterborne Incorporated as Part No. P102.

Amplification is carried out in 12×75 mm polypropylene tubes (Gen-Probe Incorporated; Cat. No. 2440), each containing 0 amol, 0.2 amol or 2.0 amol of *Cryptosporidium parvum* rRNA in duplicate sets, 15 pmol promoter-primer, 15 pmol primer, 25 µl Amplification Reagent, and distilled, deionized water to bring the total volume in each tube to 75 µl. Each sample receives 200 µl Oil Reagent and is incubated at 95° C. in a dry heat bath (Gen-Probe Incorporated; Cat. No. 4006) for 10 minutes. The samples are then transferred to a circulating water bath (Lauda Dr. R. Wobser GmbH & Co. KG; Model No. M20-S) and incubated at 42° C. for 5 minutes before adding 25 µl of reconstituted Enzyme Reagent to each tube. Following a 60 minute incubation at 42° C. in the circulating water bath, 100 µl 1× Hybridization Reagent containing 100 fmol of the hybridization assay probe is added to each sample, the samples are incubated for 30 minutes at 60° C. in the circulating water bath, and signal from annealed hybridization assay probe is detected in the manner described in Example 3. Sample sets with an average RLU value greater than 10-fold the average RLU value for the negative control (0 amol target rRNA) indicate amplification of the target rRNA, and sample sets with an average RLU value less than 10-fold the average RLU for the negative control indicate no amplification of the target rRNA.

Example 6

Amplification of a *Cryptosporidium parvum* Target Transcript

This example illustrates amplification and detection of a *Cryptosporidium parvum* rRNA transcript sequence at various concentrations. In particular, a *Cryptosporidium parvum* hybridization assay probe having the base sequence of SEQ ID NO:5 was synthesized, as described above, to include a non-nucleotide linker positioned between nucleotides 18 and 19 (reading 5' to 3'). This hybridization assay probe was the same sense as the *Cryptosporidium* target rRNA and was used to detect product of a transcription-mediated amplification. Procedures for performing a transcription-mediated amplification are described supra and by Kacian et al. in U.S. Pat. Nos. 5,399,491 and 5,480,784. In addition, this hybridization assay probe was the opposite sense of the hybridization assay probe having the base sequence of SEQ ID NO:13 of Example 3, which is believed to be specific for nucleic acid from *Cryptosporidium parvum* organisms. Accordingly, the hybridization assay probe of this example was expected to be specific for nucleic acid derived from *Cryptosporidium parvum* organisms.

For this example, two different promoter-primer/primer combinations were employed. The first promoter-primer/primer combination included a promoter-primer having a 5' end promoter base sequence of SEQ ID NO:69 and a 3' end sense template-specific base sequence of SEQ ID NO:59, and a primer having an antisense template-specific base sequence of SEQ ID NO:46 ("primer set one"). The second of these promoter-primer/primer combinations included a promoter-primer having a 5' end promoter base sequence of SEQ ID NO:69 and a 3' end sense template-specific base sequence of SEQ ID NO:59, and a primer having an antisense template-specific base sequence of SEQ ID NO:45 ("primer set two"). The working stock for each primer set was 200 µl distilled, deionized water containing primer and promoter-primer, each at a concentration of 15 pmol/µl.

The working stocks for each primer set were then used to prepare two amplification solutions. The first of these solutions was prepared by combining 375 µl Amplification Reagent, 15 µl primer set one working stock and 585 µl distilled, deionized water ("first amplification solution"). The second of these solutions was prepared by combining 375 µl Amplification Reagent, 15 µl primer set two working stock and 585 µl distilled, deionized water ("second amplification solution").

The probe stock was made up of the hybridization assay probe at a concentration of 100 fmol/µl in approximately 200 µl 1× Hybridization Reagent. From this stock, the probe mix was prepared by combining 30 µl probe stock and 3 ml 2× Hybridization Reagent. This volume of probe stock was sufficient for up to 30 samples.

Transcript dilutions were made to prepare transcript stocks having concentrations of 10 amol/µl, 1 amol/µl, 0.1 amol/µl, 0.01 amol/µl and 0.001 amol/µl in distilled, deionized water. (Each amol of transcript stock contained approximately 600,000 copies of the transcript.) From each of these stock concentrations, a set of four Eppendorf 1.5 ml micro test tubes (Brinkmann Instruments, Inc.; Cat. No. 22 60 002 8) was prepared, each containing 10 µl transcript stock solution. The contents of each of two tubes from each tube set were combined with 65 µl of the first amplification solution, while the contents of each of the other two tubes of each tube set were combined with 65 µl of the second amplification solution. Also included were four negative control tubes (0 amol target), each containing 10 µl of distilled, deionized water. Two of these negative controls received 65 µl of the first amplification solution, while the other two negative controls received 65 µl of the second amplification solution.

Each tube received 200 µl Oil Reagent (both samples and controls), and the tubes were incubated at 95° C. in a dry heat bath (Gen-Probe Incorporated; Cat. No. 4006) for 5 minutes. The tubes were then transferred to a circulating water bath (Lauda Dr. R. Wobser GmbH & Co. KG; Model No. M20-S) for a 5 minute incubation at 42° C. before adding 25 µl of reconstituted Enzyme Reagent to each tube. The tubes were then mixed gently and incubated for an additional 60 minutes at 42° C. in the circulating water bath. Following this third incubation, 100 μl probe mix was added to each tube, the tubes were vortexed, and subjected to a fourth incubation at 60° C. for 30 minutes in the circulating water bath. Each tube was then provided 300 μl Selection Reagent, vortexed, incubated at 60° C. for 10 minutes in the circulating water bath, and cooled on ice water for 1 minute. Signal from annealed hybridization assay probe was detected in the manner described in Example 3, except that a LEADER® 450hc luminometer was used instead of a LEADER® 450i luminometer, and the results are presented in Table 2 below. Sample sets with an average RLU value greater than 10-fold the average RLU value for the negative control (0 amol target rRNA) indicated amplification of the target rRNA, and sample sets with an average RLU value less than 10-fold the average RLU for the negative control indicated no amplification of the target rRNA.

TABLE 2

Hybridization of Probe to Amplification Product Generated from Varying Initial Concentrations of *Cryptosporidium parvum* Target Nucleic Acid Using Different Primer Sets

|  | Sample | RLU | Average | Average | % CV |
|---|---|---|---|---|---|
| Primer Set One | Negative Control (0 amol Target) | 5,507<br>5,540 | 5,524 | 0 | 0% |
|  | First Sample (100 amol Target) | 4,399,434<br>4,240,352 | 4,319,893 | 4,314,370 | 3% |
|  | Second Sample (10 amol Target) | 3,391,820<br>3,431,174 | 3,411,497 | 3,405,974 | 1% |
|  | Third Sample (1 amol Target) | 2,061,629<br>1,883,790 | 1,972,710 | 1,967,186 | 6% |
|  | Fourth Sample (0.1 amol Target) | 328,577<br>285,646 | 307,112 | 301,588 | 10% |
|  | Fifth Sample (0.01 amol Target) | 48,749<br>40,220 | 44,485 | 38,961 | 14% |
| Primer Set Two | Negative Control (0 amol Target) | 6,169<br>10,590 | 8,380 | 0 | 37% |
|  | First Sample (100 amol Target) | 11,913<br>34,670 | 23,292 | 14,912 | 69% |
|  | Second Sample (10 amol Target) | 10,533<br>3,087 | 6,810 | −1,570 | 77% |
|  | Third Sample (1 amol Target) | 10,394<br>10,298 | 10,346 | 1,967 | 1% |
|  | Fourth Sample (0.1 amol Target) | 8,907<br>8,791 | 8,849 | 470 | 1% |
|  | Fifth Sample (0.01 amol Target) | 9,295<br>7,053 | 8,174 | −206 | 19% |

Figure 2:
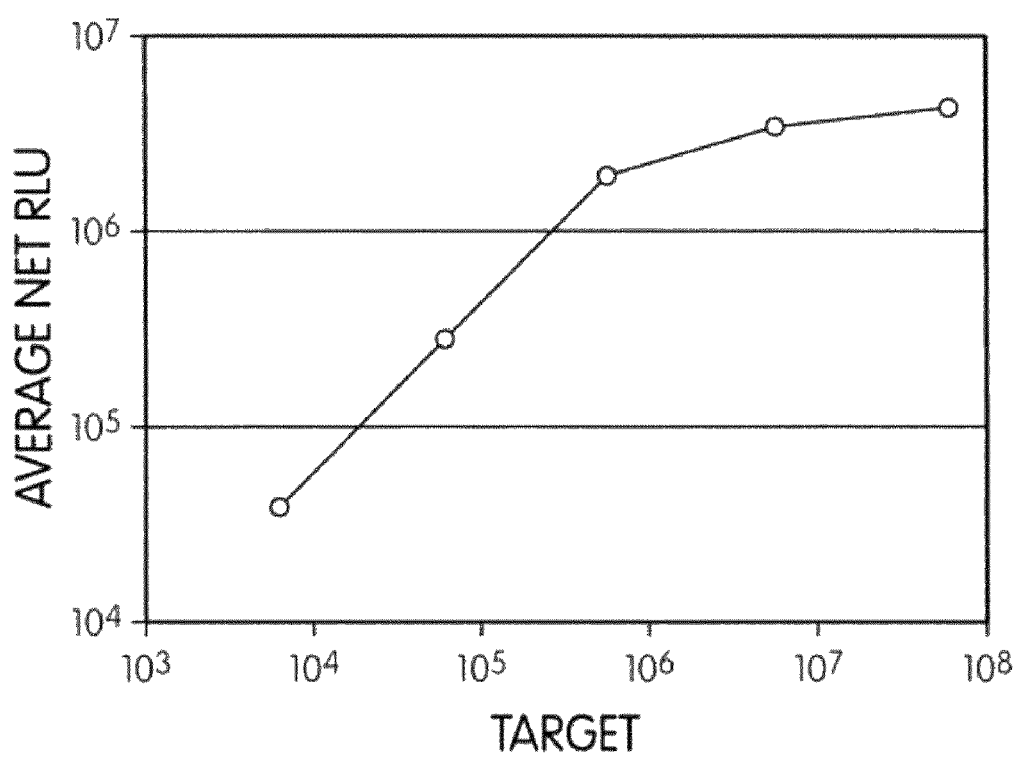
FIG. 2 is an amplification graph plotting "Average Net RLU" versus "Target." This figure provides an indication of the initial rRNA copy number needed to detect the presence of *Cryptosporidium parvum* organisms in a test sample following a transcription-mediated amplification procedure.

The results of this experiment demonstrate that primer set one is useful under these conditions for amplifying the target sequence and can be used to detect the presence of target rRNA from *Cryptosporidium parvum* present in a sample having a copy number at least as low as 6,000 (which is believed to represent a fraction of the rRNA present in an oocyst). FIG. 2 is an amplification graph plotting "Average Net RLU" versus "Target," which provides an indication of the initial rRNA copy number needed to detect the presence of *Cryptosporidium parvum* organisms in a test sample following a transcription-mediated amplification. From this example, it is would appear that 1,000 copies of rRNA (less than the amount expected to be present in a single *Cryptosporidium parvum* oocyst) is sufficient to detect the presence of *Cryptosporidium parvum* organisms in a test sample when sample rRNA is amplified by performing a transcription-mediated amplification. Through routine experimentation, it is believed that the conditions and concentrations set forth in this example could be optimized so that primer set two could likewise amplify (as defined) the target sequence.

Example 7

Amplification of a *Cryptosporidium parvum* Target Transcript in the Presence of rRNA from a Non-Target Organism This example illustrates amplification and detection of a *Cryptosporidium parvum* rRNA transcript sequence in the presence of *Cryptosporidium muris* rRNA at various concentrations of each. In particular, a *Cryptosporidium parvum* hybridization assay probe having the base sequence of SEQ ID NO:5 was synthesized, as described above, to include a non-nucleotide linker positioned between nucleotides 18 and 19 (reading 5' to 3'). This hybridization assay probe was the same sense as the *Cryptosporidium* target rRNA and was used to detect product of a transcription-mediated amplification. Procedures for performing a transcription-mediated amplification are described supra and by Kacian et al. in U.S. Pat. Nos. 5,399,491 and 5,480,784. In addition, this hybridization assay probe was the opposite sense of the hybridization assay probe having the base sequence of SEQ ID NO:13 of Example 3, which is believed to be specific for nucleic acid from *Cryptosporidium parvum* organisms. Accordingly, it would be expected that the hybridization assay probe of this example would be specific for nucleic acid derived from *Cryptosporidium parvum* organisms.

In this example, a total of 20 12×75 mm polypropylene tubes (Gen-Probe Incorporated; Cat. No. 2440) were set up in a matrix format to contain the amounts of *Cryptosporidium parvum* transcript rRNA and *Cryptosporidium muris* rRNA indicated in Table 3 below. The *Cryptosporidium parvum* oocysts used to generate the transcript of this example were obtained from Waterborne Incorporated under Part No. P102. The *Cryptosporidium muris* oocysts were obtained from a private source, however, a *Cryptosporidium muris* isolate is available from Waterborne Incorporated under Part No. 104. For *Cryptosporidium muris*, duplicate sets of tubes were provided with 0 amol, 0.2 amol, 2 amol, 20 amol and 200 amol of *Cryptosporidium muris* sample rRNA. Each member of these sets of tubes was then matched with one of two *Cryptosporidium parvum* tubes having either 0 amol or 2 amol *Cryptosporidium parvum* transcript rRNA. The promoter-primer/primer combination provided to each tube included a promoter-primer having a 5' end promoter base sequence of SEQ ID NO:69 and a 3' end sense template-specific base sequence of SEQ ID NO:59, and a primer having an antisense template-specific base sequence of SEQ ID NO:46. This primer set was used to prepare an amplification solution made up of 750 μl Amplification Reagent and 30 μl of a primer working stock containing 15 pmol/μl each of the promoter-primer and the primer in distilled, deionized water.

Each tube was provided 25 μl of the amplification solution, and the non-control tubes were provided with 10 μl of the appropriate dilution of sample rRNA. The total volume of all tubes was brought up to 75 μl with distilled, deionized water. The tubes were separately provided 200 μl Oil Reagent and then incubated at 95° C. in a dry heat bath (Gen-Probe Incorporated; Cat. No. 4006) for 10 minutes, followed by a 5 minute incubation at 42° C. in a circulating water bath (Lauda Dr. R. Wobser GmbH & Co. KG; Model No. M20-S). After adding 25 µl of reconstituted Enzyme Reagent to each tube, the tubes were mixed gently and incubated for an additional 60 minutes at 42° C. in the circulating water bath. Following this third incubation, 100 µl probe mix was added to each tube, the probe mix being comprised of 1 pmol/ml of the hybridization assay probe in 1× Hybridization Reagent. The tubes were then vortexed and subjected to a fourth incubation at 60° C. for 30 minutes in the circulating water bath. Each tube was then provided 300 µl Selection Reagent, vortexed, incubated at 60° C. for 10 minutes in the circulating water bath, and then cooled on ice for 1 minute. Signal from annealed hybridization assay probe was detected in the manner described in Example 3, except that a LEADER® 450hc luminometer was used instead of a LEADER® 450i luminometer, and the results are presented in Table 3 below. Samples with an RLU value greater than 10-fold the RLU value for the negative control (0 amol target rRNA and 0 amol non-target rRNA) indicated amplification of the target rRNA or non-target rRNA, and samples with an RLU value less than 10-fold the RLU for the negative control indicated no amplification of the target rRNA or non-target rRNA.

TABLE 3

Hybridization of Probe to Amplification Product Generated from Varying Initial Concentrations of *Cryptosporidium parvum* Target Transcript in the Presence of Varying Concentrations of *Cryptosporidium muris* rRNA

| C. muris (amol rRNA) | C. parvum (amol rRNA) | RLU | Fold Background |
|---|---|---|---|
| 0 | 0 | 24,215 | 1 |
| 0 | 2 | 3,908,824 | 161 |
| 0.2 | 0 | 25,449 | 1 |
| 0.2 | 2 | 3,272,793 | 135 |
| 2 | 0 | 38,866 | 2 |
| 2 | 2 | 3,786,620 | 156 |
| 20 | 0 | 81,328 | 3 |
| 20 | 2 | 2,408,251 | 99 |
| 200 | 0 | 116,466 | 5 |
| 200 | 2 | 4,359,656 | 180 |

The results of this experiment demonstrate that the primer set is useful for amplifying a target sequence present in nucleic acid from *Cryptosporidium parvum* in the presence of potentially interfering nucleic acid from a closely-related, non-targeted organism. Additionally, the data demonstrates that the hybridization assay probe specifically hybridizes to amplicon derived from *Cryptosporidium parvum* nucleic acid.

The invention claimed is:

1. A hybridization assay probe comprising a detectable label and the base sequence of SEQ ID NO:6, SEQ ID NO:10, SEQ ID NO:14 or SEQ ID NO:18, wherein the probe hybridizes to nucleic acid derived from *Cryptosporidium parvum* under stringent conditions to form a probe:target hybrid stable for detection, and wherein the probe does not hybridize to nucleic acid derived from *Cryptosporidium muris*, *Cryptosporidium baileyi*, or *Cryptosporidium wrairi* to form a probe:non-target hybrid stable for detection under the stringent conditions.

2. The probe of claim 1, wherein the probe is up to 27 bases in length.

3. The probe of claim 1, wherein the base sequence of the probe consists of the base sequence of SEQ ID NO:6, SEQ ID NO:10, SEQ ID NO:14 or SEQ ID NO:18.

4. The probe of claim 1, wherein the probe comprises at least one base sequence that does not stably hybridize to nucleic acid derived from *Cryptosporidium parvum*, *Cryptosporidium muris*, *Cryptosporidium baileyi*, or *Cryptosporidium wrairi* under the stringent conditions.

5. The probe of claim 4, wherein the probe comprises a pair of base sequences that hybridize to each other when the probe is not hybridized to nucleic acid derived from *Cryptosporidium parvum* under the stringent conditions.

6. The probe of claim 5, wherein the probe comprises a group of interacting labels.

7. The probe of claim 6, wherein the interacting labels include a luminescent label and a quencher label.

8. The probe of claim 1, wherein the probe includes at least one ribonucleotide modified to include a 2'-O-methyl substitution to the ribofuranosyl moiety.

9. The probe of claim 1, wherein a pseudo peptide backbone joins at least a portion of the bases of the probe.

10. The probe of claim 1, wherein the stringent conditions comprise 50 mM succinic acid, 1% (w/v) LLS, 7.5 mM aldrithiol-2, 0.6 M LiCl, 115 mM LiOH, 10 mM EDTA, 10 mM EGTA, 1.5% (v/v) ethyl alcohol (absolute), pH to 4.7, at a temperature of about 60° C.

11. A method for determining the presence of *Cryptosporidium parvum* in a test sample, the method comprising the steps of:
contacting the test sample with the probe of claim 1 under stringent conditions; and
determining whether the probe:target hybrid has formed under the stringent conditions as an indication of the presence of *Cryptosporidium parvum* in the test sample.

12. The method of claim 11, wherein the probe is up to 27 bases in length.

13. The method of claim 11, wherein the base sequence of the probe consists of the base sequence of SEQ ID NO:6, SEQ ID NO:10, SEQ ID NO:14 or SEQ ID NO:18.

14. The method of claim 11, wherein the probe comprises at least one base sequence that does not stably hybridize to nucleic acid derived from *Cryptosporidium parvum, Cryptosporidium muris, Cryptosporidium baileyi*, or *Cryptosporidium wrairi* under the stringent conditions.

15. The method of claim 14, wherein the probe comprises a pair of base sequences that hybridize to each other when the probe is not hybridized to nucleic acid derived from *Cryptosporidium parvum* under the stringent conditions.

16. The method of claim 15, wherein the probe comprises a group of interacting labels.

17. The method of claim 16, wherein the interacting labels include a luminescent label and a quencher label.

18. The method of claim 11, wherein the probe includes at least one ribonucleotide modified to include a 2'-O-methyl substitution to the ribofuranosyl moiety.

19. The method of claim 11, wherein a pseudo peptide backbone joins at least a portion of the bases of the probe.

* * * * *

SEQUENCE LISTING

<160> NUMBER OF SEQ ID NOS: 69

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
ctatcagctt tagacggtag gg                                        22

<210> SEQ ID NO 2
<211> LENGTH: 22
<212> TYPE: RNA
<213> ORGANISM: Artificial Sequence
<220> FEATURE:
<223> OTHER INFORMATION: Synthetic Construct

<400> SEQUENCE: 2
cuaucagcuu uagacgguag gg                                        22

<210> SEQ ID NO 3
<211> LENGTH: 22
<212> TYPE: DNA
<213> ORGANISM: Artificial Sequence
<220> FEATURE:
<223> OTHER INFORMATION: Synthetic Construct

<400> SEQUENCE: 3
ccctaccgtc taaagctgat ag                                        22

<210> SEQ ID NO 4
<211> LENGTH: 22
<212> TYPE: RNA
<213> ORGANISM: Artificial Sequence
<220> FEATURE:
<223> OTHER INFORMATION: Synthetic Construct

<400> SEQUENCE: 4
cccuaccguc uaaagcugau ag                                              22

<210> SEQ ID NO 5
<211> LENGTH: 27
<212> TYPE: DNA
<213> ORGANISM: Artificial Sequence
<220> FEATURE:
<223> OTHER INFORMATION: Synthetic Construct

<400> SEQUENCE: 5
gcgaaaaaac tcgactttat ggaaggg                                         27

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
aactcgactt tatggaaggg                                                 20

<210> SEQ ID NO 7
<211> LENGTH: 25
<212> TYPE: DNA
<213> ORGANISM: Artificial Sequence
<220> FEATURE:
<223> OTHER INFORMATION: Synthetic Construct

<400> SEQUENCE: 7
aaaactcgac tttatggaag ggttg                                           25

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8
gttaaagaca aactaatgcg aaagc                                           25

<210> SEQ ID NO 9
<211> LENGTH: 27
<212> TYPE: RNA
<213> ORGANISM: Artificial Sequence
<220> FEATURE:
<223> OTHER INFORMATION: Synthetic Construct

<400> SEQUENCE: 9
gcgaaaaaac ucgacuuuau ggaaggg                                         27

<210> SEQ ID NO 10
<211> LENGTH: 20
<212> TYPE: RNA
<213> ORGANISM: Artificial Sequence
<220> FEATURE:
<223> OTHER INFORMATION: Synthetic Construct

<400> SEQUENCE: 10
aacucgacuu uauggaaggg                                                 20

<210> SEQ ID NO 11
<211> LENGTH: 25

```
<212> TYPE: RNA
<213> ORGANISM: Artificial Sequence
<220> FEATURE:
<223> OTHER INFORMATION: Synthetic Construct

<400> SEQUENCE: 11
aaaacucgac uuuauggaag gguug                                              25

<210> SEQ ID NO 12
<211> LENGTH: 25
<212> TYPE: RNA
<213> ORGANISM: Artificial Sequence
<220> FEATURE:
<223> OTHER INFORMATION: Synthetic Construct

<400> SEQUENCE: 12
guuaaagaca aacuaaugcg aaagc                                              25

<210> SEQ ID NO 13
<211> LENGTH: 27
<212> TYPE: DNA
<213> ORGANISM: Artificial Sequence
<220> FEATURE:
<223> OTHER INFORMATION: Synthetic Construct

<400> SEQUENCE: 13
cccttccata aagtcgagtt ttttcgc                                            27

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
cccttccata aagtcgagtt                                                    20

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
caacccttcc ataaagtcga gtttt                                              25

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct

<400> SEQUENCE: 16
gctttcgcat tagtttgtct ttaac                                              25

<210> SEQ ID NO 17
<211> LENGTH: 27
<212> TYPE: RNA
<213> ORGANISM: Artificial Sequence
<220> FEATURE:
<223> OTHER INFORMATION: Synthetic Construct

<400> SEQUENCE: 17
cccuuccaua aagucgaguu uuuucgc                                            27
```

<210> SEQ ID NO 18
<211> LENGTH: 20
<212> TYPE: RNA
<213> ORGANISM: Artificial Sequence
<220> FEATURE:
<223> OTHER INFORMATION: Synthetic Construct

<400> SEQUENCE: 18
cccuuccaua aagucgaguu                                              20

<210> SEQ ID NO 19
<211> LENGTH: 25
<212> TYPE: RNA
<213> ORGANISM: Artificial Sequence
<220> FEATURE:
<223> OTHER INFORMATION: Synthetic Construct

<400> SEQUENCE: 19
caacccuucc auaaagucga guuuu                                        25

<210> SEQ ID NO 20
<211> LENGTH: 25
<212> TYPE: RNA
<213> ORGANISM: Artificial Sequence
<220> FEATURE:
<223> OTHER INFORMATION: Synthetic Construct

<400> SEQUENCE: 20
gcuuucgcau uaguuugucu uuaac                                        25

<210> SEQ ID NO 21
<211> LENGTH: 23
<212> TYPE: DNA
<213> ORGANISM: Artificial Sequence
<220> FEATURE:
<223> OTHER INFORMATION: Synthetic Construct

<400> SEQUENCE: 21
gacatatcat tcaagtttct gac                                          23

<210> SEQ ID NO 22
<211> LENGTH: 24
<212> TYPE: DNA
<213> ORGANISM: Artificial Sequence
<220> FEATURE:
<223> OTHER INFORMATION: Synthetic Construct

<400> SEQUENCE: 22
ttggcctacc gtggcaatga cggg                                         24

<210> SEQ ID NO 23
<211> LENGTH: 23
<212> TYPE: RNA
<213> ORGANISM: Artificial Sequence
<220> FEATURE:
<223> OTHER INFORMATION: Synthetic Construct

<400> SEQUENCE: 23
gacauaucau ucaaguuucu gac                                          23

<210> SEQ ID NO 24
<211> LENGTH: 24
<212> TYPE: RNA
<213> ORGANISM: Artificial Sequence
<220> FEATURE:
<223> OTHER INFORMATION: Synthetic Construct

```
<400> SEQUENCE: 24
uuggccuacc guggcaauga cggg                                      24

<210> SEQ ID NO 25
<211> LENGTH: 23
<212> TYPE: DNA
<213> ORGANISM: Artificial Sequence
<220> FEATURE:
<223> OTHER INFORMATION: Synthetic Construct

<400> SEQUENCE: 25
gtcagaaact tgaatgatat gtc                                       23

<210> SEQ ID NO 26
<211> LENGTH: 24
<212> TYPE: DNA
<213> ORGANISM: Artificial Sequence
<220> FEATURE:
<223> OTHER INFORMATION: Synthetic Construct

<400> SEQUENCE: 26
cccgtcattg ccacggtagg ccaa                                      24

<210> SEQ ID NO 27
<211> LENGTH: 23
<212> TYPE: RNA
<213> ORGANISM: Artificial Sequence
<220> FEATURE:
<223> OTHER INFORMATION: Synthetic Construct

<400> SEQUENCE: 27
gucagaaacu ugaaugauau guc                                       23

<210> SEQ ID NO 28
<211> LENGTH: 24
<212> TYPE: RNA
<213> ORGANISM: Artificial Sequence
<220> FEATURE:
<223> OTHER INFORMATION: Synthetic Construct

<400> SEQUENCE: 28
cccgucauug ccacgguagg ccaa                                      24

<210> SEQ ID NO 29
<211> LENGTH: 32
<212> TYPE: DNA
<213> ORGANISM: Artificial Sequence
<220> FEATURE:
<223> OTHER INFORMATION: Synthetic Construct

<400> SEQUENCE: 29
ggataaccgt ggtaattcta gagctaatac at                             32

<210> SEQ ID NO 30
<211> LENGTH: 26
<212> TYPE: DNA
<213> ORGANISM: Artificial Sequence
<220> FEATURE:
<223> OTHER INFORMATION: Synthetic Construct

<400> SEQUENCE: 30
ccgtggtaat tctagagcta atacat                                    26

<210> SEQ ID NO 31
<211> LENGTH: 23
```

```
<212> TYPE: DNA
<213> ORGANISM: Artificial Sequence
<220> FEATURE:
<223> OTHER INFORMATION: Synthetic Construct

<400> SEQUENCE: 31
ttgtatttat tagataaaga acc                                            23

<210> SEQ ID NO 32
<211> LENGTH: 29
<212> TYPE: DNA
<213> ORGANISM: Artificial Sequence
<220> FEATURE:
<223> OTHER INFORMATION: Synthetic Construct

<400> SEQUENCE: 32
ttgtatttat tagataaaga accaatata                                      29

<210> SEQ ID NO 33
<211> LENGTH: 32
<212> TYPE: RNA
<213> ORGANISM: Artificial Sequence
<220> FEATURE:
<223> OTHER INFORMATION: Synthetic Construct

<400> SEQUENCE: 33
ggauaaccgu gguaauucua gagcuaauac au                                  32

<210> SEQ ID NO 34
<211> LENGTH: 26
<212> TYPE: RNA
<213> ORGANISM: Artificial Sequence
<220> FEATURE:
<223> OTHER INFORMATION: Synthetic Construct

<400> SEQUENCE: 34
ccgugguaau ucuagagcua auacau                                         26

<210> SEQ ID NO 35
<211> LENGTH: 23
<212> TYPE: RNA
<213> ORGANISM: Artificial Sequence
<220> FEATURE:
<223> OTHER INFORMATION: Synthetic Construct

<400> SEQUENCE: 35
uuguauuuau uagauaaaga acc                                            23

<210> SEQ ID NO 36
<211> LENGTH: 29
<212> TYPE: RNA
<213> ORGANISM: Artificial Sequence
<220> FEATURE:
<223> OTHER INFORMATION: Synthetic Construct

<400> SEQUENCE: 36
uuguauuuau uagauaaaga accaauaua                                      29

<210> SEQ ID NO 37
<211> LENGTH: 32
<212> TYPE: DNA
<213> ORGANISM: Artificial Sequence
<220> FEATURE:
<223> OTHER INFORMATION: Synthetic Construct

<400> SEQUENCE: 37
atgtattagc tctagaatta ccacggttat cc                                  32
```

```
<210> SEQ ID NO 38
<211> LENGTH: 26
<212> TYPE: DNA
<213> ORGANISM: Artificial Sequence
<220> FEATURE:
<223> OTHER INFORMATION: Synthetic Construct

<400> SEQUENCE: 38
atgtattagc tctagaatta ccacgg                                              26

<210> SEQ ID NO 39
<211> LENGTH: 23
<212> TYPE: DNA
<213> ORGANISM: Artificial Sequence
<220> FEATURE:
<223> OTHER INFORMATION: Synthetic Construct

<400> SEQUENCE: 39
ggttctttat ctaataaata caa                                                 23

<210> SEQ ID NO 40
<211> LENGTH: 29
<212> TYPE: DNA
<213> ORGANISM: Artificial Sequence
<220> FEATURE:
<223> OTHER INFORMATION: Synthetic Construct

<400> SEQUENCE: 40
tatattggtt ctttatctaa taaatacaa                                           29

<210> SEQ ID NO 41
<211> LENGTH: 32
<212> TYPE: RNA
<213> ORGANISM: Artificial Sequence
<220> FEATURE:
<223> OTHER INFORMATION: Synthetic Construct

<400> SEQUENCE: 41
auguauuagc ucuagaauua ccacgguuau cc                                       32

<210> SEQ ID NO 42
<211> LENGTH: 26
<212> TYPE: RNA
<213> ORGANISM: Artificial Sequence
<220> FEATURE:
<223> OTHER INFORMATION: Synthetic Construct

<400> SEQUENCE: 42
auguauuagc ucuagaauua ccacgg                                              26

<210> SEQ ID NO 43
<211> LENGTH: 23
<212> TYPE: RNA
<213> ORGANISM: Artificial Sequence
<220> FEATURE:
<223> OTHER INFORMATION: Synthetic Construct

<400> SEQUENCE: 43
gguucuuuau cuaauaaaua caa                                                 23

<210> SEQ ID NO 44
<211> LENGTH: 29
<212> TYPE: RNA
<213> ORGANISM: Artificial Sequence
<220> FEATURE:
<223> OTHER INFORMATION: Synthetic Construct
```

```
<400> SEQUENCE: 44
uauauugguu cuuuaucuaa uaaauacaa                              29

<210> SEQ ID NO 45
<211> LENGTH: 23
<212> TYPE: DNA
<213> ORGANISM: Artificial Sequence
<220> FEATURE:
<223> OTHER INFORMATION: Synthetic Construct

<400> SEQUENCE: 45
gccatgcatg tctaagtata aac                                    23

<210> SEQ ID NO 46
<211> LENGTH: 23
<212> TYPE: DNA
<213> ORGANISM: Artificial Sequence
<220> FEATURE:
<223> OTHER INFORMATION: Synthetic Construct

<400> SEQUENCE: 46
ggataaccgt ggtaattcta gag                                    23

<210> SEQ ID NO 47
<211> LENGTH: 23
<212> TYPE: DNA
<213> ORGANISM: Artificial Sequence
<220> FEATURE:
<223> OTHER INFORMATION: Synthetic Construct

<400> SEQUENCE: 47
ggtgactcat aataacttta cgg                                    23

<210> SEQ ID NO 48
<211> LENGTH: 22
<212> TYPE: DNA
<213> ORGANISM: Artificial Sequence
<220> FEATURE:
<223> OTHER INFORMATION: Synthetic Construct

<400> SEQUENCE: 48
ctaccacatc taaggaaggc ag                                     22

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct

<400> SEQUENCE: 49
gtatttaaca gtcagaggtg                                        20

<210> SEQ ID NO 50
<211> LENGTH: 22
<212> TYPE: DNA
<213> ORGANISM: Artificial Sequence
<220> FEATURE:
<223> OTHER INFORMATION: Synthetic Construct

<400> SEQUENCE: 50
gccaaggatg ttttcattaa tc                                     22

<210> SEQ ID NO 51
<211> LENGTH: 23
```

-continued

```
<212> TYPE: RNA
<213> ORGANISM: Artificial Sequence
<220> FEATURE:
<223> OTHER INFORMATION: Synthetic Construct

<400> SEQUENCE: 51
gccaugcaug ucuaaguaua aac                                              23

<210> SEQ ID NO 52
<211> LENGTH: 23
<212> TYPE: RNA
<213> ORGANISM: Artificial Sequence
<220> FEATURE:
<223> OTHER INFORMATION: Synthetic Construct

<400> SEQUENCE: 52
ggauaaccgu gguaauucua gag                                              23

<210> SEQ ID NO 53
<211> LENGTH: 23
<212> TYPE: RNA
<213> ORGANISM: Artificial Sequence
<220> FEATURE:
<223> OTHER INFORMATION: Synthetic Construct

<400> SEQUENCE: 53
ggugacucau aauaacuuua cgg                                              23

<210> SEQ ID NO 54
<211> LENGTH: 22
<212> TYPE: RNA
<213> ORGANISM: Artificial Sequence
<220> FEATURE:
<223> OTHER INFORMATION: Synthetic Construct

<400> SEQUENCE: 54
cuaccacauc uaaggaaggc ag                                               22

<210> SEQ ID NO 55
<211> LENGTH: 20
<212> TYPE: RNA
<213> ORGANISM: Artificial Sequence
<220> FEATURE:
<223> OTHER INFORMATION: Synthetic Construct

<400> SEQUENCE: 55
guauuuaaca gucagaggug                                                  20

<210> SEQ ID NO 56
<211> LENGTH: 22
<212> TYPE: RNA
<213> ORGANISM: Artificial Sequence
<220> FEATURE:
<223> OTHER INFORMATION: Synthetic Construct

<400> SEQUENCE: 56
gccaaggaug uuuucauuaa uc                                               22

<210> SEQ ID NO 57
<211> LENGTH: 23
<212> TYPE: DNA
<213> ORGANISM: Artificial Sequence
<220> FEATURE:
<223> OTHER INFORMATION: Synthetic Construct

<400> SEQUENCE: 57
gtttatactt agacatgcat ggc                                              23
```

```
<210> SEQ ID NO 58
<211> LENGTH: 23
<212> TYPE: DNA
<213> ORGANISM: Artificial Sequence
<220> FEATURE:
<223> OTHER INFORMATION: Synthetic Construct

<400> SEQUENCE: 58
ctctagaatt accacggtta tcc                                              23

<210> SEQ ID NO 59
<211> LENGTH: 23
<212> TYPE: DNA
<213> ORGANISM: Artificial Sequence
<220> FEATURE:
<223> OTHER INFORMATION: Synthetic Construct

<400> SEQUENCE: 59
ccgtaaagtt attatgagtc acc                                              23

<210> SEQ ID NO 60
<211> LENGTH: 22
<212> TYPE: DNA
<213> ORGANISM: Artificial Sequence
<220> FEATURE:
<223> OTHER INFORMATION: Synthetic Construct

<400> SEQUENCE: 60
ctgccttcct tagatgtggt ag                                               22

<210> SEQ ID NO 61
<211> LENGTH: 20
<212> TYPE: DNA
<213> ORGANISM: Artificial Sequence
<220> FEATURE:
<223> OTHER INFORMATION: Synthetic Construct

<400> SEQUENCE: 61
cacctctgac tgttaaatac                                                  20

<210> SEQ ID NO 62
<211> LENGTH: 22
<212> TYPE: DNA
<213> ORGANISM: Artificial Sequence
<220> FEATURE:
<223> OTHER INFORMATION: Synthetic Construct

<400> SEQUENCE: 62
gattaatgaa aacatccttg gc                                               22

<210> SEQ ID NO 63
<211> LENGTH: 23
<212> TYPE: RNA
<213> ORGANISM: Artificial Sequence
<220> FEATURE:
<223> OTHER INFORMATION: Synthetic Construct

<400> SEQUENCE: 63
guuuauacuu agacaugcau ggc                                              23

<210> SEQ ID NO 64
<211> LENGTH: 23
<212> TYPE: RNA
<213> ORGANISM: Artificial Sequence
<220> FEATURE:
<223> OTHER INFORMATION: Synthetic Construct
```

```
<400> SEQUENCE: 64
cucuagaauu accacgguua ucc                                              23

<210> SEQ ID NO 65
<211> LENGTH: 23
<212> TYPE: RNA
<213> ORGANISM: Artificial Sequence
<220> FEATURE:
<223> OTHER INFORMATION: Synthetic Construct

<400> SEQUENCE: 65
ccguaaaguu auuaugaguc acc                                              23

<210> SEQ ID NO 66
<211> LENGTH: 22
<212> TYPE: RNA
<213> ORGANISM: Artificial Sequence
<220> FEATURE:
<223> OTHER INFORMATION: Synthetic Construct

<400> SEQUENCE: 66
cugccuuccu uagauguggu ag                                               22

<210> SEQ ID NO 67
<211> LENGTH: 20
<212> TYPE: RNA
<213> ORGANISM: Artificial Sequence
<220> FEATURE:
<223> OTHER INFORMATION: Synthetic Construct

<400> SEQUENCE: 67
caccucugac uguuaaauac                                                  20

<210> SEQ ID NO 68
<211> LENGTH: 22
<212> TYPE: RNA
<213> ORGANISM: Artificial Sequence
<220> FEATURE:
<223> OTHER INFORMATION: Synthetic Construct

<400> SEQUENCE: 68
gauuaaugaa aacauccuug gc                                               22

<210> SEQ ID NO 69
<211> LENGTH: 27
<212> TYPE: DNA
<213> ORGANISM: Artificial Sequence
<220> FEATURE:
<223> OTHER INFORMATION: Synthetic Construct (T7 Promoter)

<400> SEQUENCE: 69
aatttaatac gactcactat agggaga                                          27
```